United States Patent
Davidson et al.

(10) Patent No.: US 6,551,586 B1
(45) Date of Patent: Apr. 22, 2003

(54) MALARIA VACCINE BASED UPON THE ADDITION OF A MSA1 PEPTIDE

(75) Inventors: Eugene A. Davidson, Washington, DC (US); Shutong Yang, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/117,415

(22) Filed: Nov. 27, 1998

Related U.S. Application Data

(63) Continuation-in-part of application No. 08/593,006, filed on Jan. 29, 1996, now abandoned.
(60) Provisional application No. PCT/US97/01395, filed on Jan. 29, 1996.

(51) Int. Cl.$^7$ ................................................. A01N 63/00
(52) U.S. Cl. ..................... 424/93.2; 514/44; 435/320.1; 435/69.1; 435/325; 435/455
(58) Field of Search ........................... 514/44; 536/23.1, 536/23.4, 24.1; 435/69.1, 320.1, 325, 455; 424/93.1, 93.2, 184.1

(56) References Cited

U.S. PATENT DOCUMENTS

| | | | |
|---|---|---|---|
| 5,032,520 A | | 7/1991 | Binns et al. ................. 435/325 |
| 5,225,534 A | | 7/1993 | Certa .......................... 530/350 |
| 5,541,087 A | * | 7/1996 | Lo et al. ...................... 435/697 |
| 5,585,268 A | | 12/1996 | Knapp et al. ............. 435/252.3 |
| 5,756,101 A | * | 5/1998 | Paoletti et al. ........... 424/199.1 |
| 5,766,597 A | * | 6/1998 | Paoletti et al. ........... 424/199.1 |
| 5,876,964 A | * | 3/1999 | Croteau et al. ............. 435/69.1 |
| 5,948,647 A | * | 9/1999 | Ring .......................... 435/69.6 |

FOREIGN PATENT DOCUMENTS

| | | |
|---|---|---|
| WO | WO94/21680 | 9/1994 |
| WO | WO 94/28930 | 12/1994 |
| WO | WO 96/34105 | 10/1996 |
| WO | WO 97/30159 | 8/1997 |

OTHER PUBLICATIONS

McCluskie et al., Molecular Medicine, 5, 287–300, 1999.*
Stoute et al., BioDrugs, 10/2, pp. 123–136, 1998.*
Database Biotechds, AN: 1996–13489, Hestrom et al., abstract, Nov. 1995.*
Murphy et al., Parasitology, 11, Pt 2, pp. 177–183, 1990.*
Longacre et al., Mol. Biochem. Parasitol., 64, 2, 191–205, 1994.*
Hui et al. Infection and Immunity 61:3403 (1993).
Gierasch Perspectives in Biochemistry 28:923 (1989).
von Heijne Subcellular Biochemistry 22:1 (1994).
Englund Annu. Review Biochem. 62: 121 (1993).
Arita Nature 279:293 (1979).
Mackett et al. J. Gen Virol. 67:2067 (1986).
Houard et al. J Gen. Virol. 76:421 (1995).
Fujii et al. J. Gen Virol 76:1339 (1995).
Rodrigues et al. J Immunol. 153:4636 (1994).
Earl et al. Current Protocols in Molecular Biology Units 16.1–16.2 (1993).
Smith et al. Gene 25:21 (1983).
Chakrabarti et al. Nature 320: 535 (1986).
Hu et al. Nature 320:537 (1986).
Ball et al: Proc. Natl. Acad. Sci 83:246 (1986).
de La Salle et al. Nature 316:268 (1985).
Langford et al. Mol. Cell Biol. 6:3191 (1986).
Blackman et al. Mol.Biochem. Parastilol. 49:29 (1991).
Perrin et al. J. Exp. Med 160:441 (1984).
Siddiqui et al. Proc. Natl. Acad. Sci. USA 84:3014 (1987).
Perrin et al. Immunol. Rev. 61: 245 (1982).
Holder et al. Parasitology 94. 199 (1987).
McBride et al. Mol.Biochem. Parastilol. 23:71 (1987).
Blackman et al. Mol.Biochem. Parastilol. 49:35 (1991).
Fox et al. Infect. Imm. 61:2309 (1993).
Holder et al. Parasite Immunol. 10:607 (1988).
Günzburg Molecular Medicine Today vol. 12, 9:410–417, 1995.
Coghlan New Scientist, vol. 148 pp. 14–15, 1995.
Crystal Science 270: 404–407 (1995).
Robert Whalen Emerging Infectious Diseases 2:168–175.
Etlinger Immunology Today 1312:52–55 (1992).
Cryz Vaccine 14: 683–687 (1996).
Kaslow D. C. et al. "Expression and Antigenicity of Plasmodium Falciparum Major Merozoite Surface Protein (MSP119) Variants Secreted From Saccharomyes Cerevisiae" *Molecular aned Biochemical Parasitology*, 63(2): 283–289, 1994.
Sandhu J. S. and Kennedy J F. "Expression of the Merozoite Surface Protein GP195 in Vaccinia Virus" *Vaccine*, 12(1): 56–64, 1994.
Kumar S. et al. "Immunogencity and In Vivo Efficacy of Recombinant Plasmodium Falciparum Merozoite Surface Protein–1 in Aotus Monkeys" *Molecular Medicine*, 1(3): 325–332, 1995.

* cited by examiner

*Primary Examiner*—Dave Trong Nguyen
(74) *Attorney, Agent, or Firm*—Henry D. Coleman; Coleman Sudol Sapone P.C.

(57) ABSTRACT

The present invention relates to an expression vector which expresses a malaria MSA1 peptide in combination with a signal peptide and anchor peptide in a host animal. The MSA1 peptide is combined with a signal peptide and anchor peptide for expression. Chimeric peptides being expressed with both signal peptides and anchor peptides were the most effective in eliciting an immunogenic response from a vaccinated host.

8 Claims, 13 Drawing Sheets

GENE SEQUENCE OF MSA1C-(Si,A)

Figure 1A:
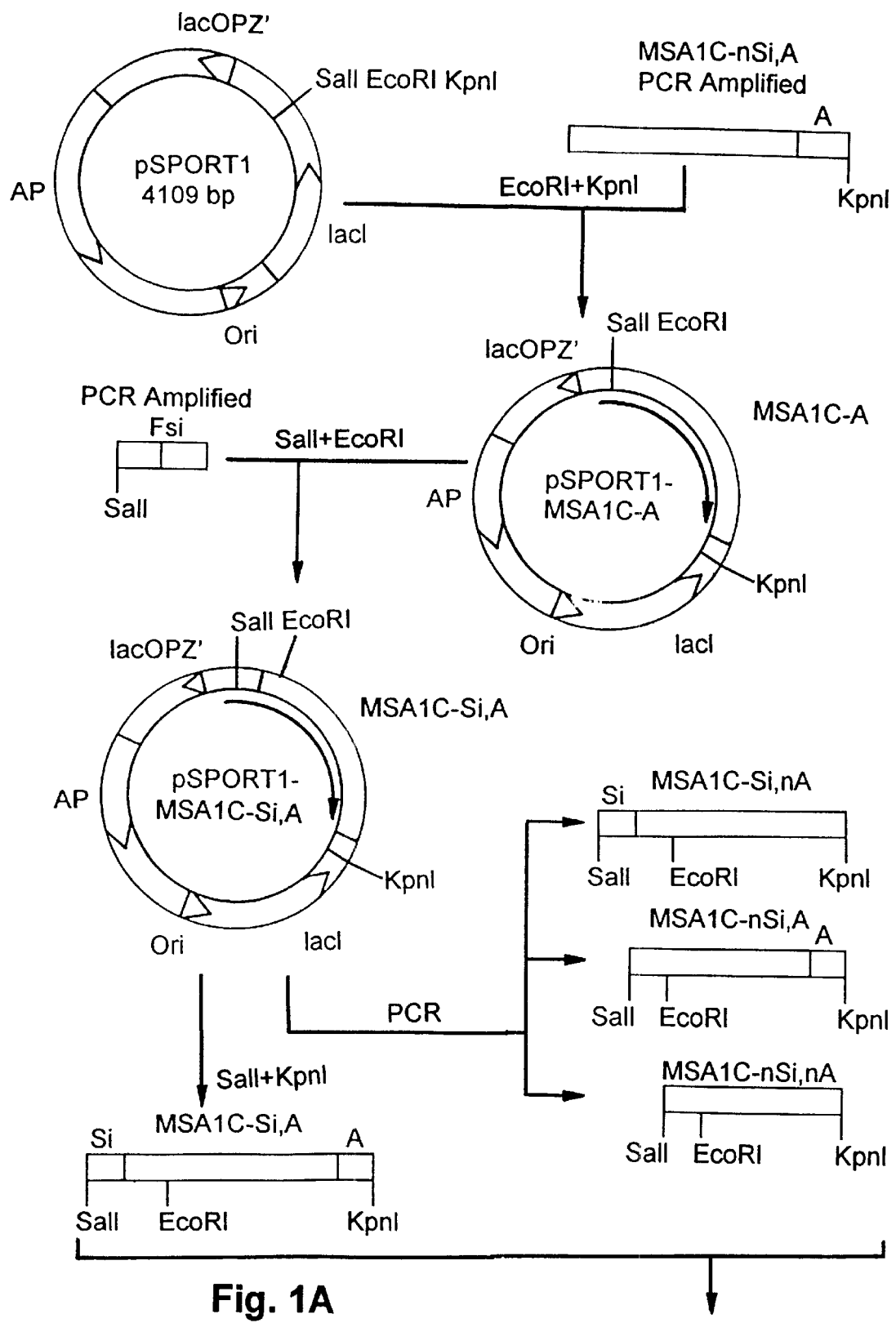

```
ATG AAGATCATAT TCTTTTTATG TTCATTTCTT TTTTTTATTA TAAATACACA
ATGTGTAACA CATGAAAGTT ATCAAGAACT TGTCAAAAAA CTAGAAGCTT TAGAAGATGC
AGTATTGACA GGTTATAGTT TATTTCAAAA GGAAAAAATG GTATTAAATG
AATTGAATTC ACTTAATAAC CCAAAGCATG TATTACAAAA CTTTTCTGTT
TTCTTTAACA AAAAAAAAGA AGCTGAAATA GCAGAAACTG AAAACACATT
AGAAAACACA AAAATATTAT TGAAACATTA TAAAGGACTT GTTAAATATT
ATAATGGTGA ATCATCTCCA TTAAAAACTT TAAGTGAAGA ATCAATTCAA
ACAGAAGATA ATTATGCCAG TTTAGAAAAC TTTAAAGTAT TAAGTAAATT
AGAAGGAAAA TTAAAGGATA ATTTAAATTT AGAAAAGAAA AAATTATCAT
ACTTATCAAG TGGATTACAT CATTTAATTG CTGAATTAAA AGAAGTAATA
AAAAATAAAA ATTATACAGG TAATTCTCCA AGTGAAAATA ATACGGATGT
TAACAATGCA TTAGAATCTT ACAAAAAATT TCTCCCAGAA GGAACAGATG
TTGCAACAGT TGTAAGTGAA AGTGGATCCG ACACATTAGA ACAAAGTCAA
CCAAAGAAAC CAGCATCAAC TCATGTAGGA GCAGAGTCTA ACACAATAAC
AACATCACAA AATGTCGATG ATGAAGTAGA TGACGTAATC ATAGTACCTA
TATTTGGAGA ATCCAAGAA GATTATGATG ATTTAGGACA AGTAGTAACA
GGAGAAGCAG TAACTCCTTC CGTAATTGAT AACATACTTT CTAAAATTGA
AAATGAATAT GAGGTTTTAT ATTTAAAACC TTTAGCAGGT GTTTATAGAA
GTTTAAAAAA ACAATTAGAA AATAACGTTA TGACATTTAA TGTTAATGTT
AAGGATATTT TAAATTCACG ATTTAATAAA CGTGAAAATT TCAAAAATGT
TTTAGAATCA GATTTAATTC CATATAAAGA TTTAACATCA AGTAATTATG
TTGTCAAAGA TCCATATAAA TTTCTTAATA AAGAAAAAAG AGATAAATTC
TTAAGCAGTT ATAATTATAT TAAGGATTCA ATAGATACGG ATATAAATTT
TGCAAATGAT GTTCTTGGAT ATTATAAAAT ATTATCCGAA AAATATAAAT
CAGATTTAGA TTCAATTAAA AAATATATCA ACGACAAACA AGGTGAAAAT
GAGAAATACC TTCCCTTTTT AAACAATATT GAGACCTTAT ATAAAACAGT
TAATGACAAA ATTGATTTAT TTGTAATTCA TTTAGAAGCA AAAGTTCTAA
ATTATACATA TGAGAAATCA AACGTAGAAG TTAAAATAAA AGAACTTAAT
TACTTAAAAA CAATTCAAGA CAAATTGGCA GATTTTAAAA AAAATAACAA
TTTCGTTGGA ATTGCTGATT TATCAACAGA TTATAACCAT AATAACTTAT
TGACAAAGTT CCTTAGTACA GGTATGGTTT TTGAAAATCT TGCTAAAACC
GTTTTATCTA ATTTACTTGA TGGAAACTTG CAAGGTATGT TAAACATTTC
ACAACACCAA TGCGTAAAAA AACAATGTCC ACAAAATTCT GGATGTTTCA
GACATTTAGA TGAAAGAGAA GAATGTAAAT GTTATTAAA TTACAAACAA
GAAGGTGATA AATGTGTTGA AAATCCAAAT CCTACTTGTA ACGAAAATAA
TGGTGGATGT GATGCAGATG CCAAATGTAC CGAAGAAGAT TCAGGTAGCA
ACGGAAAGAA AATCACATGT GAATGTACTA AACCTGATTC TTATCCACTT
TTCGATGGTA TTTTCTGCAG TTCCTCTAAC TTCTTAGGAA TATCATTCTT
ATTAATACTC ATGTTAATAT TATACAGTTT CATTTAA
```

Fig. 2

GENE SEQUENCE OF MSA1C-(Si,nA)

```
ATG  AAGATCATAT TCTTTTTATG TTCATTTCTT TTTTTTATTA TAAATACACA
ATGTGTAACA CATGAAAGTT ATCAAGAACT TGTCAAAAAA CTAGAAGCTT TAGAAGATGC
AGTATTGACA GGTTATAGTT TATTTCAAAA GGAAAAAATG GTATTAAATG
AATTGAATTC ACTTAATAAC CCAAAGCATG TATTACAAAA CTTTTCTGTT
TTCTTTAACA AAAAAAAAGA AGCTGAAATA GCAGAAACTG AAAACACATT
AGAAAACACA AAAATATTAT TGAAACATTA TAAAGGACTT GTTAAATATT
ATAATGGTGA ATCATCTCCA TTAAAAACTT TAAGTGAAGA ATCAATTCAA
ACAGAAGATA ATTATGCCAG TTTAGAAAAC TTTAAAGTAT TAAGTAAATT
AGAAGGAAAA TTAAAGGATA ATTTAAATTT AGAAAAGAAA AAATTATCAT
ACTTATCAAG TGGATTACAT CATTTAATTG CTGAATTAAA AGAAGTAATA
AAAAATAAAA ATTATACAGG TAATTCTCCA AGTGAAAATA ATACGGATGT
TAACAATGCA TTAGAATCTT ACAAAAAATT TCTCCCAGAA GGAACAGATG
TTGCAACAGT TGTAAGTGAA AGTGGATCCG ACACATTAGA ACAAAGTCAA
CCAAAGAAAC CAGCATCAAC TCATGTAGGA GCAGAGTCTA ACACAATAAC
AACATCACAA AATGTCGATG ATGAAGTAGA TGACGTAATC ATAGTACCTA
TATTTGGAGA ATCCGAAGAA GATTATGATG ATTTAGGACA AGTAGTAACA
GGAGAAGCAG TAACTCCTTC CGTAATTGAT AACATACTTT CTAAAATTGA
AAATGAATAT GAGGTTTTAT ATTTAAAACC TTTAGCAGGT GTTTATAGAA
GTTTAAAAAA ACAATTAGAA AATAACGTTA TGACATTTAA TGTTAATGTT
AAGGATATTT TAAATTCACG ATTTAATAAA CGTGAAAATT TCAAAAATGT
TTTAGAATCA GATTTAATTC CATATAAAGA TTTAACATCA AGTAATTATG
TTGTCAAAGA TCCATATAAA TTTCTTAATA AAGAAAAAAG AGATAAATTC
TTAAGCAGTT ATAATTATAT TAAGGATTCA ATAGATACGG ATATAAATTT
TGCAAATGAT GTTCTTGGAT ATTATAAAAT ATTATCCGAA AAATATAAAT
CAGATTTAGA TTCAATTAAA AAATATATCA ACGACAAACA AGGTGAAAAT
GAGAAATACC TTCCCTTTTT AAACAATATT GAGACCTTAT ATAAAACAGT
TAATGATAAA ATTGATTTAT TTGTAATTCA TTTAGAAGCA AAAGTTCTAA
ATTATACATA TGAGAAATCA AACGTAGAAG TTAAAATAAA AGAACTTAAT
TACTTAAAAA CAATTCAAGA CAAATTGGCA GATTTAAAA AAAATAACAA
TTTCGTTGGA ATTGCTGATT TATCAACAGA TTATAACCAT AATAACTTAT
TGACAAAGTT CCTTAGTACA GGTATGGTTT TTGAAAATCT TGCTAAAACC
GTTTTATCTA ATTTACTTGA TGGAAACTTG CAAGGTATGT TAAACATTTC
ACAACACCAA TGCGTAAAAA AACAATGTCC ACAAAATTCT GGATGTTTCA
GACATTTAGA TGAAAGAGAA GAATGTAAAT GTTTATTAAA TTACAAACAA
GAAGGTGATA AATGTGTTGA AAATCCAAAT CCTACTTGTA ACGAAAATAA
TGGTGGATGT GATGCAGATG CCAAATGTAC CGAAGAAGAT TCAGGTAGCA
ACGGAAAGAA AATCACATGT GAATGTACTA AACCTGATTC TTATCCACTT
TTCGATGGTA TTTTCTGCAG TTCCTCTAAC TAA
```

Fig. 3

GENE SEQUENCE OF MSA1C-(nSi,A)

```
ATGGTAACA  CATGAAAGTT  ATCAAGAACT  TGTCAAAAAA  CTAGAAGCTT  TAGAAGATGC
AGTATTGACA  GGTTATAGTT  TATTTCAAAA  GGAAAAAATG  GTATTAAATG
AATTGAATTC  ACTTAATAAC  CCAAAGCATG  TATTACAAAA  CTTTTCTGTT
TTCTTTAACA  AAAAAAAGA   AGCTGAAATA  GCAGAAACTG  AAAACACATT
AGAAAACACA  AAAATATTAT  TGAAACATTA  TAAAGGACTT  GTTAAATATT
ATAATGGTGA  ATCATCTCCA  TTAAAAACTT  TAAGTGAAGA  ATCAATTCAA
ACAGAAGATA  ATTATGCCAG  TTTAGAAAAC  TTTAAAGTAT  TAAGTAAATT
AGAAGGAAAA  TTAAAGGATA  ATTTAAATTT  AGAAAAGAAA  AAATTATCAT
ACTTATCAAG  TGGATTACAT  CATTTAATTG  CTGAATTAAA  AGAAGTAATA
AAAAATAAAA  ATTATACAGG  TAATTCTCCA  AGTGAAAATA  ATACGGATGT
TAACAATGCA  TTAGAATCTT  ACAAAAAATT  TCTCCCAGAA  GGAACAGATG
TTGCAACAGT  TGTAAGTGAA  AGTGGATCCG  ACACATTAGA  ACAAAGTCAA
CCAAAGAAAC  CAGCATCAAC  TCATGTAGGA  GCAGAGTCTA  ACACAATAAC
AACATCACAA  AATGTCGATG  ATGAAGTAGA  TGACGTAATC  ATAGTACCTA
TATTTGGAGA  ATCCGAAGAA  GATTATGATG  ATTTAGGACA  AGTAGTAACA
GGAGAAGCAG  TAACTCCTTC  CGTAATTGAT  AACATACTTT  CTAAAATTGA
AAATGAATAT  GAGGTTTTAT  ATTTAAAACC  TTTAGCAGGT  GTTTATAGAA
GTTTAAAAAA  ACAATTAGAA  AATAACGTTA  TGACATTTAA  TGTTAATGTT
AAGGATATTT  TAAATTCACG  ATTTAATAAA  CGTGAAAATT  TCAAAAATGT
TTTAGAATCA  GATTTAATTC  CATATAAAGA  TTTAACATCA  AGTAATTATG
TTGTCAAAGA  TCCATATAAA  TTTCTTAATA  AAGAAAAAAG  AGATAAATTC
TTAAGCAGTT  ATAATTATAT  TAAGGATTCA  ATAGATACGG  ATATAAATTT
TGCAAATGAT  GTTCTTGGAT  ATTATAAAAT  ATTATCCGAA  AAATATAAAT
CAGATTTAGA  TTCAATTAAA  AAATATATCA  ACGACAAACA  AGGTGAAAAT
GAGAAATACC  TTCCCTTTTT  AAACAATATT  GAGACCTTAT  ATAAAACAGT
TAATGATAAA  ATTGATTTAT  TTGTAATTCA  TTTAGAAGCA  AAAGTTCTAA
ATTATACATA  TGAGAAATCA  AACGTAGAAG  TTAAAATAAA  AGAACTTAAT
TACTTAAAAA  CAATTCAAGA  CAAATTGGCA  GATTTTAAA   AAAATAACAA
TTTCGTTGGA  ATTGCTGATT  TATCAACAGA  TTATAACCAT  AATAACTTAT
TGACAAAGTT  CCTTAGTACA  GGTATGGTTT  TTGAAAATCT  TGCTAAAACC
GTTTTATCTA  ATTTACTTGA  TGGAAACTTG  CAAGGTATGT  TAAACATTTC
ACAACACCAA  TGCGTAAAAA  AACAATGTCC  ACAAAATTCT  GGATGTTTCA
GACATTTAGA  TGAAAGAGAA  GAATGTAAAT  GTTATTAAA   TTACAAACAA
GAAGGTGATA  AATGTGTTGA  AAATCCAAAT  CCTACTTGTA  ACGAAAATAA
TGGTGGATGT  GATGCAGATG  CCAAATGTAC  CGAAGAAGAT  TCAGGTAGCA
ACGGAAAGAA  AATCACATGT  GAATGTACTA  AACCTGATTC  TTATCCACTT
TTCGATGGTA  TTTTCTGCAG  TTCCTCTAAC  TTCTTAGGAA  TATCATTCTT
ATTAATACTC  ATGTTAATAT  TATACAGTTT  CATTTAA
```

Fig. 4

GENE SEQUENCE OF MSA1C-(nSi,nA)

```
ATGGTAACA CATGAAAGTT ATCAAGAACT TGTCAAAAAA CTAGAAGCTT TAGAAGATGC
AGTATTGACA GGTTATAGTT TATTTCAAAA GGAAAAAATG GTATTAAATG
AATTGAATTC ACTTAATAAC CCAAAGCATG TATTACAAAA CTTTTCTGTT
TTCTTTAACA AAAAAAAAGA AGCTGAAATA GCAGAAACTG AAAACACATT
AGAAAACACA AAAATATTAT TGAAACATTA TAAAGGACTT GTTAAATATT
ATAATGGTGA ATCATCTCCA TTAAAAACTT TAAGTGAAGA ATCAATTCAA
ACAGAAGATA ATTATGCCAG TTTAGAAAAC TTTAAAGTAT TAAGTAAATT
AGAAGGAAAA TTAAAGGATA ATTTAAATTT AGAAAAGAAA AAATTATCAT
ACTTATCAAG TGGATTACAT CATTTAATTG CTGAATTAAA AGAAGTAATA
AAAAATAAAA ATTATACAGG TAATTCTCCA AGTGAAAATA ATACGGATGT
TAACAATGCA TTAGAATCTT ACAAAAAATT TCTCCCAGAA GGAACAGATG
TTGCAACAGT TGTAAGTGAA AGTGGATCCG ACACATTAGA ACAAAGTCAA
CCAAAGAAAC CAGCATCAAC TCATGTAGGA GCAGAGTCTA ACACAATAAC
AACATCACAA AATGTCGATG ATGAAGTAGA TGACGTAATC ATAGTACCTA
TATTTGGAGA ATCCGAAGAA G?TTATGATG ATTTAGGACA AGTAGTAACA
GGAGAAGCAG TAACTCCTTC CGTAATTGAT AACATACTTT CTAAAATTGA
AAATGAATAT GAGGTTTTAT N?TTAAAACC TTTAGCAGGT GTTTATAGAA
GTTTAAAAAA ACAATTAGAA ,,?TAACGTTA TGACATTTAA TGTTAATGTT
AAGGATATTT TAAATTCACG ATTTAATAAA CGTGAAAATT TCAAAAATGT
TTTAGAATCA GATTTAATTC CATATAAAGA TTTAACATCA AGTAATTATG
TTGTCAAAGA TCCATATAAA TTTCTTAATA AAGAAAAAAG AGATAAATTC
TTAAGCAGTT ATAATTATAT TAAGGATTCA ATAGATACGG ATATAAATTT
TGCAAATGAT GTTCTTGGAT ATTATAAAAT ATTATCCGAA AAATATAAAT
CAGATTTAGA TTCAATTAAA AAATATATCA ACGACAAACA AGGTGAAAAT
GAGAAATACC TTCCCTTTTT AAACAATATT GAGACCTTAT ATAAAACAGT
TAATGATAAA ATTGATTTAT TTGTAATTCA TTTAGAAGCA AAAGTTCTAA
ATTATACATA TGAGAAATCA AACGTAGAAG TTAAAATAAA AGAACTTAAT
TACTTAAAAA CAATTCAAGA CAAATTGGCA GATTTTAAAA AAAATAACAA
TTTCGTTGGA ATTGCTGATT TATCAACAGA TTATAACCAT AATAACTTAT
TGACAAAGTT CCTTAGTACA GGTATGGTTT TTGAAAATCT TGCTAAAACC
GTTTTATCTA ATTTACTTGA TGGAAACTTG CAAGGTATGT TAAACATTTC
ACAACACCAA TGCGTAAAAA AACAATGTCC ACAAAATTCT GGATGTTTCA
GACATTTAGA TGAAAGAGAA GAATGTAAAT GTTTATTAAA TTACAAACAA
GAAGGTGATA AATGTGTTGA AAATCCAAAT CCTACTTGTA ACGAAAATAA
TGGTGGATGT GATGCAGATG CCAAATGTAC CGAAGAAGAT TCAGGTAGCA
ACGGAAAGAA AATCACATGT GAATGTACTA AACCTGATTC TTATCCACTT
TTCGATGGTA TTTTCTGCAG TTCCTCTAAC TAA
```

Fig. 5 rV-MSA1C-(Si,A)

| TKL | A | | Si | LacZ | TKR | rV-MSA1C-(Si,nA)

| TKL | | Si | LacZ | TKR | rV-MSA1C-(nSi,nA)

| TKL | | LacZ | TKR | rV-MSA1C-(nSi,A)

| TKL | A | | LacZ | TKR |

Fig. 6

MALARIA VACCINE BASED UPON THE ADDITION OF A MSA1 PEPTIDE

RELATED APPLICATIONS

This application is a §371 of international application PCT/US97/01395 filed on Jan. 29, 1996, which is a continuation-in-part application of Ser. No. 08/593,006, filed Jan. 29, 1996, now abandoned.

FIELD OF THE INVENTION

The present invention relates to novel DNA constructs comprising a vector linked to a DNA segment which encodes a protein containing a signal protein at its N-terminus and an anchor sequence at its C-terminus.

More particularly, the present invention relates to vaccines which are useful for the prevention and treatment of malaria caused by *Plasmodium falciparum* in humans.

This work was supported by a DARPA grant. The government retains certain rights in the invention.

BACKGROUND OF THE INVENTION

Preventing or treating malaria has long been a challenging health problem, particularly in developing countries, and the rapid development of drug resistance in the parasite has enhanced the need for the development of a malaria vaccine. Although there has been steady progress over the last decade, several problems still must be overcome, including selection of an appropriate delivery system vehicle and antigen carrier.

Although malaria was believed to have subsided after World War II, recent outbreaks suggest that the disease is on the rise. Malaria is again the leading cause of morbidity/mortality globally and presents an increasing threat in at risk environments. Estimates are that 300 million new cases of malaria occur each year, with mortality of approximately 1% of infected individuals. Prophylactic medications used to prevent the disease have been rendered ineffective by the emergence of drug-resistant strains of the parasite worldwide. Complete vector protection is simply not possible and all attempts to eradicate the relevant species of mosquito have failed.

Four species of *protozoa* of the genus Plasmodium are found in man. The four species include: *Plasmodium vivax, Plasmodium malariae, Plasmodium falciparum* and *Plasmodium ovale*. Of these, *Plasmodium falciparum* produces the most pathogenic of the malarias and often results in death. It is responsible for about half of the human cases of malaria found worldwide.

In malaria, the disease is such that infection followed by recovery does not confer meaningful protection to the individual despite a significant antibody response to several of the parasite proteins. The conventional wisdom has been that the parasite either does not possess antigens suitable for the development of a protective response or has evolved mechanisms which allow it to escape the host immune system. Because recent evidence has shown that immune protection is possible using irradiated sporozoites, the latter hypothesis described above is the more reasonable explanation.

The life cycle of the malaria parasite provides several stages at which interference could lead to cessation of the infective process. Included among these stages is the invasion of the erythrocyte by the merozoite. The merozoite represents a potentially attractive target (and perhaps the only target) from which a vaccine may be produced, because the free merozoite, although it has a limited lifetime (one to two hours) occurs earlier in the life cycle of malaria, and the emergence of later stage sexual forms, which are responsible for transmission of the disease, depends upon the erythrocytic stage.

The general life cycle of malaria parasites is the same for human and other animal malaria parasites, thus allowing model studies to be conducted on a rodent species with accurate translation to the human parasite. For example, the rodent malaria parasite strain *Plasmodium berghei* Anka has a pathology very similar to the FCR-3 strain of *Plasmodium falciparum* (a well studied variant of the human parasite). In addition, the blood stage of the human parasite can be grown in the laboratory (in human red cells) thus affording a system for studying the effects of antibodies/inhibitors on the invasion process, and the erythrocytic phase.

In the life cycle of the malaria parasite, a human becomes infected with malaria from the bite of a female Anopheles mosquito. The mosquito inserts its probe into a host and in so doing, injects a sporozoite form of *Plasmodium falciparum*, present in the saliva of the mosquito.

The sporozoites which have been injected into the human host are cleared into a number of host tissue cells, including liver parenchyma cells (hepatocytes) and macrophages. This phase is known as the exoerythrocytic cycle because at this point in the life cycle the organism has not yet entered red blood cells. After entering hepatocytes, sporozoites undergo a transformation into trophozoites, which incubate and undergo schizogony, rupture and liberate tissue merozoites. This process takes approximately 7–10 days and, depending upon species, may repeat itself several times, during which time the host feels no effects. In *Plasmodium falciparum*, this repetition does not occur. After the incubation period, the liver or other tissue cells burst open and release numerous merozoites into the bloodstream.

Shortly thereafter, certain of these blood borne merozoites invade red blood cells, where they enter the erythrocytic phase of the life cycle. Within the red blood cells, young plasmodia have a red nucleus and a ring-shaped, blue cytoplasm. The plasmodium divides into merozoites, which may break out of the red blood cell, enter other erythrocytes and repeat the multiplication process. This period lasts approximately 48 hours.

During this same 48 hour period of the erythrocytic cycle, male and female gametocytes are formed in the red blood cells. These gametocytes also burst out of the red blood cells along with the merozoites. It is during this period that the human host experiences the symptoms associated with malaria. The merozoites which burst forth from the red blood cells live for only a few hours in the bloodstream. The gametocytes live for several days or more in the host's bloodstream.

The gametocytes are capable of mating only in the mosquito. Thus, in order for *Plasmdium falciparium* to produce sporozoites for infecting a second human host, a mosquito must first bite a human host carrying gametocytes. These gametocytes mature into macrogametes, mate in the mosquito's stomach and produce a zygote. The zygote (ookinete) is active and moves through the stomach or the midgut wall. Under the lining of the gut, the ookinete becomes rounded and forms a cyst called an oocyst, in which hundreds of sporozoites develop. Sporozoites thereafter invade the entire mosquito and many of them enter the salivary glands where they are in a favorable position to infect the next host when the mosquito feeds on its blood. The life cycle thereafter simply repeats itself in another human host.

During the life cycle of *Plasmdium falciparium*, inhibition of invasion of the erythrocyte by the merozoite may be a key to developing an effective vaccine for malaria. Once the parasite has gained entry into the red cell, exposure to the immune system is gone.

In the past, live vaccinia virus was used as a vaccine to eradicate smallpox successfully, and a recombinant vaccinia virus expressing viral antigens has been shown to induce a strong antibody response in immunized animals, conferring protection against disease (Arita, I., *Nature*, 1979, 279, 293–298). Furthermore, it has been shown in animal models that co-presentation of potential immunogens with highly immunogenic vaccinia virus proteins can elicit a strong immune response against that specific immunogen (Moss and Flexner, *Annals of the New York Academy of Sciences*, 86–103; Mackett and Smith, *J. Gen. Virol.*, 1986, 67, 2067–2082; Houard, et al., *J. Gen. Virol.*, 1995, 76, 421–423; Fujii, et al., *J. Gen. Virol.*, 1994, 75, 1339–1344; Rodrigues, et al. *J. Immunol.*, 1994, 153, 4636–4648). Therefore, the utilization of live recombinant vaccinia virus as a vaccine might overcome many problems of antigen expression and delivery presently encountered in the preparation of recombinant proteins in *E. coli*, yeast or insect expression systems. A panel of transfer vectors have been constructed that allow insertion of foreign genes into several sites within the 180 kb vaccinia virus genome (Earl and Moss, *Current Protocols in Molecular Biology*, 1993, 16.17.1–16.17.16). Also, it has been reported that >25 kb of foreign DNA can be inserted into the vaccinia virus genome (Smith and Moss, *Gene*, 1983, 25, 21–28). The correct processing (Chakrabarta, et al., *Nature*, 1986, 320, 535–537) and the appropriate post-translational modification (Hu, et al., *Nature*, 1986, 320, 537–540; Ball, et al., *Proc. Natl. Acad. Sci. USA*, 1986, 83, 246–250; de la Salle, et al., *Nature*, 1985, 316, 268–270), transport and secretion (Ball, et al., *Proc. Natl. Acad. Scienc. USA*, 1986, 83, 246–250 and Langford, et al., *Mol. Cell. Biol.* 1986, 6, 3191–3199) are dictated by the primary structure of the expressed protein. In addition, a recombinant vaccinia virus vaccine has the advantage of being relatively inexpensive and easily stored, transported and delivered, features which are particularly important in the developing countries where malaria is most prevalent.

Proteins on the surface of merozoites are good targets for an immune response and are good malaria vaccine candidates because merozoites are the only stage in the asexual blood cycle in which the parasite is exposed to the immune system. The 190 kD glycoprotein of Plasmodium falciparum, precursor to major merozoite surface antigen1 (MSA1), which is synthesized during schizogony, is considered a promising candidate for a blood-stage malaria vaccine (Blackman, et al., *Mol. Biochem. Parasitol.*, 1991, 49, 29–34; Perrin, et al., *J. Exp. Med.*, 1984, 160, 441–451; Siddiqui, et al., *Proc. Natl. Acad. Sci. USA*, 1987, 84, 3014–3018; Perrin, et al., *Immunol. Rev.*, 1982, 61, 245–269). The high-molecular weight precursor is processed into 88 kD, 30 kD, 38 kD and 42 kD fragments which remain as complexes on the merozoite surface (Holder, et al., *Parasitology*, 1987, 94, 199–208; McBride and Heidrich, *Mol. Biochem. Parsitol.*, 1987, 23, 71–84). The complex is released from the membrane by cleavage of the 42 kD anchor fragment, and a 19 kD carboxyl-terminal fragment remains on the merozoite membrane and is carried into the invaded erythrocytes (Blackman, et al., supra; Blackman, et al., *Mol. Biochem. Parasitol.*, 1991, 49, 35–44). The complete MSA1 of unprocessed *P. falciparum* has been used to provide partial or complete protection against challenge infection (Blackman, et al., *Mol. Biochem. Parasitol.*, 1991, 49, 29–34; Perrin, et al., *J. Exp. Med.*, 1984, 160, 441–451; Siddiqui, et al., *Proc. Natl. Acad. Sci. USA*, 1987, 84, 3014–3018), and it is highly immunogenic in humans (Perrin, et al., *Immunol. Rev.*, 1982, 61, 245–269). Rabbit antibody against the C-terminal processing fragment of MSA1, as expressed in baculovirus, strongly inhibits parasite growth in vitro. These antibodies were able to inhibit homologous and heterologous parasites with similar degrees of efficiency (Hui, et al., *Infect. Imm.*, 1993, 61, 3403–3411).

In prior work at Georgetown University, a series of monoclonal antibodies (mAbs) directed against glycophorin A, the putative erythrocyte receptor for *P. falciparum* were prepared. One of these mAbs, designated 2B10 is capable of blocking the binding of MSA1 to human erythrocytes and inhibiting the invasion of *P. falciparum* merozoites into human erythrocytes (Su, et al. *Infect. Imm.*, 1993, 151, 2309). The anti-idiotype antibody of 2B10 recognized the C-terminal (1047–1640aa) region of MSA1 in a western blot (Su, et al., *J. Immunol.*, 1995) and appears to recognize the same site on glycophorin A as the merozoite.

SUMMARY OF THE INVENTION

The present invention relates to a malaria vaccine comprising an expression vector, preferably, a vaccinia virus system which expresses a protein corresponding substantially to a specific domain of the major merozoite surface antigen 1 (MSA1) of *Plasmodium falciparum* or an immunogenic peptide portion thereof.

In this preferred vaccinia virus system, the DNA coding for the MSA1 protein domain is expressed by the vaccinia virus after administration to a patient. The MSA1 protein or sub-fragment which is then expressed in the patient raises a humoral and/or cell-mediated response to the merozoite malaria antigen, which response provides the effect of protecting the vaccinated patient from a subsequent malaria infection. In preferred embodiments according to the present invention, the vaccinia virus system continues to express antigen in the patient for a period of days, months or even years, thus reinforcing the immunogenic response of the patient to the expressed antigen.

The MSA1 peptide antigen or immunogenic peptide portion thereof which is expressed by the expression vector vaccinia virus may also comprise a signal peptide and/or an anchor peptide sequence. It has been found that the addition of a signal and/or anchor peptide to the expressed MSA1 antigen in vaccines according to the present invention unexpectedly enhances the immunogenicity to the patient of the MSA1 protein of *Plasmodium falciparum*. It is an unexpected result that the inclusion of a signal and/or anchor protein with MSA1 can be expressed by a vaccinia virus system according to the present invention and the expressed peptide will produce a significantly greater immunogenic response than the MSA1 peptide alone or in combination with an adjuvant. It is also an unexpected result that the inclusion of a signal and anchor sequence in the MSA1 peptide sequence expressed by the vaccinia virus will produce an immunogenic response which may be as much as 100 fold greater than the immnogenic response which is produced by the MSA1 peptide which does not contain a signal or anchor peptide sequence.

Methods of inducing an immunogenic response in a patient are also contemplated by the present invention. In this method, a patient is administered an amount of a vaccinia virus capable of expressing the MSA1 peptide of

*Plasmodium falciparum* such that the patient develops an immunogenic response to the expressed peptide. The immunogenic response generated preferably will be "substantially protective", i.e., will protect the patient from some of the more severe symptoms and physiological states of the malaria disease, including the death of the patient from malaria.

The present invention also relates to an immunogenic dosage form as a vaccine, for inducing an immunogenic response to the merozoite stage in the life cycle of *Plasmodium falciparum*. Methods of vaccinating a patient against a malaria infection are also contemplated by the present invention. In this method, a patient is vaccinated against a *Plasmodium falciparum* infection by administering an immunogenic response producing effective amount of a vaccinia virus capable of expressing the MSA1 peptide or an immunogenic peptide portion thereof of *Plasmodium falciparum* in the patient.

The present invention also relates to chimeric proteins or peptides comprising the peptide sequence corresponding to the major merozoite surface antigen 1 (MSA1) of *Plasmodium falciparum* or an immugenic peptide portion thereof in combination with a signal sequence and/or anchor sequence, more preferably both a signal sequence and an anchor sequence.

DESCRIPTION OF THE FIGURES

FIGS. 1A and 1B show a diagrammatic representation of the construction of recombinant vaccinia viruses incorporating the sequences corresponding to MSA1C-(Si,A), MSA1C-(Si,nA), MSA1C-(nSi,A) and MSA1C-(nSi,nA).

FIGS. 2–5 represent the gene sequences for MSA1C-(Si, A), MSA1C-(Si,nA), MSA1C-(nSi,A) and MSA1C-(nSi, nA).

FIG. 6 is a diagrammatic representation of four recombinant vaccinia viruses of the present invention: rv-MSA1-(Si,A); rv-MSA1-(Si,nA); rv-MSA1-(nSi,A); rv-MSA1-(nSi,nA). This figure shows the schematic of the genome of recombinant vaccinia viruses expressing the different MSA1 constructs. $Tk_l$ and $TK_R$, right and left regions of the vaccinia virsu thymidine kinase gene; LacZ, beta-galacosidase gene. Si: signal region of MSA1; nSi: no signal region of MSA1; A: anchor region of MSAa1; nA: no anchor region.

FIG. 7 is a diagrammatic representation of the results obtained from Western blot analysis of recombinant vaccinia virus expressed proteins using anti-MSA1C-A mouse serum as a probe, of proteins expressed from BSC-1 cells infected with vaccinia virus. A. pellet of rV.V-MSA1C(Si,nA) infected cells; B. supernatant of rV.V-MSA1C(Si,nA) infected cells; C. pellet of rV.V-MSA1C(Si,A) infected cells; D. supernatant of rV.V-MSA1C(Si,A) infected cells; E. pellet of rV.V-MSA1C(nSi,nA) infected cells; F. supernatant of rV.V-MSA1C(nSi,nA) infected cells; G. pellet of rV.V-MSA1C(nSi,A) infected cells; H. supernatant of of rV.V-MSA1C(nSi,A) infected cells; I. pellet of WR infected cells; J. supernatant of WR infected cells.

FIGS. 8A–8J show a diagrammatic representation of results obtained from immunofluorescence staining of non-permeabilized infected cells. HeLa cells seeded on pre-treated coverslips for 48 hours were infected with recombinant and wild-type vaccinia virus at an M.O.I. of 5. The cells were probed with anti-MSA1C-A serum and laveled with FITC goat anti-mouse. A,B: rV.V-MSA1C(Si,nA) infected cells; C,D: rV.V-MSA1C(Si,A) infected cells; E,F: rV.V-MSA1C(nSi,nA) infected cells; G,H: rV.V-MSA1C(nSi,A) infected cells; I,J: WR infected cells.

FIG. 9 is a diagrammatic representation of results obtained in rabbits immunized intradermally with the recombinant vaccinia viruses of the present invention. Five rabbits were immunized intradermally with recombinant and wild-type vaccinia virus, and one rabbit was immunized intravenously with rV-MSA1C-(Si,A). The I.D. immunizations occurred on days 0, 21, 47 and 68, and the I.V. immunizations occurred on days 0, 47 an 68. Blood samples taken on days 33, 54, and 78 were analyzed for antibodies to the trpE-MSA1C-A protein (C-terminus of MSA1 expressed and purified from *E. coli*) using ELISA. Sera were analyzed in duplicate. (+)rV-MSA1C-(Si,A); (Δ)rV-MSA1C-(Si,A); (○)rV-MSA1C-(Si,nA); (X)rV-MSA1C-(nSi,nA); (◇)rV-MSA1C-(nSi,A); (∫)WR.

FIG. 10 is a diagrammatic representation of results obtained in Balb/c mice which were inoculated with vaccinia viruses of the present invention. Balb/c mice were inoculated I.P. with recombinant and wild-type vaccinia virus on days 0, 21, 42 and 63. Blood samples taken on days 11, 31, 51, 73 93, 123, 147, 167 and 187 were analyzed for antibodies to trpE-MSA1C-A protein (C-terminus of MSA1 expressed and purified from *E. coli*) using ELISA. Sera were analyzed in duplicate: (∫) rV-MSA1C-(Si,A); (○) (rV-MSA1C-(Si,nA); (X)(rV-MSA1C-(nSi,A); (◇) (rV-MSA1C-(nSi,nA); (+) WR.

FIG. 11 is a diagrammatic representation of the results obtained from a Western blot analysis of the recognition of a 190 kD of *P. falciparum* by vaccinia virus induced mouse antibodies. Schizont stage parasites were lysed by boiling in sample buffer and loaded onto a 4–20% Tris-glycine gradient gel, and the proteins were transferred to a PVDF membrane by electrophoresis. These blots were then probed with anti-MSA1C-(Si,A), anti-MSA1C-A or anti-WR antibodies and labelled with phosphatase-conjugated goat anti-mouse IgG. A. anti-MSA1C(Si,A); B. anti-MSA1C-A; C. anti-WR.

DETAILED DESCRIPTION OF THE INVENTION

The following terms shall be used throughout the instant specification in an effort to describe the present invention.

The term "chimeric protein", "chimeric peptide" or "chimeric peptide sequence" is used to describe the non-natural peptide sequences according to the present invention which comprise the expressed protein or peptide and an anchor peptide and/or a signal peptide. As noted by the use of this term, chimeric peptides generally are synthetic peptides produced by an expression vector which contain a desired target protein or peptide (either MSA1 or an immunogenic peptide portion thereof) in combination with another peptide sequence (either an anchor or signal peptide sequence).

The term "patient" is used to describe an animal, including a mammal and especially including a human patient which is administered a dosage form of an expression vector or chimeric protein according to the present invention. In the present invention, the expression vector encodes for MSA1 or an immunogenic peptide portion therof and expresses the encoded protein or peptide in the patient.

The term "expression vector" is used to describe the means by which nucleic acid, including DNA, cDNA, RNA or variants thereof, more preferably DNA fragments, encoding for a specific peptide or protein, may be introduced into the patient or the patient's tissue in order to express or produce the desired protein. Such vectors include any vectors into which a nucleic acid sequence encoding for the desired MSA1 protein or immunogenic peptide fragment thereof, anchor peptide sequence and/or, signal protein sequence may be inserted (along with any required or optional operational elements) into a host organism and replicated. Expression vectors may also be used to simply produce chimeric peptide in culture for isolation. Preferred vectors are those which are capable of expressing the peptide or protein sequences in mammalian cells and whose restriction sites are well known and which contain the required operational elements for expression of the desired protein or peptide sequence. In the present invention, the vector is preferably a vaccinia virus vector, adenovirus vector or herpes virus vector which has the capacity to infect a mammalian cell and express or synthesize proteins utilizing the host's biosynthetic mechanism. In such cases, the viral vector used for delivery should optimally be one which infects cells but which does not cause lysis due to replication (i.e., an attenuated or partially disabled virus selected from among adenovirus, vaccinia virus and herpes viruses, among similar types).

According to the vector approach in the present invention, the vector will infect the host cells and, using the host cells' biosynthetic pathways, synthesize encoded protein or peptide fragment. Any immunizing vehicle which has a detailed genetic and human use history may be used as the expression vector in the present invention. The preferred expression vector is a viral vector, more preferably, a vaccinia virus vector, for example, as described by Earl and Moss, *Current Protocols in Molecular Biology*, 1993, 16.17.1–16.17.16) and Smith and Moss, *Gene*, 1983, 25, 21–28. However, any vaccinia or other viral vector which may be used in the above-described manner may be appropriate for use in the present invention.

In order to express the desired protein or peptide sequence, the expression vector should contain at least one promoter, at least one operator, at least one terminator codon, and any other sequences which are necessary for the efficient transcription and subsequent translation of the nucleic acid from the vector. These operational elements are well known to those of ordinary skill in the art. In preferred embodiments according to the present invention, the expression vectors will advantageously comprise at least one origin of replication which is recognized by the host organism along with at least one selectable marker and at least one promoter sequence capable of initiating transcription of the nucleic acid (preferably, DNA) sequence.

The term "vaccine" is used throughout the specification to describe a preparation intended for active immunological prophylaxis. In the present invention, vaccines comprise an expression vector, preferably a vaccinia virus system which expresses an antigenic protein after administration of the vaccinia virus system to an animal, such as a mammal. Vaccines may also comprise chimeric peptides comprising MSA1 or an immunogenic peptide portion thereof in combination with a signal peptide sequence and/or an anchor peptide sequence. The method of administering the vaccine (s) according to the present invention may vary and include intravenous, buccal, oral, transdermal and nasal, among others, but intramuscular or subcutaneous administration is the most common method of administration.

The term "MSA1 protein" or "MSA1 peptide" is used to describe the major merozoite surface antigen 1 of the merozoite stage of *Plasmodium falciparum* or immunogenic peptide portions thereof. MSA1 is the major surface protein of the merozoite stage of *Plasmodium falciparum*. It is a 190 kD glycoprotein which is synthesized during schizogony life-cycle stage. The high molecular weight precursor is processed into 88 kD, 30 kD, 38 kD and 42 kD fragments which remain as complexes on the merozoite surfaces. The complex is released from the merozoite membrane by cleavage of the 42 kD anchor fragments and a 19 kD carboxy-terminal fragment remains on the merozoite membrane and is carried into the invaded erythrocytes. The complete MSA1 gene sequence is available on the data base UNDP/WORLDBANK/WHO/TDR Malaria Sequence. The preferred portion of MSA1 for expression in the vaccinia virus system according to the present invention is a carboxy-terminal region (corresponding to amino acids 1047 to 1640) of MSA1. In the present invention, the expressed protein may be MSA1 or any portion thereof, preferably such that the MSA1 portion contains at least the carboxy-terminal region of MSA1.

The terms "carboxy-terminal region of MSA1" and "carboxy-terminal MSA1 peptide" are used to describe that portion of the MSA1 protein corresponding to amino acids 1047 to 1640 which is the preferred expressed antigen peptide sequence in the present vaccines. It represents a preferred target for the development of humoral and/or cell mediated response because of the degree of specificity of the immune response which can be elicited against such a protein segment. In the present invention, the expression of the C-terminal MSA1 peptide according to the instant invention produces a specific immune reactivity which becomes less specific as more of the MSA1 protein is incorporated into the vaccinia virus system. In the present invention, the above terms to describe the C-terminal MSA1 peptide include not only the 593 amino acid peptide referred to above, but any peptide substantially corresponding to that 593 amino acid peptide.

The following DNA sequence corresponding to the C-terminus is preferably used in the present invention:

TTGAATTC ACTTAATAAC CCAAAGCATG TATTA-CAAAA CTTTTCTGTT TTCTTTAACA AAAAAAAGA AGCTGAAATA GCAGAAACTG AAAACACATT AGAAAACACA AAAATATTAT TGAAACATTA TAAAGGACTT GTTAAATATT ATAATGGTGA ATCATCTCCA TTAAAAACTT TAAGTGAAGA ATCAATTCAA ACAGAAGATA ATTATGCCAG TTTAGAAAAC TTTAAAGTAT TAAGTAAATT AGAAGGAAAA TTAAAGGATA ATTTAAATTT AGAAAAGAAA AAATTATCAT ACTTATCAAG TGGATTACAT CATTTAATTG CTGAATTAAA AGAAGTAATA AAAAATAAAA ATTATACAGG TAATTCTCCA AGTGAAAATA ATACGGATGT TAACAATGCA TTAGAATCTT ACAAAAAATT TCTCCCAGAA GGAACAGATG TTGCAACAGT TGTAAGTGAA AGTGGATCCG ACACATTAGA ACAAAGTCAA CCAAAGAAAC CAGCATCAAC TCATGTAGGA GCAGAGTCTA ACACAATAAC AACATCACAA AATGTCGATG ATGAAGTAGA TGACGTAATC ATAGTACCTA TATTTGGAGA ATCCGAAGAA GATTATGATG ATTTAGGACA AGTAGTAACA GGAGAAGCAG TAACTCCTTC CGTAATTGAT AACATACTTT CTAAAATTGA AAATGAATAT GAGGTTTTAT ATTTAAAACC TTTAGCAGGT GTTTATAGAA GTTTAAAAAA ACAATTAGAA AATAACGTTA TGACATTTAA TGTTAATGTT AAGGATATTT TAAATTCACG ATTTAATAAA CGTGAAAATT TCAAAAATGT TTTAGAATCA GATTTAATTC CATATAAAGA TTTAACATCA AGTAATTATG TTGTCAAAGA TCCATATAAA TTTCTTAATA AAGAAAAAAG AGATAAATTC TTAAGCAGTT ATAATTATAT TAAGGATTCA ATAGATACGC ATATAAATTT TGCAAATGAT GTTCTTGGAT

ATTATAAAAT ATTATCCGAA AAATATAAAT
CAGATTTAGA TTCAATTAAA AAATATATCA
ACGACAAACA AGGTGAAAAT GAGAAATACC
TTCCCTTTTT AAACAATATT GAGACCTTAT
ATAAAACAGT TAATGATAAA ATTGATTTAT
TTGTAATTCA TTTAGAAGCA AAAGTTCTAA
ATTATACATA TGAGAAATCA AACGTAGAAG
TTAAAATAAA AGAACTTAAT TACTTAAAAA
CAATTCAAGA CAAATTGGCA GATTTTAAAA
AAAATAACAA TTTCGTTGGA ATTGCTGATT
TATCAACAGA TTATAACCAT AATAACTTAT
TGACAAAGTT CCTTAGTACA GGTATGGTTT
TTGAAAATCT TGCTAAAACC GTTTTATCTA
ATTTACTTGA TGGAAACTTG CAAGGTATGT
TAAACATTTC ACAACACCAA TGCGTAAAAA
AACAATGTCC ACAAAATTCT GGATGTTTCA
GACATTTAGA TGAAAGAGAA GAATGTAAAT
GTTTATTAAA TTACAAACAA GAAGGTGATA
AATGTGTTGA AAATCCAAAT CCTACTTGTA
ACGAAAATAA
TGGTGGATGT GATGCAGATG CCAAATGTAC
CGAAGAAGAT TCAGGTAGCA ACGGAAAGAA AAT-
CACATGT GAATGTACTA AACCTGATTC TTATC-
CACTT TTCGATGGTA TTTTCTGCAT TTCCTCTAAC
TTCTTAGGAA TATCATTCTT ATTAATACTC ATGT-
TAATAT TATACAGTTT CATTTAA (Sequence ID. No.1).

The amino acid sequence corresponding to the above-described C-terminus of MSA1 is:

KLNSLNNPKHVLQNFSVFFNKKKEAEI-
AETENTLENTKILLKHYKGLVKYYNGE SSPLK-
TLSEESIQTEDNYASLENFKVLSKLEGKL
KDNLNLEKKKLSYLSSGLHHLIAELKEV
IKNKNYTGNSPSENNTDVNNALESYKK FLPEGT-
DVATVVSESGSDTLEQSQPKKPASTHVGA ESN-
TITTSQNVDDEVDDVIIVPIFGESEEDY-
DDLGQVVTGEAVTPSVIDNILSKIENEYEVL
YLKPLAGVYRSLKKQLENNVMTFNVN-
VKDILNSRFNKRENFKNVLESDLIPY
KDLTSSNYVV KDPYKFLNKEKRDKFLSSYNY-
IKDSIDTDINFANDVLGYYKILSEKYKS-
DLDSIKKYINDKQ GENEKYLPFLNNIETLYK-
TVNDKIDLFVIHLEAKVLNYTYEKSNVEVKIKE
LNYLKTIQDKL ADFKKNNNFVGIADLST-
DYNHNNLLTKFLSTGMVFENLAKTVLSN-
LLDGNLQGMLNISQHQC VKKQCPQNSGCFRHL-
DEREECKCLLNYKQEGDKCVENPNPTCNENN
GGCDADAKCTEEDSGS NGKKITCECTKPDSY
PLFDGIFCSSSNFLGISFLLILMLILYSFI(Sequence ID. No.2).

Any expressed peptide which substantially corresponds to the MSA1 protein or an immunogenic peptide portion of the MSA1 protein and, preferably, also contains a peptide corresponding to at least an immunogenic portion of the C-terminal MSA1 peptide, may be used in the present vaccines. Of course, expressed peptides corresponding to MSA1 protein and/or an immunogenic peptide portion thereof in combination with a signal sequence or anchor sequence may also be used in the present invention.

The term "signal peptide" "signal sequence" or "signal protein" is used to describe a 7–30 unit amino acid peptide sequence, preferably about a 15–26 unit amino acid peptide sequence, which is generally found at or near the N-terminus of the expressed protein or peptide which is used in the present invention in order to substantially enhance the biological activity of the protein or peptide expressed in the patient according to the present invention. Signal sequences generally contain hydrophobic peptide sequences of between about 7 and 30 amino acid units, more preferably, about 15 to 26 amino acid units, even more preferably about 16 to 24 amino acid units and most preferably about 18 to 20 amino acids units appear to be essential for the targeting of protein chains (generally, secretory proteins) to membranes within the cell. These hydrophobic sequences are of sufficient length to cross the lipid bilayer of the cell membranes. Signal sequences serve as organizers for the cellular traffic of macromolecules. These proteins are believed to play a central role in the translocation of polypeptide chains across membranes. In the present invention, the incorporation of a signal protein sequence at the amino terminus of the protein or peptide sequence expressed by the vaccinated patient is associated with the substantial enhancement in the biological activity (including the therapeutic effect of immunogenicity) associated with the expressed protein or peptide. In the present invention, signal sequences which are known in the art may be used in the present invention. For example, although it may be possible to utilize yeast or lower trophic order signal sequences, clearly mammalian signal sequences are preferred for use in mammals and the specific species signal sequences are most preferred for use in the desired mammalian species to be treated. Thus, in providing for an expressed protein or polypeptide in humans, a human signal sequence is most preferred.

Signal sequences for use in the present invention generally contain three regions, a first or c region at the carboxy end of the peptide (which serves as the cleavage site for a signal peptidase enzyyme), comprising about 5 to 7 amino acid residues which tend to be highly polar but uncharged; a second or h region which is N-terminal to the c region, generally about 7 to 13 amino acid residues in length and highly hydrophobic (comprised primarily of Leu, Ala, Met, Val, Ile, Phe, and Trp amino acids, but may contain an occasional Pro, Gly, Ser or Thr amino acid residue); and a third region or n-region of highly variable length and composition, but generally carrying a net positive charge contributed by the N-terminus (negative charges contributed from acidic residues are also known) and any charged residues. Between the c region and the h region are between 1 and 3 amino acid residues which tend to be small and uncharged (Ala, Gly, Ser, others). Synthetic homopolymeric h regions comprised of amino acids selected from the group consisting of leucine, isoleucine, phenylalanine, valine, alanine and tryptophan, preferably leucine, isoleucine and phenylalanine may be used in the signal proteins according to the present invention. See generally, von Heijne, *European Journal of Biochemistry*, (1983), 133, pp. 17–21.

The signal sequences which are used in the present invention preferably encompass eukaryotic signal sequences, preferably between 7 and 30 amino acid units in length, preferably between 15 and 26 units, more preferably between about 16 and 26 amino acids, even more preferably between 18 and 20 amino acid units. In the present invention, the c region of the signal peptide should be more polar and the boundary between the h and c regions between residues −5 and −6, or −7 or −8 (counting from the position of cleavage of the signal sequence- i.e., the first amino acid of the mature or expressed protein or peptide is +1) is between 1 and 3 amino acid residues which tend to be small and uncharged (Ala, Gly, Ser, others). Position preferences in the h/c for amino acids are as follows:

−10 most preferably leucine or alternatively, isoleucine, valine, alanine, or phenylalanine;
−9 most preferably leucine, alternatively, isoleucine, alanine, valine, phenylalanine;
−8 most preferably leucine, alternatively isoleucine, alanine, valine, glycine, phenylalanine;

−7 most preferably alanine, alternatively, leucine, isoleucine, valine, phenylalanine;

−6 most preferably valine, alternatively leucine, valine, isoleucine, phenylalanine, alanine;

−5 most preferably proline, alternatively glycine, alanine, leucine, valine;

−4 most preferably glycine, alternatively proline, leucine, alanine, valine;

−3 most preferably alanine, alternatively valine;

−2 most preferably leucine, alternatively phenylalanine;

−1 most preferably alanine, alternatively glycine.

In the signal sequences used in the present invention, the h region may vary in length as well. The n region is polar, contains positively charged amino acids (predominantly lysine and arginine) and varies with the overall length of the signal peptide as described above. The c region extends from residues −1 to −5 of the signal peptide/expressed or mature protein. In terms of location of the c, h and n regions, the c region is N-terminus to the expressed or mature protein, the h region is N-terminus to c region (with a 1–3 amino acid boundary between the c and h region) and the n region is a positively charged N-terminus to the h region. In sum, the n region is variable in length and generally positively charged (with a preferred charge of +2), the h region is hydrophobic and variable in length and the c region preferably contains about five (5–7) generally polar amino acids.

The end of the hydrophobic domain (i.e., the boundary between the hydrophobic residues enumerated above) should preferably be at positions −6/−5. Overall, the signal sequence should comprise a 5 to 10 unit residue initial sequence (beginning with methionine) followed by at least a seven residue sequence (as described above) and an additional amino acids from 1 to 10 residues in length. A typical sequence for the region noted about is:

ILLLLAV.

The signal sequence used should be characteristic of the cell type used for expression of the protein. Thus, in veterinary applications, the signal sequence most preferably used should be that of the animal to be treated. Often a signal sequence which is mammalian in character is acceptable. Most mammalian signal sequences will have significant efficacy in expressing proteins or peptides in other mammalian cells. Human signal sequences are preferably used for human applications.

In the present invention, the following signal peptide DNA sequences are preferably used:

ATG AAGATCATAT TCTTTTTATG TTCATTTCTT TTTTTTATTA TAAATACACA ATGTG(Sequence ID. No.3);

ATG AAGATCATAT TCTTTTTATG TTCATTTCTT TTTTTTATTA TAAATACACA ATGTGTAACA CAT- GAAAGTT ATCAAGAACT TGTCAAAAAA CTA- GAAGCTT TAGAAGATGC AGTATTGACA GGT- TATAGTT TATTTCAAAA GGAAAAAATG GTATTAAATG AA(Sequence ID. No.5).

The amino acid sequences corresponding to the above-described signal peptide DNA sequences are:

MKIIFFLCSFLFFIINTQC(Sequence ID. No.4); and

MKIIFFLCSFLFFIINTQCVTHESYQELVKKLEALE DAVLTGYSLFQKEKMVLNE(Sequence ID. No.6).

The term "anchor protein" or "anchor peptide sequence" is used to describe proteins or peptides which are anchored to the external surface of the plasma membrane generally by covalent bonding to glycans containing phosphatidyl inositol. These structures to which the anchor protein or peptide is bonded are often referred to as glycosyl phosphatidylinositols or GPIs. In all cells, anchor proteins covalently bonded to GPIs are found on the external face of the plasma membrane of cells or on the lumenal surface of secretory vesicles.

In the present invention an "anchor protein" or "anchor peptide" comprises a peptide sequence preferably of about 15–35 residues in length which is generally expressed at the carboxy-terminus of the protein or peptide expressed by the expression vector according to the present invention (3' end of the DNA sequence expressing the desired protein or peptide and carboxyl terminus of the expressed protein or peptide).

In the present invention, many of the proteins or peptides which are expressed in the patient and in particular, the immunogenic proteins or peptides of vaccines according to the present invention which are expressed in the patients produce a biological or immunogenic response in the patient which is substantially enhanced when an anchor peptide is incorporated at the carboxy terminus of that protein or peptide. The inclusion of a signal protein at or in the proximity of the N-terminus, in addition to the anchor peptide at the carboxy-terminus of the expressed protein, is associated with an unexpected enhancement in the biological effects of the expressed protein. This is especially true where the expressed protein is antigenic or immunogenic in nature.

The carboxy-terminus of the expressed protein or peptide residue is modified by attachment of a glycolipid anchor, which serves to anchor the modified protein or peptide to the cell surface. The peptide residue to which the GPI anchor is added is always one of small amino acids, such as glycine, aspartic acid, asparagine, alanine, serine and cysteine. These occur at the carboxyl terminus of the protein/peptide of interest and thus can be specified by inclusion of the appropriate codons in the DNA fragment to be added to the cDNA sequence specifying the protein/peptide of interest. In addition, the two residues downstream of the anchor addition site are usually small.

The cleavage/anchor addition site resides in a domain of three small amino acid residues, although the central of the three residues has less stringent steric requirements. In order to be certain that functionally or immunologically important amino acids at or near the carboxyl terminus of the protein/peptide target are not compromised, several additional amino acids (preferably, polar ones such as lysine or arginine as well as threonine, alanine and proline) to make up a total of up to 10 residues are inserted in such an orientation so that the small, polar segment is at the carboxyl terminus. The remainder of the addition signal sequence will contain from 15 to 35 amino acids with a hydrophobic domain at the extreme carboxyl terminus. This domain should extend for 15–25 amino acids and will include amino acids such as valine, leucine, isoleucine, alanine, pphenylalanine, but may also contain proline and glycine as well as tryptophan. A typical such sequence is as follows:

TACDLAPPAGTTD(Sequence ID. No.23) AAHPGRSVVPALLPLLAGTLLLLETATAP (Sequence ID. No.24).

The small sequence is in bold face with the left portion represeting the terminus of the protein and the D residue the site of GPI addition. The right hand portion is that cleaved during GPI addition with the underlined sequence indicating the hydrophobic terminus.

In the present invention, the anchor peptide may have a cleavable N-terminal sequence, which directs the peptide to the endoplasmic reticulum and the cellular trafficking pathway where the GPI anchor is added. As described above, the anchor peptide also has a predominantly hydrophobic sequence at the extreme carboxy terminus which generally ranges in size from about 15 to about 35, more preferably about 15 to 30, and even more preferably about 15 to 25 amino acid residues, signals the addition of the GPI anchor and is cleaved off concurrent with GPI addition. It is the hydrophobicity rather than the sequence itself which is important for anchor addition. Essentially any hydrophobic amino acid sequence of at least about 15 to about 35, more preferably about 15 to 30 amino acid residues would be capable of directing the addition of a GPI anchor. Anchor addition is generally a transamidation reaction in which the free ethanolamine amino group of the GPI precursor attacks (by way of nucleophilic addition) a peptide bond at the target amino acid, which becomes the C-terminal amino acid.

Generally, in the expressed anchor peptide sequence, just upstream of the hydrophobic sequence to which the GPI anchor is added is a hydrophilic spacer (usually about 5–10 residues) which contains hydrophilic amino acids. The residue to which the GPI anchor is added (the "anchor addition site") is an amino acid residue within this hydrophilic spacer selected from the group consisting of glycine, aspartic acid, arginine, asparagine, alanine, serine and cysteine. In addition, the two residues downstream from the anchor addition site are also usually small amino acid residues apparently to minimize steric hindrance at the anchor addition site.

Preferably, the GPI portion is preassembled and added as a single unit to a specific amino acid residue near the carboyxl terminus of the expressed protein or peptide. Thus, the carboxyl terminal region may be characterized by the presence of a C-terminal signal peptide which is preferably ten to thirty amino acids in length and provides the information needed to add the GPI anchor. The actual amino acid residue to which the GPI structure is attached is called the omega site and this residue should be glycine, alanine, cysteine, serine, asparagine or aspartic acid. The omega +1 site (towards the carboxyl terminus of the expressed, unprocessed protein) preferably is selected from glycine, alanine, cysteine, serine, asparagine, aspartic acid, glutamate and threonine. The omega +2 site is alanine or glycine. The omega +2 site is followed by a hinge or spacer of ideally 5 to 7 amino acids that preferably contains charged amino acids and proline; this is followed in turn by a preferably hydrophobic sequence of amino acids which terminate the carboxyl signal peptide.

The overall structure of the anchor peptide may be summarized as a 15–35 amino acid peptide at the carboxyl terminus of the expressed protein or peptide. This anchor peptide sequence (reading from the terminus towards the amino end) begins with a hydrophobic stretch of amino acids of variable length, followed by a sequence of preferably 5–7 amino acids which contains charged residues, followed by three amino acids (either glycine or alanine at the omega +2 site); any of glycine, alanine, cysteine, serine, asparagine, aspartic acid, glutamate and threonine at the +1 omega site; and any of glycine, alanine, serine, cysteine, aspartic acid or asparagine at the omega site.

It is noted that in the present invention, while the signal peptide sequence is generally found at the N-terminus (directly at the N-terminus or removed as much as 1,000 or more amino acids from the N-terminus) and the anchor peptide sequence is generally found at the carboxy-terminus of the expressed protein or peptide, the signal peptide may be found at or near the carboxy terminus of the expressed target protein or peptide.

In the present invention, anchor sequences which are known in the art may be used in the present invention. For example, although it may be possible to utilize yeast or lower trophic order anchor sequences, clearly mammalian anchor sequences are preferred for use in mammals and the specific species signal sequences are most preferred for use in the desired mammalian species to be treated. Thus, in providing for an expressed protein or polypeptide in humans, a human anchor sequence is most preferred.

In the present invention, the following anchor peptide DNA sequence is preferably used:

TTCTTAGGAA TATCATTCTT ATTAATACTC ATGTTAATAT TATCCAGTTT CATTTAA(Sequence ID. No.7).

The amino acid sequence corresponding to the above-described anchor peptide DNA sequence is:

FLGISFLLILMLILYSFI(Sequence ID. No.8).

In experiments which evidence the utility of the broader invention, the sequences which appear in FIGS. 2–5 were incorporated into vaccinia virus and were expressed in experimental animals.

It is noted that in the present invention, while the signal peptide sequence is generally found at the N-terminus (directly at the N-terminus or somewhat removed- by as much as 1,000 or more amino acids from the N-terminus) and the anchor peptide sequence is generally found at or in the proximity of the carboxy-terminus of the expressed protein or peptide, the signal peptide may be found at or near the carboxy terminus and the anchor peptide may be found at or near the N-terminus of the expressed target protein or peptide.

The term "effective amount" refers to an amount or concentration of recombinant vaccinia virus effective to produce a protective immune or therapeutic response with respect to the disease malaria. In general, an effective amount of vaccinia virus which is administered to a human patient will vary depending upon a number of factors associated with that patient, including whether the patient previously has been exposed to *Plasmodium falciparum* before. An effective amount of vaccinia virus can be determined by varying the dosage of the product and measuring the resulting cellular and humoral immune and/or therapeutic responses, prior to administration. In general terms, in humans, this amount represents approximately $10^4$ to about $10^7$ plaque forming units, preferably about $1\times10^6$ to about $5\times10^6$ plaque-forming units (determined by assay, as described herein). It is noted that the above described range of administered vaccinia virus is chosen to enhance the likelihood of eliciting an immunogenic response without causing a malaria infection in the vaccine recipient.

In the case where the chimeric peptide is administered instead of the expression vector in order to facilitate an immunogenic response, the amount of chimeric peptide administered will be an amount or concentration of the peptide to produce a protective immune or therapeutic response with respect to the disease malaria. While this amount may vary over a considerably wide range, depending upon the immunogenicity of the chimeric peptide chosen, generally the amount of peptide administered ranges from about 0.01 micrograms (10 nanograms) to about 250 micrograms, more preferably about 0.1 microgram to about 100 micrograms, even more preferably about 1 microgram to about 25 micrograms within this range.

The present invention contemplates, as a preferred embodiment, the incorporation of both a signal peptide and anchor peptide along with the MSA1peptide into the expressed peptide has been found to be particularly advantageous in producing an immunogenic response to the MSA1 peptide. The signal peptide sequence is generally incorporated into the immunogenic peptide at or near the amino end of the MSA1 peptide or related antigenic peptide and the anchor peptide is generally incorporated at or near the carboxyl end of the MSA1 peptide. The immunogenic peptide is expressed by the vaccinia virus accordingly and will contain a signal peptide aequence and/or an anchor peptide sequence. Thus, in the present invention, the signal and anchor peptides are preferably expressed at the amino and carboxy terminus of the expressed MSA1 peptide, respectively. Generally, the signal peptide sequence is located upstream from the MSA1 peptide and the anchor peptide is downstream from the MSA1 peptide.

In the method of preparing vaccinia virus which leads to expression of MSA1 peptide, preferably MSA1 peptide containing a signal and/or anchor peptide, by the vaccine recipient, any method which is capable of incorporating a sequence of DNA containing genetic material for the expression of the MSA1 peptide and optionally, a signal peptide and/or an anchor peptide, may be used. The method which is used in the present invention is well known in the art. Accordingly, in the present invention, a DNA sequence containing the genetic code for the MSA1 peptide to be expressed is obtained by chemical synthesis or other means such as biochemical isolation of available MSA1 DNA sequences and incorporated into a cloning plasmid (for example following cloning vectors: pBR322, pGEM3z, pSP70, pSE420, pRSET, lambdaZAP, all commercially available, among numerous others). The appropriate DNA sequence is cloned, isolated, for example, using agarose gel electrophoresis and then incorporated into an amplification vector and amplified by a standard polymerase chain reaction technique for a sufficient number of cycles to obtain a desired quantity of DNA (depending upon the amount of DNA desired, from about 5 cycles to about 40 cycles or more). A signal peptide sequence and/or anchor peptide sequence may be incorporated into a vector containing the MSA1 peptide and, after identification (selection and screening) of the appropriate DNA fragments in positive clones by PCR and endonuclease digestion, amplified accordingly using the same techniques.

After amplification, the DNA is incorporated into a transfer vector and transfected with eukaryotic cells, for example, monkey kidney cells (BSC-1 cells), and with wild-type vaccinia virus (WR) to produce recombinant vaccinia virus. The recombinant vaccinia virus is then purified before amplification. After amplification and in some cases further purification, the recombinant vaccinia virus is then administered to an animal as an immunogenic dosage form which expresses MSA1 peptide or an immunogenic portion thereof, preferably, in combination with a signal peptide and/or an anchor peptide.

Alternatively, once a nucleic acid sequence encoding immunogenic chimeric protein is present in a suitable expression vector, the expression vector may be used for the purpose of expressing the immunogenic chimeric protein in a suitable eukaryotic cell system, for example, to promote the production of the desired peptide sequence outside of the host animal. Such eukaryotic cell systems include, for example, HeLa, L929, T2 or RMA-2, preferably T2 or RMA-S. In this method, the cells which contain the expression vector(s) are grown and then lysed in order to isolate synthetic peptides which contain the desired protein or peptide sequence in combination with the anchor peptide sequence and/or the signal sequence. The isolated peptide sequence may then be used directly as a therapeutic or immunogenic dosage form. Alternatively and preferably, the expression vector may be administered directly to the patient where it will express the desired protein or peptide and anchor sequence and render the intended therapeutic or immunogenic effect on the patient.

The expressed protein may be obtained from cell culture after the cells are lysed by standard protein purification procedures known in the art which may include, among others, gel electrophesis, affinity and immunoaffinity chromatography, differential precipitation, molecular sieve chromatography, isoelectric focusing and ion-exchange chromatography. In the case of immunoaffinity chromatography, the protein or peptide may be purified by passage through a column containing a resin to which is bound antibodies which are specific for at least a portion of the protein or peptide.

The expressed protein or peptide containing a signal peptide sequence and/or an anchor peptide sequence, which is obtained from cell culture, may be administered in pure or substantially pure form to a patient in need of such therapy by purifying the crude lysate from cell culture. Preferably, the expressed protein is administered in pharmaceutical dosage form as a composition or formulation comprising an immunogenically effective amount of the expressed protein containing anchor peptide sequence and/or signal peptide sequence, in combination with a pharmaceutically acceptable additive, carrier or excipient. The formulations may be delivered in unit dosage form prepared by known methods in the art. The amount of expressed protein or peptide administered will vary depending upon the pharmokinetic parameters, severity of the disease treated or immunogenic response desired. Of course, dosages will be set by the prescribing physician considering relevant factors including the age, weight and condition of the patient including, in the case of immunogenic dosage forms, whether the patient has been previously exposed to the microorganism responsible for the disease to be vaccinated against as well as the release characteristics of the expressed protein from pharmaceutical dosage forms of the present invention.

The amount of the expressed protein which is administered according to the present invention comprises an amount effective to produce the intended effect, i.e., to obtain an immunogenic response in the patient which provides a substantially protective effect against malaria.

Alternatively and preferably, the vaccine which is administered according to the present invention comprises an amount of an expression vector, preferably, a recombinant vaccinia virus effective to express sufficient MSA1 peptide to provide an immunogenic response in a patient. Preferably, the MSA1 peptide or an immunogenic peptide sequence thereof is combined with a signal and/or anchor peptide to substantially increase the immunogenicity of the expressed MSA1 peptide compared to MSA1 peptide which does not contain a signal and/or anchor peptide. The immunogenic response provides a protective effect against the merozoite stage of malaria.

The present vaccine can be injected as is, or for convenience of administration, can be added to a pharmaceutically acceptable carrier. Suitable pharmaceutically acceptable carriers will be apparent to those skilled in the art, and include water and other polar substances, including lower molecular weight alkanols, polyalkanols such as ethylene glycol, polyethylene glycol, and propylene glycol as well as non-polar carriers.

Dosages of recombinant vaccinia virus or chimeric protein or peptide according to the present invention which are coadministered with carriers will often be about the same as the amount administered alone (in the absence of co-administration). Of course, dosages will be set by the prescribing physician considering relevant factors including the age, weight and condition of the patient including whether the patient has been previously exposed to *Plasmodium falciparum* and the release characteristics of the vaccinia virus from pharmaceutical dosage forms of the present invention.

In the malaria vaccine aspect of the present invention, the dose of vaccinia virus will depend upon the form in which it is administered. For example, the vaccine will generally contain a concentration of virus ranging from about $10^4$ to about $10^7$ plaque forming units, preferably about $1\times10^6$ to about $5\times10^6$ plaque-forming units, depending upon the desired levels of expressed immunogenic protein. Thus, the concentration or amount of vaccinia virus included within the present vaccine will generally fall within this range; however, the amount of recombinant vaccinia virus used in any vaccine form will depend upon the strength of the immunogenic response elicited.

In determining the amount of vaccinia virus in a given vaccine dose, the following method may be used. In certain vaccine dosage forms, standard pharmaceutical carriers as described above may be included. The ratio of virus included in the vaccine will depend on the chemical nature, solubility, and stability of the virus, as well as the dosage contemplated. For parenteral administration or injection via such parenteral routes as intraperitoneal, intramuscular, subcutaneous, intramammary or other route, sterile solutions of the vaccinia virus are prepared. Vaccines according to the present invention may also be administered intravenously. Preferably, the vaccines according to the present invention are administered via a subcutaneous route.

The dosage of the vaccine employed and the treatment schedule would follow practices normally employed for other vaccination or therapeutic regimens wherein this general method of treatment is employed. It is not anticipated that more than one dose of vaccine initially would be required, but the possibility of providing booster doses is anticipated. Preferably, the dosage schedule for immunization against malaria involves the subcutaneous injection of at least about $1\times10^6$ plaque-forming units of vaccinia virus.

In the immunogenic method according to the present invention, a human patient is administered with an effective amount of vaccinia virus such that expressing the MSA1 peptide or an immunogenic peptide thereof, preferably in combination with a signal and/or anchor peptide. Alternatively, an immunologically effective chimeric peptide comprising the MSA1 peptide or an immunogenic portion thereof in combination with a signal peptide and/or anchor peptide will be administered. In certain instances, an additional boost of vaccinia virus or peptide may be given to promote the immunogenic response. Additional doses of vaccine may be provided to boost the initial inoculation, if needed.

The following examples are provided for purposes of illustration only and are not to be viewed as a limitation of the scope of the invention.

EXAMPLES

Methods and Materials

Virus and Cells

Monolayer cultures of monkey kidney cells (BSC-1) and Hu134TK-cells were grown in Dulbecco's modified Eagle's medium (D-MEM) supplemented with 10% fetal bovine serum (FBS). Monolayer cultures of Hela cells and CV-cells were grown in Dulbecco's modified Eagle's medium (D-MEM) supplemented with 10% FBS.

Wild type vaccinia virus Western Reserve (WR) was grown in BSC-1 cells.

In vitro culture of *P. falciparum*

*P. falciparum* isolates (FCR-3, a strain identical to the Wellcome strain sequenced by Holder, et al., *Nature*, 1985, 317, 270–273) were maintained in human erythrocytes in RPMI 1640 medium supplemented with 25 mM Hepes, 32 mM sodium bicarbonate and 10% human serum in a 5% $O_2$, 5% $CO_2$, 90% $N_2$ environment at 37° C. *P. falciparum* strain FCR-3 was kindly donated by Dr. Isabella Quakyi, Georgetown University, Washington, D.C.

Preparation of Antisera to C-terminal of MSA1 pME-2 is an expression plasmid derived from pWRL507, in which the C-terminal of the MSA1 gene (3555–5917 bp, Wellcome Allele of MSA1) was inserted at the 3' end of a truncated trpE gene, so that expression was controlled by the trp promoter. The protein was expressed using the method described by Holder, et al., *Paraite Immunol.*, 1988, 10, 607. The fusion protein expressed was insoluble. DH5 alpha competent cells (GIBCO BRL) were transformed by pME-2, and a 1 ml culture of a pME-2 positive clone was innoculated into 100 ml M9 medium containing 100 ug/ml (micrograms per ml) Amp and grown overnight. This overnight culture was added to 400 ml M9 containing 100 ug/ml Amp and 10 ug/ml indoleacrylic acid, and after 5 hr. growth at 37° C. and 250 rpm, the cells were harvested. The pellet was then rinsed in 10 ml PBS and frozen to −20° C. The cell pellet was thawed in a 10 ml solution containing 25 mM Tris pH 8.0, 1 mM EDTA, 0.2% NP-40 and 100 ul 100 mM PMSF.

When the pellet was fully resuspended, lysozyme was added to a final concentration of 1 mg/ml, and the solution was placed on ice for 2 hrs. After this time, 20 ul 1M MgSO4, and 20 ul 10 mg/ml DNase were added, and the solution was again left to incubate on ice for 2 hrs. After 10 min. centrifugation at 13000 rpm, the pellet was rinsed in 10 ml of washing buffer (50 mM Tris, 5 mM EDTA, 5 mM EDGA, 1% NP-40 containing 100 ul 100 mM pMSF). The material was centrifuged as above to yield a futher pellet and this pellet was resuspended in a 10 ml solution of 0.5 M KSCN, 50 mM tris, 5 mM EDTA and 5 mM EGTA and re-centrifuged as above. Finally, the pellet was resuspended in 3 ml water. The product was anayzed by SDS-polyacrylamide gel electrophoresis (SDS-PAGE), and the gel containing the 105 kD protein of interest was then cut into approximately 1–5 $mm^2$ pieces. The fusion protein was eluted with a Bio-Rad Model 422 Electro-Eluter, and the vacuum-dried product was dissolved in PBS. The concentration was assayed with a BCA protein Assay Reagent Kit (PIERCE). Antiserum to the fusion protein was prepared by immunizing Balb/c mice intraperitoneally on two occasions 21 days apart with 100 ug of protein in the presence of Titre-Max (Vaxcel, Inc.). Antiserum was collected 10 days after the second immunization.

Plasmid Construction (1) Amplification of MSA1 signal sequence (Si)

pGEX-2T-P190CR1 (pGEX-2T containing the MSA1 gene from 1 to 150 bp) was used as a sample in PCR. The 100 ul mixture contained 100 pmol primer 1 and 100 pmol primer 2 (Table 1, below), 2.5 units Ampli Taq DNA polymerase, dNTP and 10 ul 10× reaction buffer (PIERCE). The sample was overlaid with several drops of mineral oil to prevent evaporation and subjected to 30 cycles of amplification (94° C. melt, 72° C. extension, 55° C. annealling). Amplified products were identified on a 1.5% agarose gel.

TABLE 1

Relative Positions of Amplified Gene Fragments From PF MSA1 and Primer Sequences

| Amplied Gene Fragments | Relative Position in MSA1 Gene[a] | Primer | Primer Sequence | |
|---|---|---|---|---|
| Fragment Containing Signal Sequence | 418–582 | 1 | GC <u>GTCGAC</u> ATG AAG ATC ATA TTC TTT TTA<br>SalI | (Sequence ID No.9) |
| | | 2 | GC <u>GAATTC</u>AA TTC ATT TAA TAC CAT TTT TTC<br>EcoRI | (Sequence ID No.10) |
| MSA1C-A | 3556–5337 | 3 | GC <u>GAATTC</u> ACT TAA TAA CCC AAA GCA TGT<br>EcoRI | (Sequence ID No.11) |
| | | 4 | GC <u>GGTACC</u> TTA AAT GAA ACT GTA TAA TAT<br>KpnI | (Sequence ID No. 12) |
| MSA1C-Si,nA | 418–582<br>3553–5280 | 1 | GC <u>GTCGAC</u> ATG AAG ATC ATA TTC TTT TTA<br>SalI | (Sequence ID No.9) |
| | | 5 | GC <u>GGTACC</u> TTA GTT AGA GGA ACT GAC GAA AAT<br>KpnI | (Sequence ID No.13) |
| MSA1C-nSi,nA | 475–582<br>3553–5280 | 6 | GC <u>GTCGAC</u> ATG GTA ACA CAT GAA AGT TAT CAA<br>SalI | (Sequence ID No.14) |
| | | 5 | GC <u>GGTACC</u> TTA GTT AGA GGA ACT GAC GAA AAT<br>KpnI | (Sequence ID No.13) |
| MSA1C,nSi,A | 475–582<br>3553–5337 | 6 | GC <u>GTCGAC</u> ATG GTA ACA CAT GAA AGT TAT CAA<br>SalI | (Sequence ID No.14) |
| | | 4 | GC <u>GGTACC</u> TTA AAT GAA ACT GTA TAA TAT<br>KpnI | (Sequence ID No.12) |

[a]GCG, Accession no. X02919. The start codon of MSA1 is at 418.
The MSA1C-(Si,nA), MSA1C-(nSi,nA), MSA1C-(nSi,A) fragments contain the 108 bp region directly downstream from the signal sequence and an additional 2 bp on the 5' end of the C-terminal to preserve the reading frame. Furthermore, a start codon was also added to the two fragments lacking the start-codon-containing signal sequence, a stop codon was also added to the two fragments lacking the anchor region.

(2) Amplification of C-Terminal of MSA1 (MSA1C-A)

pME-2 plasmid was used as a template in PCR. The 100 ul (microliter) mixture contained primers 3 and 4 (Tab. 1) and was subjected to 30 cycles of amplification (94° C. melt, 72° C. extension, 50° C. annealling). The amplified products were identified on a 0.8% agarose gel.

pSPORT1-MSA1C-(Si,A)(FIG. 1) was used as a template in PCR. MSA1C-(Si,nA) (primer 1 and primer 5, Tab. 1), MSA1C-(nSi,A) (primer 5 and primer 4), and MSA1C-(nSi, nA) (primer 6 and primer 5) fragments were amplified as well with the above procedures.

(3) Isolation, Purification and Cloning of Gene Fragments

The MSA1C-A fragment was amplified by PCR, and electrophoresis in a 0.8% agarose gel indicated that the amplified fragment was about 1.8 kb. This fragment and pSPORT1 were digested with EcoRI and KpnI and were mixed and treated with T4 DNA ligase. The ligation products were transformed into DH5alpha competent cells. X-gal and ampicillin were used to screen the positive clones (pSPORT1-MSA1C-A, FIG. 1). Recombinant plasmids were prepared from positive white colonies and identification was performed with SalI and EcoRI digestion. The full sequence of the insert was determined.

The fragment containing the signal sequence was amplified by PCR, and electrophoresis in a 1.5% agarose gel indicated that the size of the amplified fragment was about 180 bp. The Si and pSPORT1-MSA1C-A fragments were then digested with SalI and EcoRI, ligated and transformed, and 30 colonies were selected and screened by PCR using primer 1 and primer 2. Recombinant plasmids (pSPORT1-MSA1C-(Si,A), FIG. 1) were identified with SalI and EcoRI digestion and were sequenced, and the correct reading frame was established. pSPORT1-MSA1C-(Si,A) was then used as a template to amplify MSA1C-(Si,nA), MSA1C-(nSi,A) and MSA1C-(nSi,nA).

MSA1C-(Si,nA), MSA1C-(nSi,A), MSA1C-(nSi,nA) digested with SalI and EcoRI and MSA1C-(Si,A) cut from pSPORT1-MSA1C-(Si,A) were inserted separately into the SalI and KpnI sites of pSC65. Positive clones were screened by PCR and SalI and KpnI digestion, the 5' and 3' ends of each insert were sequenced, and the correct reading frame was established.

Figure 1B:
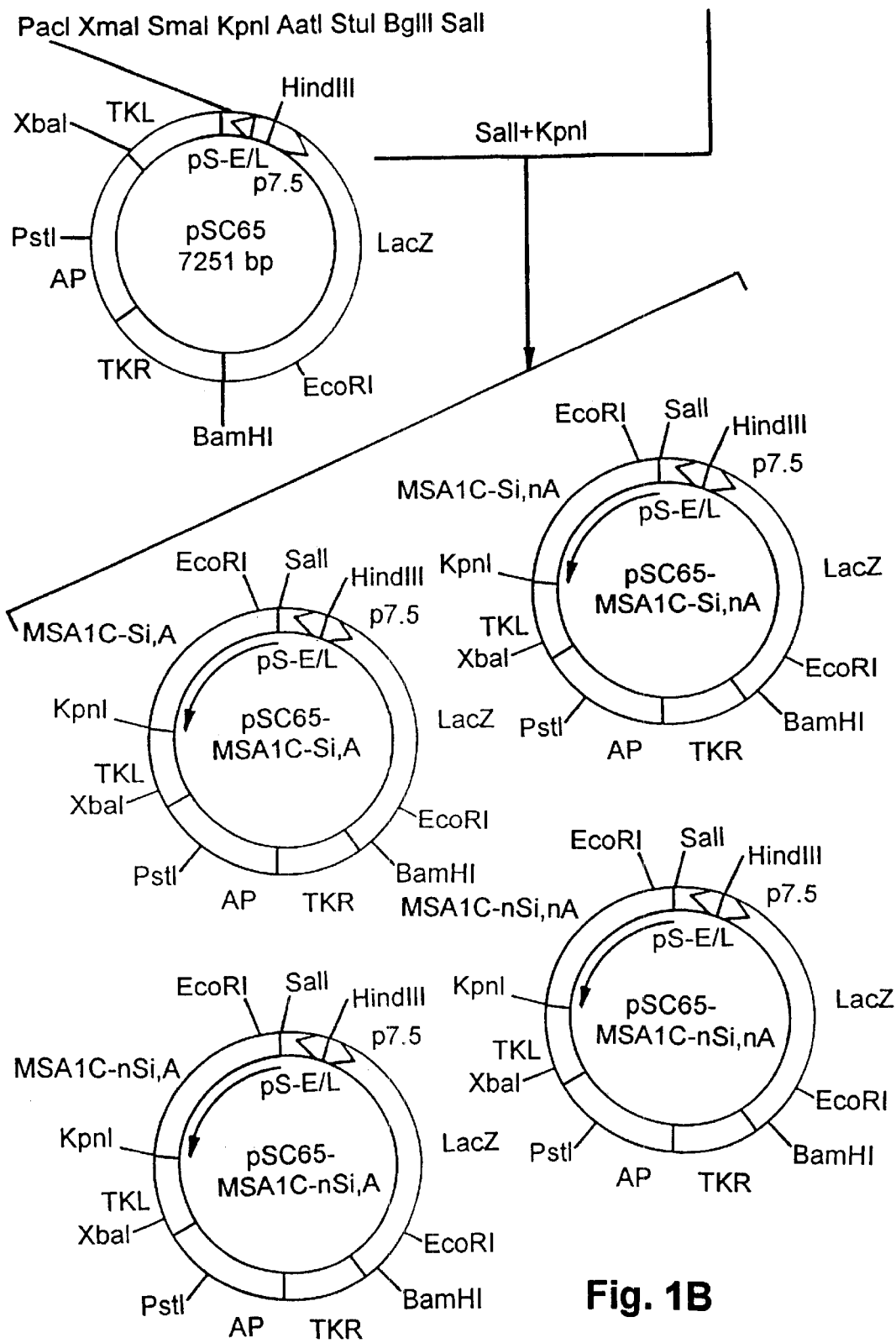

FIG. 1 diagrams the construction of recombinant vaccinia viruses incorporating the sequences corresponding to MSA1C-(Si,A), MSA1C-(Si,nA), MSA1C-(nSi,A) and MSA1C-(nSi,nA). Essentially, the MSA1C-terminal fragment containing the anchor region was inserted into the pSPORT1 plasmid using the marked EcoRI and KpnI sites, creating the pSPORT1-MSA1C-A plasmid. The fragment containing the signal region (FSi) and the 108 bp downstream was PCR amplified with a SALIU site on the 5' end and then inserted into the pSPORT1-MSA1C-A plasmid to produce pSPORT1-, SA1C-(Si,A) plasmid. The entire MSA1C-(Si,A) fragment (from the SalI site to the KpnI site) was then removed and inserted into the pSC65 vector to make the final pSC65-MSA1C-(Si,A) transfer vector. The other three recombinant transfer vectors (pSC65-MSA1C-(nSi,nA), pSC65-MSA1C-(nSi,A) and pSC65-MSA1C-(Si, nA)) were produced by adding the desired SalI or KpnI sites where necessary by PCR amplification. The amplified fragments were then inserted into the pSC65 plasmid. In all four cases, the insertion site is adjacent to the synthetic early/late promoter (pS-E/L). $Tk_L$ and $TK_R$, right and left regions of the vaccinia virus thymidine kinase gene; LacZ, beta-galactosidase gene.

DNA Sequencing

DNA sequencing was performed using the dideoxy nucleotide chain termination method according to the protocols for DNA sequencing with TAQ version 2.0 DNA polymerase (United States Biochem). FIGS. 2–5 are the DNA (gene) sequences for MSA1C-(Si,A), MSA1C-(Si,nA), MSA1C-(nSi,A) and MSA1C-(nSi,nA).

Transfection and Isolation of Recombinant Vaccinia Viruses

Monolayers of BSC-1 cells were grown to 90% confluence in a six-well plate, media was removed, and the cells were infected with wild-type vaccinia virus (WR) at 0.1–1 plaque forming units(pfu)/cell for 1 hour. The virus inoculum was removed, and the monolayer was washed twice with OptiMEM (GIBCO BRL) serum-free medium. 1 ml of Opti-MEM was added to the infected monolayers and mixed gently with 50 ul of lipofectin-DNA complex (5 ug of recombinant pSC65 was diluted to 25 ul with sterile distilled water, 15 ug of lipofectin reagent was diluted to 25 ul with sterile distilled water, and the solution was gently mixed in a polystyrene tube and allowed to stand for 15 minutes at room temperature). After 5 hours incubation at 37° C., the medium was replaced with 3 ml E-MEM supplemented with 2% FBS and incubated for another 48 hours. After removal of the medium, cells were harvested by scraping into 1 ml of E-MEM supplemented with 2% FBS. The virus was released by three cycles of freeze-thawing at 37° C. After removal of medium, 1 ml of diluted freeze-thawed transfection mixture (sonication 30 seconds at 4° C. before adding) was added to monolayers of Hu 134 TK-grown to 90% confluence in a six-well plate, and the virus was left for 1 hour at 37° C. The infected cells were overlaid with E-MEM supplemented with 2% FBS containing 1% low-melting-point agarose and 25 ug/ml of bromodeoxyuridine. Thirty-six hours post-infection, monolayers were overlaid with E-MEM supplemented with 2% FBS containing 1% low-melting-point agarose, 0.02% neutral red and 300 ug/ml X-gal. After the agarose had set, monolayers were incubated for 6–8 hours before plaques were stained and picked (using a sterile glass Pasteur pipette) into 1 ml of diluent and freeze-thawed 3 times. The recombinant products were plaque purified before amplification to produce small virus stocks.

Immunostaining of Vaccinia Recombinant Plaques

BSC-1 cells were infected with recombinant vaccinia virus, and the medium was removed from infected tissue-culture plates 24 hours postinfection. The cells were fixed with a 1:1 acetone:methanol mixture for 2 minutes, the wells were washed with 1 ml of PBS, and then anti-MSA1C-A serum diluted 1:200 in PBS containing 2% FBS was added to the wells, 1 ml/well. The six-well plate was incubated at room temperature for 1 hour, rocking gently, after which the wells were washed twice with 1 ml of PBS. Anti-mouse-peroxidase diluted 1:1000 in PBS with 2% FBS was added to each well, and the plate was incubated for 45 minutes at room temperature. After washing twice with PBS, 0.5 ml of substrate solution was added (the substrate solution was made by dissolving a pinch of dianisidine in 500 ul of absolute ethanol, vortexing, and warming it for 5–10 minutes, then centrifuging it for 30 seconds and adding 200 ul of substrate solution to 10 ml of PBS plus 10 ul of 30% $H_2O_2$). The plate was then left for 5–10 minutes at room temperature.

Indirect Immunoflourescence Staining of Recombinant Vaccinia-infected Cells

HeLa cells were seeded on pre-treated coverslips for 48 h, after which the cells were infected at an M.O.I. of 5 in a volume of 0.25 ml of D-MEM uith 10% FBS. These were overlaid with 1.5 ml D-MEM with 10% FBS 1–2 h postinfection. The cells were then washed with PBS and fixed for 15 min in 3% paraformaldehyde in PBS. After being washed in PBS, the coverslips were incubated in 50 mM ammonium chloride in PBS for 10 min at room temperature. After the slips were again washed in PBS, anti-MSA1C-A serum diluted 1:800 in PBS was added to each well, and they were incubated for 30 min at 4° C. The coverslips were then washed three times in PBS, and the cells were incubated with FITC goat-anti-mouse for 30 min at 4° C. After being washed in PBS, the coverslips were blotted on tissue and mounted on slides in 5% DABCO/Mowiol.

Western Blot Analysis

Confluent six-well plates of BSC-1 cells were infected with recombinant vaccinia virus in 1 ml medium at an M.O.I of 5. Cells from each well were harvested 24 hours postinfection. After centrifugation at 8000 rpm for 5 min, the supernatant was concentrated to 10–15 ul with a microcon 30 (Amicon, Inc.), and the cell pellet was resuspended in PBS to a final volume of 200 ul. The same volume of 2× sample buffer (100 mMTris, 200 mM dithiothreitol, 4% SDS, 0.2% bromophenol blue and 20% glycerol) was added, and the resulting solution was boiled for 5 min and loaded in a 8% Tris-glycine-SDS gel. Electrophoresis was performed in Tris-glycine-SDS running buffer, and proteins were transfered to a PVDF membrane by electrophoresis in transfer buffer (25 mM Tris-HCl, 192 mM glycine, 155 methanol) at 100 V for 30 min at 4° C. The blot was blocked with 5% BSA in Tris-HCl (200 mM, 0.85%) for 2 h at room temperature before addition of a 1:500 dilution of anti-MSA1C-A serum. After 2 hours incubation the blot was washed three times in Tris-HCl, pH 7.4 for 10 min per wash. A 1:7500 dilution in Tris-HCl, pH 7.4 of alkaline phosphatase-conjugated goat-anti-mouse IgG (Promega) was added, and the blot was incubated for 90 min at room temperature before being washed four times in Tris-HCl, pH 7.4 for 10 min each wash. Western blue stabilized substrate for alkaline phosphatase (Promega) was added, and after about 5 minutes, the blot was washed with water to stop development.

Large-scale Preparation and Plaque Titration of Vaccinia Virus Stocks (1) Purification of Vaccinia Viruses $5 \times 10^7$–$10^8$ HeLa S3 cells in E-MEM supplemented with 2% FBS were incubated in a 162 $cm^2$ flask at 37° C. for 18 h, after which the cells were infected with small stock viruses at 37° C. for 48 h and pelleted by centrifugation for 5 min at 1800 g. The infected cells were resuspended in 10 mM Tris-HCl, pH 9.0 and homogenized with 30–40 strokes (while still on ice). The mixture was centrifuged for 5 min at 300 g to remove nuclei, and the pellet (removed supernatant was kept was well) was resuspended in 10 mM Tris-HCl, pH 9.0 and centrifuged again (supernatants were pooled). The sonicated supernatant was layered onto a cushion of 36% sucrose in a Beckman SW27 centrifuge tube and spun at 35000 rpm for 45 min at 4° C., after which the virus pellet was resuspended in 1 ml of 1mM Tris-HCl, pH 9.0. The wild-type virus was further purified by continuous sucrose gradient centrifugation.

(2) Plaque Titration of Vaccinia Virus Stocks

Monolayers of BSA-1 cells were grown to 95% confluence in a six-well plate, virus stocks were sonicated, and 10 fold serial dilutions($10^{-7}$–$10^{-9}$) of the virus in E-MEM supplemented with 2% FBS were made. The BSC-1 cells were infected with 1 ml of virus diluted to $10^{-7}$, $10^{-8}$ and $10^{-9}$ in duplicate. After 48 h of incubation, the medium was removed and 0.5 ml of crystal violet solution was added. After another 15 min incubation at room temperature, the plates were washed with water, and the plaques were counted after drying.

ELISA Determination of Antibody Response
(1) Antibody Responses to MSA1C-A

A ninety-six-well microtiter plate (IMMULON 2, Dynatech Laboratories Inc, VA) was coated with 100 ul/well of a 5 ul/ml solution of MSA1C-A in Tris-NaCl (0.02,0.85%), pH 7.4 and kept overnight at 4° C. The antigen-coated plate was then washed with Tris-NaCl and blocked with 150 ul 1% BSA in Tris-NaCl, pH 7.4 for 2 h at 37° C. After washing with Tris-NaCl, pH 7.4, 100 ul of serial 10-fold dilutions (diluted in Tris-NaCl containing 1% BSA and 0.05% Tween 20) of sera were added to the wells in duplicate. After 2 h incubation at 37° C., the plate was rewashed with Tris-Nacl containing 0.05% Tween 20 and phosphatase-labeled IgG was added. After another 2 h incubation at 37° C., the plate was washed with Tris-NaCl containing 0.05% Tween 20 and developed by adding alkaline phosphatase substrate in diethanolamine buffer, pH 9.8. The plate was scanned in a Dynatch ELISA scanner at 405 nm.
(2) Antibody Responses to Vaccinia Virus Purified WR vaccinia virus was diluted in Tris-NaCl, pH 7.4 to a final concentration of approximately $5\times10^6$ pfu/ml and 100 ul volumes were dispensed into the wells of a 96-well plate (IMMULON 2, Dynatech Laboratories Inc) and left for 2 h at 37° C. The buffer was removed and virus was inactivated with 50 ul of 10% paraformaldehyde for 10 min at 4° C. The plates were then blocked just as those in the first group and developed using the procedure described above.

Indirect Fluorescent-antibody Tests for Parasite

*P. falciparum* parasites were cultured in human erythrocytes to a parasitemia of 8% at the schizont stage, at which point they were washed five times in PBS (10×volume). Small samples were then taken, smeared on a glass slide and fixed in cold methanol. After being washed in PBS, the samples were probed with antiserum from mice immunized with the recombinant and wild-type viruses. After this probe, the samples were probed with FITC goat-anti-mouse antibody and mounted in 5% DABCO/Mowiol.

In vitro Invasion Assay

Preparation of samples: Rabbit pre-immune serum or anti-serum (6.7 ml) was heat-inactivated at 56° C. for 25 minutes, and antibodies in the absorbed serum were precipitated with ammonium sulfate. After centrifugation, the pellets were dissolved in a minimal volume of PBS, then dialyzed overnight three times in PBS. Finally, the volume was adjusted to 1 ml.

*P. falciparum* parasites were synchronized twice with 5% sorbitol (Diana), and after 24 hours a mixture of trophozoites and schizonts at 3% parasitemia and 3% hematocrit was transfered to 96-well culture plates (170 ul/well). Antiserum, pre-immune serum or serum-free medium was added to the parasites in a volume of 30 ul to make a final volume of 200 ul/well, and the plates were incubated at 37° C. in an airtight chamber equilibrated for 5 min with 5% $O_2$, 5% $CO_2$ and 90% $N_2$. After 22–24 hours, cell morphology was verified to make sure that all schizonts had burst. Once this was verified, 4 ul of homogenized infected red blood cells from each well were fixed in 2 ml 0.01% (w/v) glutaraldehyde for 45 min at room temperature. After fixing, the cells were centrifuged at 1500 rpm at 4° C. for 10 min and then stained with 50 ug/ml propidium iodide overnight at 4° C. in darkness. Total parasitemia was determined by counting fluorescent cells using a fluorescence-activated cell sorter. 20000 cells were counted from each sample. The percentage inhibition of invasion during the 22–24 hour period was determined by the following formula:

$$\% \ inhibition = \frac{(pre - 0\ hr) - (T - 0\ hr)}{(pre - 0\ hr)} \times 100\%$$

Here, "T" is the parasitemia of tested serum, "pre" is the parasitemia of preimmune serum and "0 hr" is the starting parasitemia.

RESULTS

Construction of Recombinant Vaccinia Virus

The construction of the recombinant vaccinia virus is described in FIG. 1. Four recombinant vaccinia virus transfer plasmids were made: pSC65-MSA1C-(Si,A), which is recombinant pSC65 in which the MSA1 peptide containing the signal and anchor regions of MSA1 has been inserted into the SalI and KpnI site; pSC65-MSA1C-(Si,nA) (the same except the MSA1 contains the signal without the anchor); pSC65-MSA1C-(nSi,A) (the same except the MSA1 contains the anchor without the signal) and pSC65-MSA1C-(nSi,nA) (the same except the MSA1 contains neither the signal nor the anchor).

The vaccinia virus transfer vector, pSC65, has a synthetic compound early/late promotor (pSE/L) so that the foreign genes controlled by the promotor are expressed throughout the virus growth cycle. The SalI, BglII, StuI, AatI, KpnI, SmaI, XmaI and PacI sites are located just downstream of the pSE/L for insertion of a foreign gene, and there are *E. coli* beta-galactosidase gene sequences (controlled by the p7.5 vaccinia virus promotor which has early and late vaccinia virus transcriptional regulatory signals) and vaccinia TK gene sequences flanking the entire pSE/L and foreign gene region to direct homologous recombinantion into the TK locus of the vaccinia virus genome.

BSC-1 cells were infected with wild-type (WR) vaccinia virus and then were transfected with recombinant pSC65. Serial dilutions of progeny virus were then applied to monolayers of Hu 134 TK-cells in the presence of BrdU to select TK-recombinant virus plaques. These were then distinguished from spontaneous TK-mutants by addition of X-gal to the low-melting-point agar overlay. Plaques that stained blue due to expression of beta-galactosidase were picked and then plaque-purified a second time prior to preparation of virus stocks. The four recombinant vaccinia viruses were named as rV.V-MSA1C(Si,A); rV.V-MSA1C-(Si,nA); rV.V-MSA1C-(nSi,A) and rV.V-MSA1C(nSi,nA) (FIG. 6).

Expression of MSA1C-(Si,A), MSA1C-(Si,nA).
MSA1C-(nSi,A) and MSA1C-(nSi,nA)
(1) Immunostaining of Vaccinia Recombinant Plaques BSC-1 cells were infected with rV.V-N,ISA1C-(Si,A), rV.V-MSA1C(Si,nA), rV.V-MSA1C-(nSi,A) and rV.V-MSA1C-(nSi,nA), and the infected cells were fixed with acetone/methanol 24 hours post-infection, after which the expressed proteins were labeled by anti-mouse-peroxidase. The results indicated that the cells infected by the recombinant vaccinia virus expressed the C-terminal protein.
(2) Western Blot Analysis of Recombinant Vaccinia Virus Expressed Proteins BSC-1 cells were infected with rV.V-MSA1C-(Si,A), rV.V-MSA1C(Si,nA), rV.V-MSA1C-(nSi,A), rV.V-MSA1C-

Figure 7:
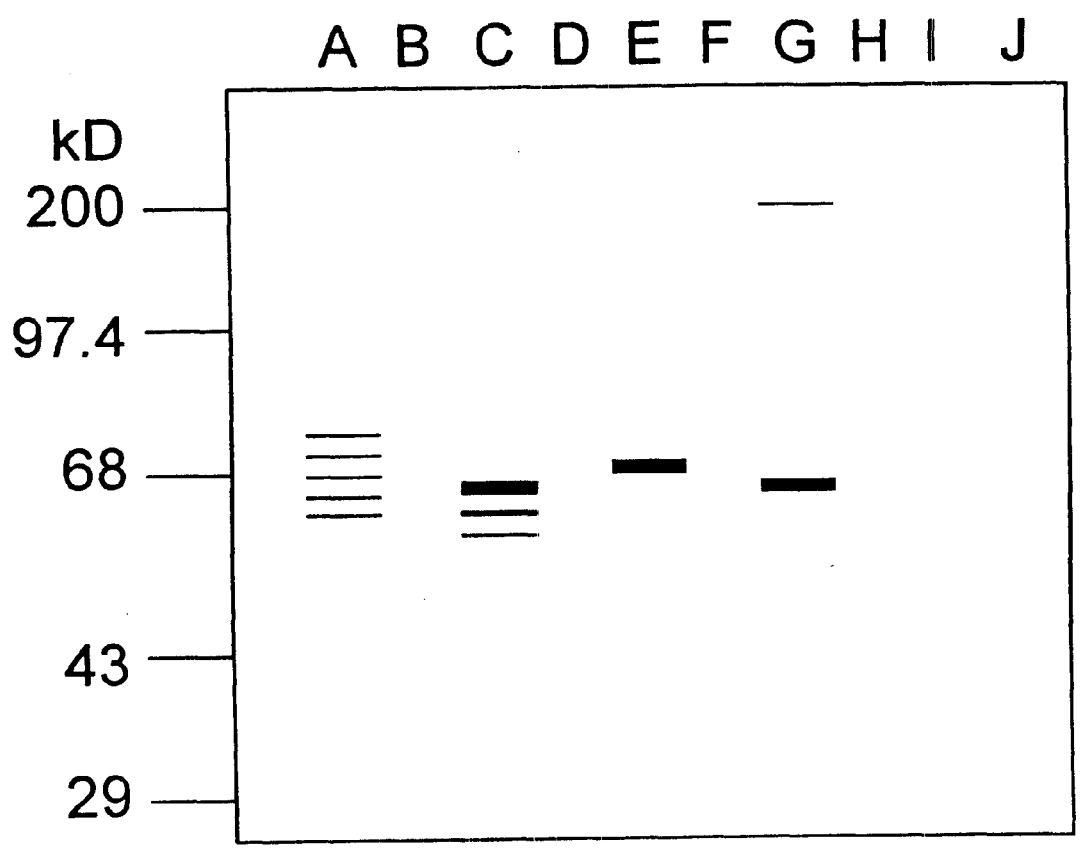
Figure 8A:
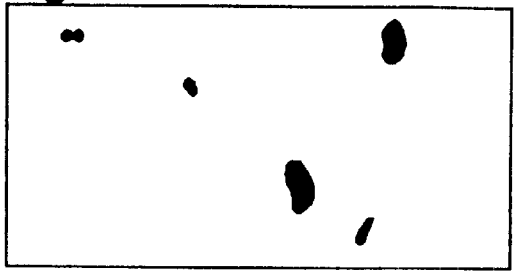
Figure 8B:
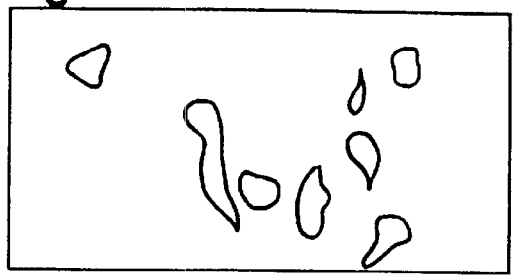
Figure 8C:
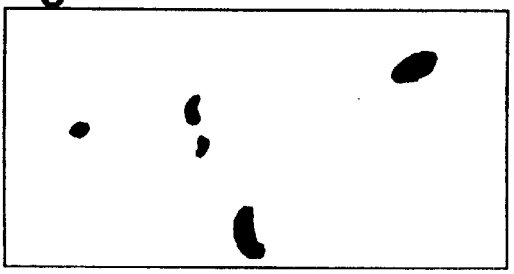
Figure 8D:
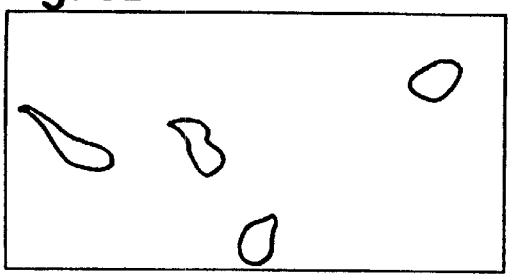
Figure 8E:
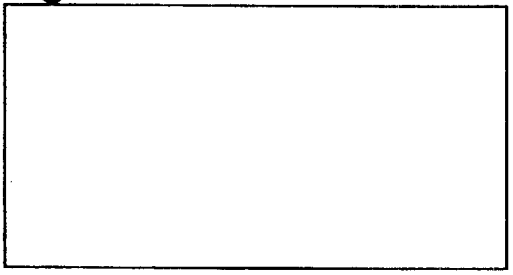
Figure 8F:
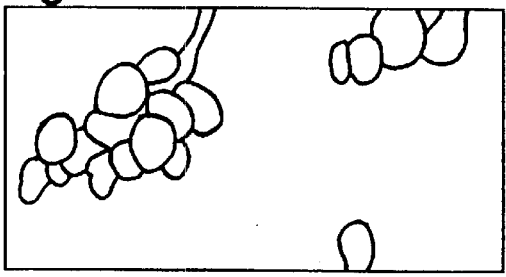
Figure 8G:
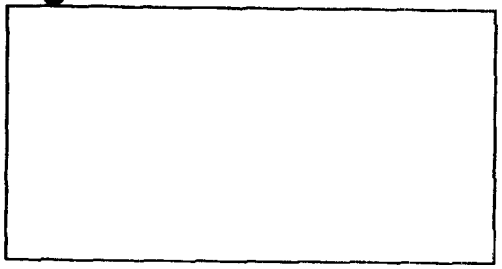
Figure 8H:
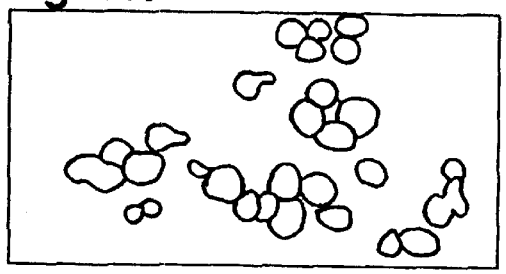
Figure 8I:
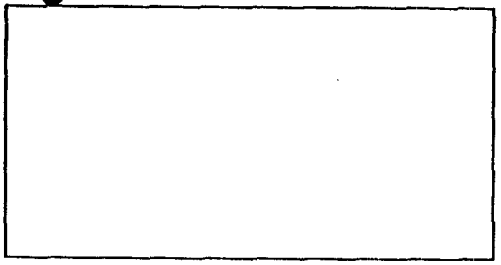
Figure 8J:
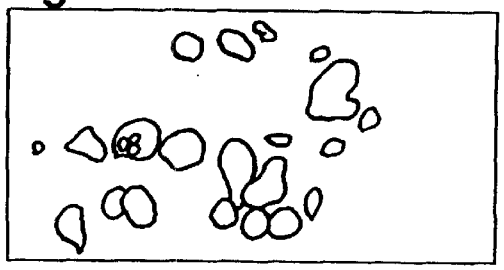

(nSi,nA) and WR viruses. These cells were then harvested 24 hours postinfection, and the cell pellets and 50-times concentrated supernatants were run on an 8% Tris-glycine-SDS gel. The blot was labled with anti-MSA1C-A mouse serum and then probed by alkaline phosphatase-conjugated goat anti-mouse IgG. The results indicated that the infected cells expressed the C-terminal region of MSA1, and that the molecular weights of MSA1C-(Si,nA), MSA1C-(nSi,A) and MSA1C(nSi,nA) were about 70 kD, and MSA1C-(Si,A) was about 60 kD. Furthermore, none of the four expressed proteins appeared to be secreted by the cells. FIG. 7 shows a Western blot analysis, using the anti-MSA1C-A mouse serum as a probe, of proteins expressed from BSC-1 cells infected with vaccinia virus.

(3) Indirect Immunofluorescence

Immunofluorescence microscopy of cells on coverslips demonstrated that MSA1C-(Si,A) and MSA1C-(Si,nA) were expressed on the surface of infected cells, and that MSA1C-(nSi,A) and MSA1C-(nSi,nA) were not expressed on the surface of infected cells. Therefore, we have concluded that the signal region is vital for the expression of the protein on the cell surface. FIG. 8 shows indirect immunofluorescence staining of recombinant vaccinia-infected cells.

(4) Antibody Response in Rabbits

Figure 9:
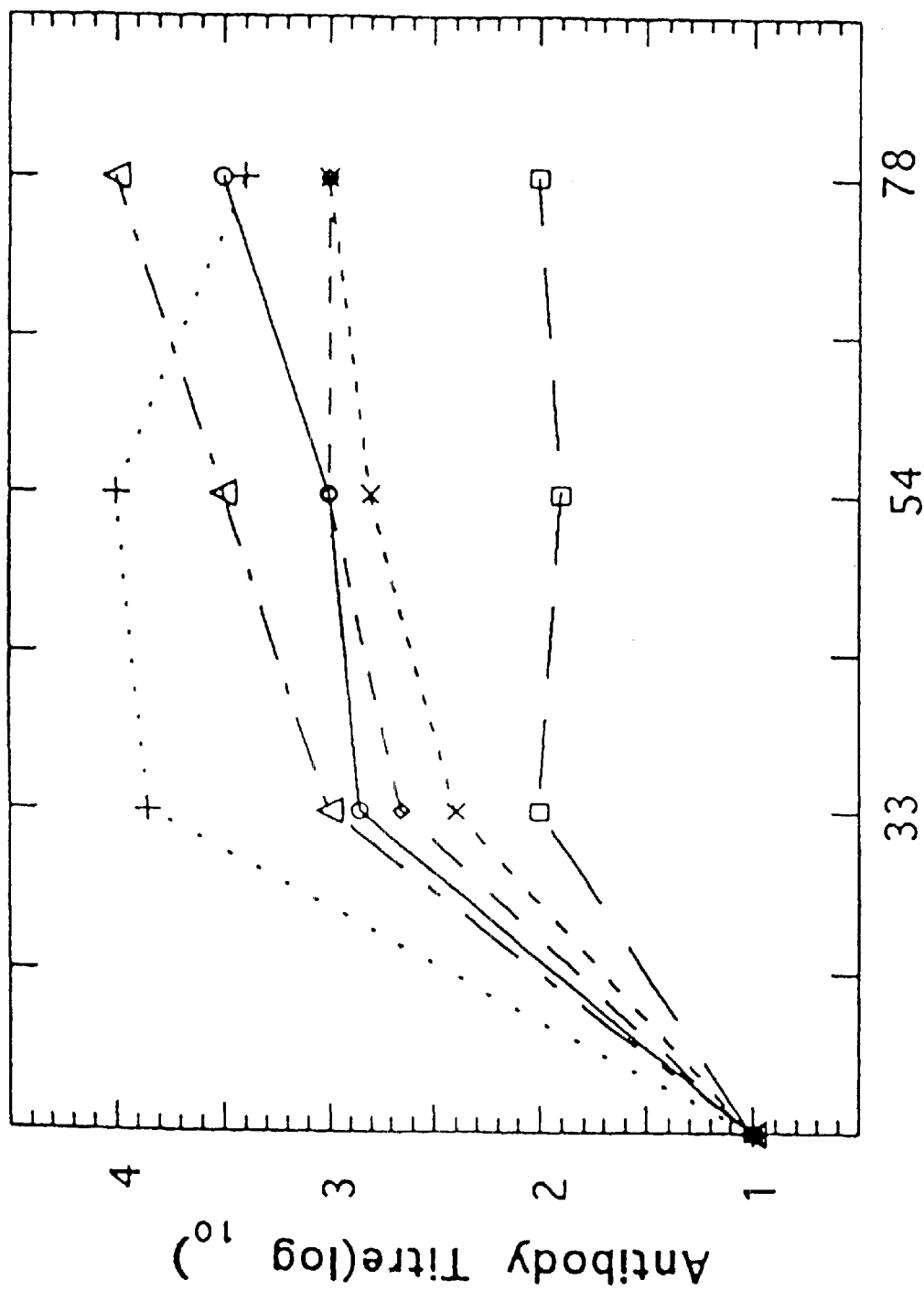

Five rabbits were inoculated intradermally with rV.V-MSA1C-(Si,A); rV.V-MSA1C-(Si,nA); rV.V-MSA1C-(nSi, nA); rV.V-MSA1C-(nSi,A) and WR on days 0, 21, 47 and 68. The ELISA titers of rV.V-MSA1C-(Si,A) and rV.VMSA1C-(Si,nA) were 5–10 times greater than that of rV.V-MSA1C-(nSi,nA) and rV.V-MSA1C-(nSi,A) after the fourth inoculation. One rabbit was inoculated intravenously on day 0 with rV.V-MSA1C-(Si,A) and reinoculated on days 47 and 68, and the ELISA titer of i.v. rV.V-MSA1C-(Si,A) was 5 times that of i.d. rV.V-MSA1C-(Si,A). Also, the ELISA titer of i.v. rV.V-MSA1C-SiA decreased suddenly after the third inoculation, possibly because the antibody neutralized the virus. The data show that rV.V-MSA1C-(Si, A) and rV.VMSA1C-(Si,nA) can induce significantly stronger antibody responses against MSA1C-A in rabbits than rV.V-MSA1C-(nSi,nA) and rV.V-MSA1C-(nSi,A), and that rV.V-MSA1C-(Si,A) can induce quicker antibody response after a second inoculation when introduced intravenously than when introduced intradermally (FIG. 9).

(5) Antibody Response in Mice

Figure 10:
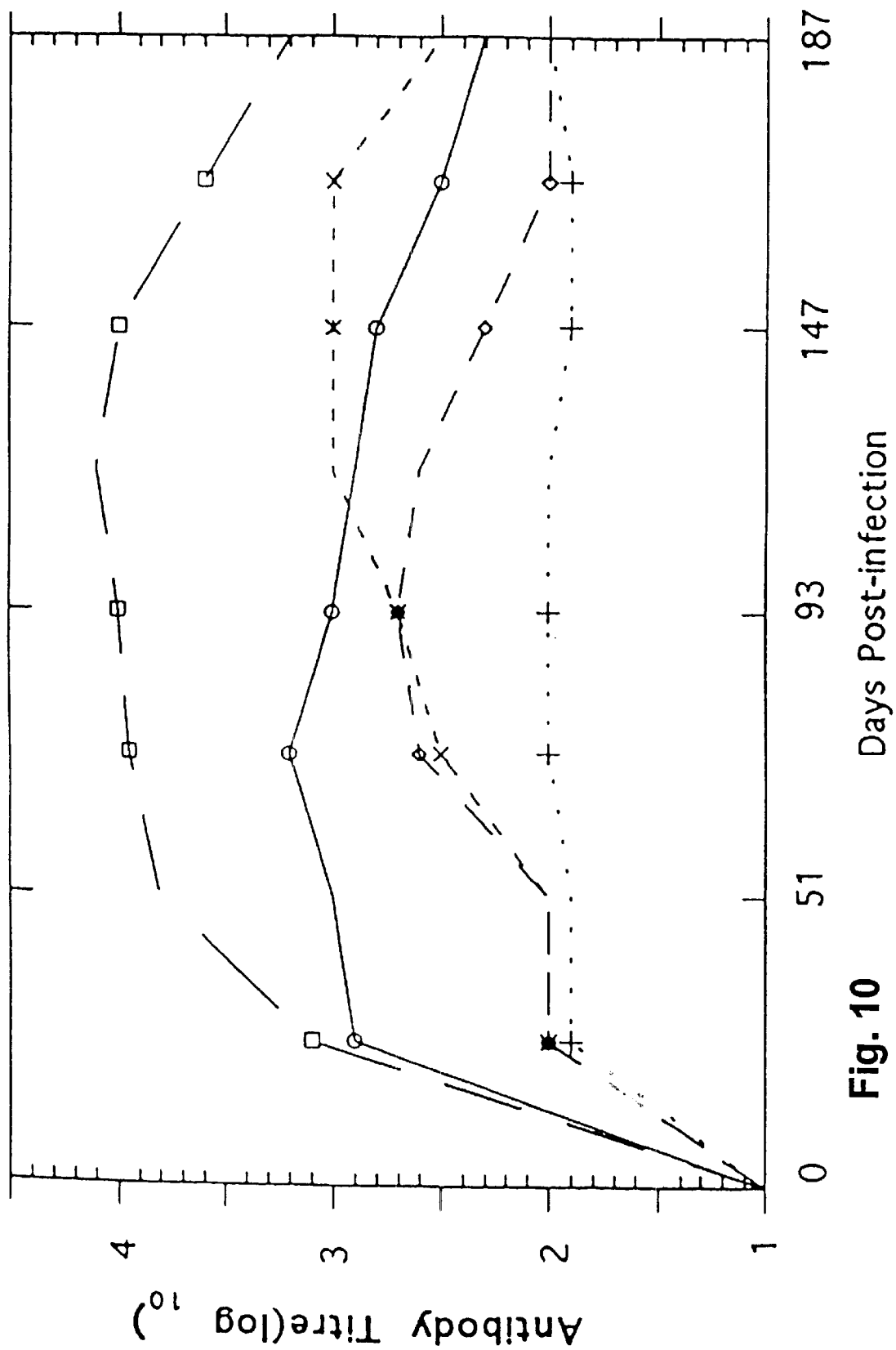

Five groups of Balb/c were inoculated i.p. with $1.0 \times 10^8$ rV.V-MSA1C(Si,A), rV.V-MSA1C-(Si,nA), rV.V-MSA1C-(nSi,nA), rV.V-MSA1C-(nSi,A) and WR. rV.V-MSA1C-(Si, A) and rV.V-MSA1C-(Si,nA) stimulated a level of the C-terminal-specific antibodies that was 5–10-fold greater than the level induced by rV.V-MSA1C-(nSi,nA) and rV.V-MSA1C-(nSi,A) after the third inoculation. The ELISA titer of rV.V-MSA1C-(Si,A) was about 1:10000 and lasted about 3 months (FIG. 10).

Wild type (WR) vaccinia virus coated on a 96-well plate was probed with a serial 10-fold dilution of mouse antibodies raised against rV.V-MSA1C-(Si,A), rV.V-MSA1C-(Si, nA), rV.V-MSA1C-(nSi,nA), rV.V-MSA1C(nSi,A) and WR, and then probed by alkaline phosphatase-labeled goat anti-mouse IgG. The results showed that the anti-WR virus antibody titers of the recombinant and the WR viruses were almost the same after the second inoculation. Therefore, it appears that all of the mice immunized with the recombinant and WR viruses were successfully infected by the viruses (FIG. 10). CBA/J mice were also immunized with rV.V-MSA1C-(Si,A), rV.V-MSA1C-(Si,nA), rV.V-MSA1C-(nSi, nA), rV.V-MSA1C-(nSi,A) and WR viruses. The resulting antibody titers were similar to those of the Balb/c mice although slightly lower (data not shown).

Figure 11:
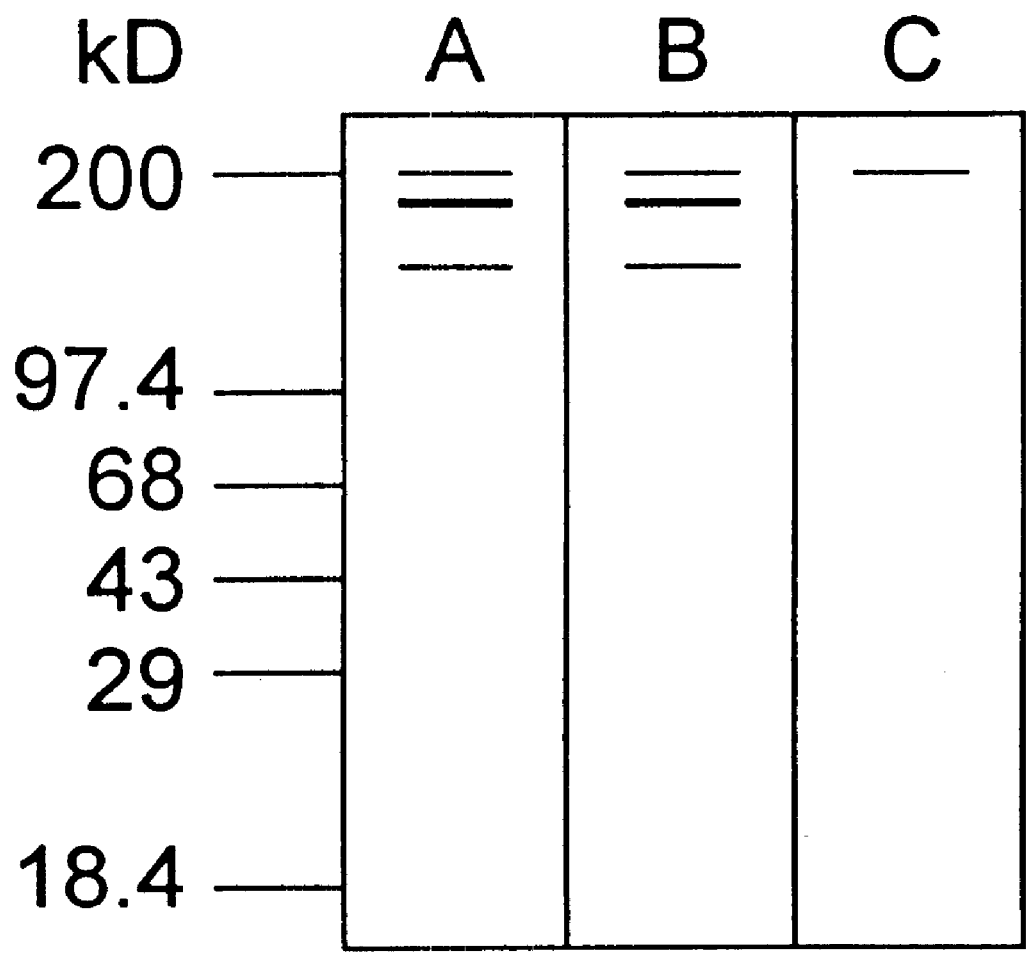

These results indicated that the cell-surface expression of the C-terminal region and the combination of the C-terminal region and the signal and anchor peptides of MSA1 are important in the stimulation of the C-terminal-specific antibody response in rabbits and mice.

rV.V-MSA1C-(Si,A)-induced Mouse Antibody Recognized 190 kD Protein of Parasite in Western Blot Schizont stage parasites resuspended in 1×sample buffer were boiled for 5 minutes and loaded onto a 4–20% Tris-glycine gradient gel, and the proteins were transferred to a PVDF membrane by electrophoresis. The blots were then probed by anti-MSA1C-(Si,A) and anti-MSA1C-A and labeled by alkaline phosphatase-conjugated goat anti-mouse IgG. The 190 kD protein was recognized by anti-MSA1C-A in a Western blot, so we have concluded that the 190 kD protein is MSA1. Anti-MSA1C-(Si,A) recognized the 190 kD protein (MSA1) as well. (FIG. 11) The data demonstrate therefore that the recombinant vaccinia virus correctly expresses the MSA1 fragment in mice.

Indirect Immunofluorescence Test for Parasite

Human erythrocytes infected with the *P. falciparum* parasite were probed with differing dilutions of the antisera produced by the mice immunized with the four recombinant viruses and the wildtype virus. MSA1C-(Si,nA) and MSA1C-(Si,A) were both positive at a dilution of 1:16, and MSA1C-(Si,A) remained positive at 1:128, while MSA1C-(nSi,nA) and MSA1C-(nSi,A) were both negative at 1:16, as compared to the WR negative control (data not shown).

Invasion Assay

TABLE 2

Inhibition of *P. falciparum* invasion of human erythrocytes by antisera (x ± s. %)

| Antisera | Antiserum dilution in culture | | | |
|---|---|---|---|---|
| | undiluted | 1:10 | 1:100 | 1:1000 |
| MSA1C-(Si, nA) | 54.6 ± 6.7 | 46.2 ± 9.4 | 30.9 ± 10.8 | 28.9 ± 9.7 |
| MSA1C-(Si, A) | 62.5 ± 10.2 | 62.8 ± 5.8 | 60.4 ± 11.0 | 45.7 ± 11.9 |
| MSA1C-(nSi, nA) | 27.0 ± 10.3 | 23.7 ± 6.3 | 20.0 ± 4.6 | 22.3 ± 3.5 |
| MSA1C-(nsi, A) | 20.2 ± 0.7 | 12.3 ± 4.9 | 25.9 ± 6.0 | 20.6 ± 5.0 |
| WR | 11.8 ± 4.0 | 8.8 ± 8.1 | 14.2 ± 1.3 | 3.8 ± 4.9 |

The Assays Were Performed in Duplicate Three Times Each.

DISCUSSION

The C-terminal region of the MSA1 protein was inserted into the vaccinia virus to investigate the immune response produced by this antigen. Four variations of the MSA1 fragment were used to create constructs which contained neither, one or both of the original MSA1 N-terminal signal sequence and the original C-terminal anchor sequence. Data from immunostaining (date not shown) and Western blot assays (FIG. 7) indicated that all four of the recombinant vaccinia virus constructs were expressed in the infected cells. The apparent molecular weight of the MSAIC-(Si,A) construct is less than expected and may be due to proteolytic cleavage of the protein during export. This size discrepency in the recombinant protein is only seen when the anchor region is present in addition to the signal sequence and it is possible that the presence of both of the two regions is necessary for the processing of the protein. The Western blot also reveals multiple bands from the MSA1C-(Si,nA) and MSA1C-(Si,A) proteins and these may be different glycosylation forms. Such a pattern is seen only in the two constructs containing the signal sequence, implying that the protein is glycosylated after entering the Golgi.

The two constructs with the signal sequence are expressed on the cell surface, whereas the two constructs without the signal sequence are not. These data indicate that the signal sequence is necessary for proper export of the expressed recombinant protein to the cell surface. Furthermore, the data show that the signal region alone is sufficient for cell surface expression. It is possible that once the protein has entered the secretory pathway, because of the signal sequence, there is resultant cell surface expression. The strength and duration of this cell surface expression appears to be greater when the protein contains the anchor region in addition to the signal region and this may be due to hydrophobic interactions. Data indicate also that the protein is not secreted externally and thus presumably remains bound to the cell surface. However, the construct with only the signal sequence elicits a weaker immune response than does the construct with both the signal and anchor regions. The anchor region may be necessary for proper protein conformation which is necessary for a high immune response.

Immunofluoresence data illustrate that antibodies induced by the MSA1C-(Si,nA) and MSA1C-(Si,A) constructs recognize the parasite in vitro. This indicates that the recombinant protein expressed by the vaccinia virus is indeed very similar, if not identical, to the native parasite MSA1 C-terminus. Antibodies targeting the vaccinia viruses indicate that all four recombinant virus constructs as well as WR were administered at approximately the same level. Therefore the differences of the antibody responses of these four constructs is due to the primary sequence of the protein, not varying levels of vaccinia virus. The recombinant protein containing both the signal and anchor regions elicits the greatest immune response and this suggests that both the signal and anchor sequences are advantageous for optimal expression of the MSA-1 C-terminal region. Furthermore, antibodies to the protein containing both the signal and anchor sequences most effectively inhibit invasion of erythorcytes by parasites. Although 62% inhibition of invasion may seem only a partial inhibition, these invasion assays were conducted with a 3% starting parasitemia, whereas most other studies are done at approximately 0.3%. A higher starting parasitemia may reduce the inhibition because of the large numbers of merozoites released.

This study has shown that the MSA1C-(Si,A) construct expresses a functional protein which possesses the proper signal sequence and the proper anchor sequence for correct cell surface expression. Furthermore, the antibodies produced by mice and rabbits immunized uith the recombinant vaccinia virus are able to block parasite invasion in vitro.

DEPOSITS

The following have been deposited with the American type Culture Collection located at 12301 Parklawn Drive, Rockville, Md. 20852 pursuant to the Budapest Treaty for the International Recognition of the Deposit of Microorganisms for the Purpose of Patent Procedure. All restrictions on the availability of the materials deposited will be irrevocably removed upon the issuance of a patent thereon.

| Microorganism | ATCC Designation |
|---|---|
| Recombinant Vaccinia Virus r.v.v-MSA.C (Si,A) | VR-2518 |

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. An immunogenic composition comprising a pharmaceutically acceptable carrier and a vaccinia virus expression vector comprising a nucleotide sequence which encodes for an immunogenic MSA1 peptide operably linked to a signal sequence and an anchor sequence, wherein said signal sequence is SEQ ID NO:6 expressed at the N-terminus of the MSA1 peptide and said anchor sequence is SEQ ID NO:8 expressed at or near the carboxy-terminus of said MSA1 peptide.

2. The immunogenic composition according to claim 1, wherein said MSA1 peptide is a carboxy-terminal MSA1 peptide of SEQ ID NO:2.

3. A method of eliciting an immune response against a MSA1 peptide in a patient, comprising administering to a patient an effective amount of a recombinant vaccinia virus capable of expressing an immunogenic MSA1 peptide operably linked to a signal sequence and an anchor sequence, wherein said signal sequence is SEQ ID NO:6 expressed at the N-terminus of the MSA1 peptide and said anchor sequence is SEQ ID NO:8 expressed at or near the carboxy-terminus of said MSA1 peptide.

4. The method of claim 3, wherein said MSA1 peptide is a carboxy-terminal MSA1 peptide of SEQ ID NO:2.

5. The method of claim 3, wherein said patient is a human.

6. The method of claim 3, wherein said vaccinia virus is administered in combination with a pharmaceutically acceptable excipient, carrier or additive.

7. An expression vector comprising a nucleotide sequence which encodes for an immunogenic MSA1 peptide operably linked to a signal sequence and an anchor sequence, wherein said signal sequence is SEQ ID NO:6 expressed at the N-terminus of the MSA1 peptide and said anchor sequence is SEQ ID NO:8 expressed at or near the carboxy-terminus of said MSA 1 peptide.

8. The expression vector according to claim 7, wherein said MSA1 peptide is a carboxy-terminal MSA1 peptide of SEQ ID NO:2.

* * * * *

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 1785 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (vi) ORIGINAL SOURCE:
      (A) ORGANISM: Plasmodium falciparum

```
    (vii) IMMEDIATE SOURCE:
          (B) CLONE: MSA1 from GCG databank, Accession No. X02919

(ix) FEATURE:
          (A) NAME/KEY: CDS
          (B) LOCATION: 1..1785
          (C) IDENTIFICATION METHOD: experimental
          (D) OTHER INFORMATION: /partial
              /function= "preferred target for the development of an
              immune response" /product= "c-terminal fragment of MSA1
              protein" /evidence= EXPERIMENTAL /note= "This peptide
              corresponds to amino acids 1047 to 1640 of the major
              merozoite surface antigen 1 of the merozoite stage of
              Plasmodium falciparum."

(xi) SEQUENCE DESCRIPTION: SEQ ID NO: 1:

TTG AAT TCA CTT AAT AAC CCA AAG CAT GTA TTA CAA AAC TTT TCT GTT           48
Leu Asn Ser Leu Asn Asn Pro Lys His Val Leu Gln Asn Phe Ser Val
 1               5                  10                  15

TTC TTT AAC AAA AAA AAA GAA GCT GAA ATA GCA GAA ACT GAA AAC ACA           96
Phe Phe Asn Lys Lys Lys Glu Ala Glu Ile Ala Glu Thr Glu Asn Thr
                20                  25                  30

TTA GAA AAC ACA AAA ATA TTA TTG AAA CAT TAT AAA GGA CTT GTT AAA          144
Leu Glu Asn Thr Lys Ile Leu Leu Lys His Tyr Lys Gly Leu Val Lys
            35                  40                  45

TAT TAT AAT GGT GAA TCA TCT CCA TTA AAA ACT TTA AGT GAA GAA TCA          192
Tyr Tyr Asn Gly Glu Ser Ser Pro Leu Lys Thr Leu Ser Glu Glu Ser
 50                  55                  60

ATT CAA ACA GAA GAT AAT TAT GCC AGT TTA GAA AAC TTT AAA GTA TTA          240
Ile Gln Thr Glu Asp Asn Tyr Ala Ser Leu Glu Asn Phe Lys Val Leu
 65                  70                  75                  80

AGT AAA TTA GAA GGA AAA TTA AAG GAT AAT TTA AAT TTA GAA AAG AAA          288
Ser Lys Leu Glu Gly Lys Leu Lys Asp Asn Leu Asn Leu Glu Lys Lys
                85                  90                  95

AAA TTA TCA TAC TTA TCA AGT GGA TTA CAT CAT TTA ATT GCT GAA TTA          336
Lys Leu Ser Tyr Leu Ser Ser Gly Leu His His Leu Ile Ala Glu Leu
                100                 105                 110

AAA GAA GTA ATA AAA AAT AAA AAT TAT ACA GGT AAT TCT CCA AGT GAA          384
Lys Glu Val Ile Lys Asn Lys Asn Tyr Thr Gly Asn Ser Pro Ser Glu
            115                 120                 125

AAT AAT ACG GAT GTT AAC AAT GCA TTA GAA TCT TAC AAA AAA TTT CTC          432
Asn Asn Thr Asp Val Asn Asn Ala Leu Glu Ser Tyr Lys Lys Phe Leu
130                 135                 140

CCA GAA GGA ACA GAT GTT GCA ACA GTT GTA AGT GAA AGT GGA TCC GAC          480
Pro Glu Gly Thr Asp Val Ala Thr Val Val Ser Glu Ser Gly Ser Asp
145                 150                 155                 160

ACA TTA GAA CAA AGT CAA CCA AAG AAA CCA GCA TCA ACT CAT GTA GGA          528
Thr Leu Glu Gln Ser Gln Pro Lys Lys Pro Ala Ser Thr His Val Gly
                165                 170                 175

GCA GAG TCT AAC ACA ATA ACA ACA TCA CAA AAT GTC GAT GAT GAA GTA          576
Ala Glu Ser Asn Thr Ile Thr Thr Ser Gln Asn Val Asp Asp Glu Val
            180                 185                 190

GAT GAC GTA ATC ATA GTA CCT ATA TTT GGA GAA TCC GAA GAA GAT TAT          624
Asp Asp Val Ile Ile Val Pro Ile Phe Gly Glu Ser Glu Glu Asp Tyr
            195                 200                 205

GAT GAT TTA GGA CAA GTA GTA ACA GGA GAA GCA GTA ACT CCT TCC GTA          672
Asp Asp Leu Gly Gln Val Val Thr Gly Glu Ala Val Thr Pro Ser Val
210                 215                 220

ATT GAT AAC ATA CTT TCT AAA ATT GAA AAT GAA TAT GAG GTT TTA TAT          720
Ile Asp Asn Ile Leu Ser Lys Ile Glu Asn Glu Tyr Glu Val Leu Tyr
225                 230                 235                 240

TTA AAA CCT TTA GCA GGT GTT TAT AGA AGT TTA AAA AAA CAA TTA GAA          768
Leu Lys Pro Leu Ala Gly Val Tyr Arg Ser Leu Lys Lys Gln Leu Glu
```

```
                245                    250                      255
AAT AAC GTT ATG ACA TTT AAT GTT AAT GTT AAG GAT ATT TTA AAT TCA       816
Asn Asn Val Met Thr Phe Asn Val Asn Val Lys Asp Ile Leu Asn Ser
            260                 265                 270

CGA TTT AAT AAA CGT GAA AAT TTC AAA AAT GTT TTA GAA TCA GAT TTA       864
Arg Phe Asn Lys Arg Glu Asn Phe Lys Asn Val Leu Glu Ser Asp Leu
            275                 280                 285

ATT CCA TAT AAA GAT TTA ACA TCA AGT AAT TAT GTT GTC AAA GAT CCA       912
Ile Pro Tyr Lys Asp Leu Thr Ser Ser Asn Tyr Val Val Lys Asp Pro
            290                 295                 300

TAT AAA TTT CTT AAT AAA GAA AAA AGA GAT AAA TTC TTA AGC AGT TAT       960
Tyr Lys Phe Leu Asn Lys Glu Lys Arg Asp Lys Phe Leu Ser Ser Tyr
305                 310                 315                 320

AAT TAT ATT AAG GAT TCA ATA GAT ACG CAT ATA AAT TTT GCA AAT GAT      1008
Asn Tyr Ile Lys Asp Ser Ile Asp Thr His Ile Asn Phe Ala Asn Asp
                325                 330                 335

GTT CTT GGA TAT TAT AAA ATA TTA TCC GAA AAA TAT AAA TCA GAT TTA      1056
Val Leu Gly Tyr Tyr Lys Ile Leu Ser Glu Lys Tyr Lys Ser Asp Leu
                340                 345                 350

GAT TCA ATT AAA AAA TAT ATC AAC GAC AAA CAA GGT GAA AAT GAG AAA      1104
Asp Ser Ile Lys Lys Tyr Ile Asn Asp Lys Gln Gly Glu Asn Glu Lys
            355                 360                 365

TAC CTT CCC TTT TTA AAC AAT ATT GAG ACC TTA TAT AAA ACA GTT AAT      1152
Tyr Leu Pro Phe Leu Asn Asn Ile Glu Thr Leu Tyr Lys Thr Val Asn
            370                 375                 380

GAT AAA ATT GAT TTA TTT GTA ATT CAT TTA GAA GCA AAA GTT CTA AAT      1200
Asp Lys Ile Asp Leu Phe Val Ile His Leu Glu Ala Lys Val Leu Asn
385                 390                 395                 400

TAT ACA TAT GAG AAA TCA AAC GTA GAA GTT AAA ATA AAA GAA CTT AAT      1248
Tyr Thr Tyr Glu Lys Ser Asn Val Glu Val Lys Ile Lys Glu Leu Asn
                405                 410                 415

TAC TTA AAA ACA ATT CAA GAC AAA TTG GCA GAT TTT AAA AAA AAT AAC      1296
Tyr Leu Lys Thr Ile Gln Asp Lys Leu Ala Asp Phe Lys Lys Asn Asn
                420                 425                 430

AAT TTC GTT GGA ATT GCT GAT TTA TCA ACA GAT TAT AAC CAT AAT AAC      1344
Asn Phe Val Gly Ile Ala Asp Leu Ser Thr Asp Tyr Asn His Asn Asn
            435                 440                 445

TTA TTG ACA AAG TTC CTT AGT ACA GGT ATG GTT TTT GAA AAT CTT GCT      1392
Leu Leu Thr Lys Phe Leu Ser Thr Gly Met Val Phe Glu Asn Leu Ala
            450                 455                 460

AAA ACC GTT TTA TCT AAT TTA CTT GAT GGA AAC TTG CAA GGT ATG TTA      1440
Lys Thr Val Leu Ser Asn Leu Leu Asp Gly Asn Leu Gln Gly Met Leu
465                 470                 475                 480

AAC ATT TCA CAA CAC CAA TGC GTA AAA AAA CAA TGT CCA CAA AAT TCT      1488
Asn Ile Ser Gln His Gln Cys Val Lys Lys Gln Cys Pro Gln Asn Ser
                485                 490                 495

GGA TGT TTC AGA CAT TTA GAT GAA AGA GAA GAA TGT AAA TGT TTA TTA      1536
Gly Cys Phe Arg His Leu Asp Glu Arg Glu Glu Cys Lys Cys Leu Leu
                500                 505                 510

AAT TAC AAA CAA GAA GGT GAT AAA TGT GTT GAA AAT CCA AAT CCT ACT      1584
Asn Tyr Lys Gln Glu Gly Asp Lys Cys Val Glu Asn Pro Asn Pro Thr
            515                 520                 525

TGT AAC GAA AAT AAT GGT GGA TGT GAT GCA GAT GCC AAA TGT ACC GAA      1632
Cys Asn Glu Asn Asn Gly Gly Cys Asp Ala Asp Ala Lys Cys Thr Glu
            530                 535                 540

GAA GAT TCA GGT AGC AAC GGA AAG AAA ATC ACA TGT GAA TGT ACT AAA      1680
Glu Asp Ser Gly Ser Asn Gly Lys Lys Ile Thr Cys Glu Cys Thr Lys
545                 550                 555                 560

CCT GAT TCT TAT CCA CTT TTC GAT GGT ATT TTC TGC AGT TCC TCT AAC      1728
```

-continued

```
Pro Asp Ser Tyr Pro Leu Phe Asp Gly Ile Phe Cys Ser Ser Ser Asn
            565                 570                 575

TTC TTA GGA ATA TCA TTC TTA TTA ATA CTC ATG TTA ATA TTA TAC AGT        1776
Phe Leu Gly Ile Ser Phe Leu Leu Ile Leu Met Leu Ile Leu Tyr Ser
            580                 585                 590

TTC ATT TAA                                                            1785
Phe Ile *
        595
```

(2) INFORMATION FOR SEQ ID NO: 2:

(i) SEQUENCE CHARACTERISTICS:
        (A) LENGTH: 594 amino acids
        (B) TYPE: amino acid
        (D) TOPOLOGY: linear (ii) MOLECULE TYPE: protein (xi) SEQUENCE DESCRIPTION: SEQ ID NO: 2:

```
Leu Asn Ser Leu Asn Asn Pro Lys His Val Leu Gln Asn Phe Ser Val
 1               5                  10                  15

Phe Phe Asn Lys Lys Lys Glu Ala Glu Ile Ala Glu Thr Glu Asn Thr
            20                  25                  30

Leu Glu Asn Thr Lys Ile Leu Leu Lys His Tyr Lys Gly Leu Val Lys
            35                  40                  45

Tyr Tyr Asn Gly Glu Ser Ser Pro Leu Lys Thr Leu Ser Glu Glu Ser
 50                  55                  60

Ile Gln Thr Glu Asp Asn Tyr Ala Ser Leu Glu Asn Phe Lys Val Leu
 65                  70                  75                  80

Ser Lys Leu Glu Gly Lys Leu Lys Asp Asn Leu Asn Leu Glu Lys Lys
            85                  90                  95

Lys Leu Ser Tyr Leu Ser Ser Gly Leu His His Leu Ile Ala Glu Leu
            100                 105                 110

Lys Glu Val Ile Lys Asn Lys Asn Tyr Thr Gly Asn Ser Pro Ser Glu
            115                 120                 125

Asn Asn Thr Asp Val Asn Asn Ala Leu Glu Ser Tyr Lys Lys Phe Leu
            130                 135                 140

Pro Glu Gly Thr Asp Val Ala Thr Val Val Ser Glu Ser Gly Ser Asp
145                 150                 155                 160

Thr Leu Glu Gln Ser Gln Pro Lys Lys Pro Ala Ser Thr His Val Gly
                165                 170                 175

Ala Glu Ser Asn Thr Ile Thr Thr Ser Gln Asn Val Asp Asp Glu Val
            180                 185                 190

Asp Asp Val Ile Ile Val Pro Ile Phe Gly Glu Ser Glu Glu Asp Tyr
            195                 200                 205

Asp Asp Leu Gly Gln Val Thr Gly Glu Ala Val Thr Pro Ser Val
            210                 215                 220

Ile Asp Asn Ile Leu Ser Lys Ile Glu Asn Glu Tyr Glu Val Leu Tyr
225                 230                 235                 240

Leu Lys Pro Leu Ala Gly Val Tyr Arg Ser Leu Lys Lys Gln Leu Glu
                245                 250                 255

Asn Asn Val Met Thr Phe Asn Val Asn Val Lys Asp Ile Leu Asn Ser
            260                 265                 270

Arg Phe Asn Lys Arg Glu Asn Phe Lys Asn Val Leu Glu Ser Asp Leu
            275                 280                 285

Ile Pro Tyr Lys Asp Leu Thr Ser Ser Asn Tyr Val Lys Asp Pro
            290                 295                 300
```

```
Tyr Lys Phe Leu Asn Lys Glu Lys Arg Asp Lys Phe Leu Ser Ser Tyr
305                 310                 315                 320

Asn Tyr Ile Lys Asp Ser Ile Asp Thr His Ile Asn Phe Ala Asn Asp
            325                 330                 335

Val Leu Gly Tyr Tyr Lys Ile Leu Ser Glu Lys Tyr Lys Ser Asp Leu
                340                 345                 350

Asp Ser Ile Lys Lys Tyr Ile Asn Asp Lys Gln Gly Glu Asn Glu Lys
            355                 360                 365

Tyr Leu Pro Phe Leu Asn Asn Ile Glu Thr Leu Tyr Lys Thr Val Asn
370                 375                 380

Asp Lys Ile Asp Leu Phe Val Ile His Leu Glu Ala Lys Val Leu Asn
385                 390                 395                 400

Tyr Thr Tyr Glu Lys Ser Asn Val Glu Val Lys Ile Lys Glu Leu Asn
                405                 410                 415

Tyr Leu Lys Thr Ile Gln Asp Lys Leu Ala Asp Phe Lys Lys Asn Asn
            420                 425                 430

Asn Phe Val Gly Ile Ala Asp Leu Ser Thr Asp Tyr Asn His Asn Asn
            435                 440                 445

Leu Leu Thr Lys Phe Leu Ser Thr Gly Met Val Phe Glu Asn Leu Ala
            450                 455                 460

Lys Thr Val Leu Ser Asn Leu Leu Asp Gly Asn Leu Gln Gly Met Leu
465                 470                 475                 480

Asn Ile Ser Gln His Gln Cys Val Lys Lys Gln Cys Pro Gln Asn Ser
            485                 490                 495

Gly Cys Phe Arg His Leu Asp Glu Arg Glu Glu Cys Lys Cys Leu Leu
            500                 505                 510

Asn Tyr Lys Gln Glu Gly Asp Lys Cys Val Glu Asn Pro Asn Pro Thr
            515                 520                 525

Cys Asn Glu Asn Asn Gly Gly Cys Asp Ala Asp Ala Lys Cys Thr Glu
            530                 535                 540

Glu Asp Ser Gly Ser Asn Gly Lys Lys Ile Thr Cys Glu Cys Thr Lys
545                 550                 555                 560

Pro Asp Ser Tyr Pro Leu Phe Asp Gly Ile Phe Cys Ser Ser Ser Asn
                565                 570                 575

Phe Leu Gly Ile Ser Phe Leu Leu Ile Leu Met Leu Ile Leu Tyr Ser
            580                 585                 590

Phe Ile
594

(2) INFORMATION FOR SEQ ID NO: 3:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
        (A) ORGANISM: Plasmodium falciparum (vii) IMMEDIATE SOURCE:
```

(A) LIBRARY: GCG database, Accession No. X02919
        (B) CLONE: MSA1

(ix) FEATURE:
        (A) NAME/KEY: sig_peptide
        (B) LOCATION: 1..57

(ix) FEATURE:
        (A) NAME/KEY: CDS
        (B) LOCATION: 1..57

(xi) SEQUENCE DESCRIPTION: SEQ ID NO: 3:

```
ATG AAG ATC ATA TTC TTT TTA TGT TCA TTT CTT TTT TTT ATT ATA AAT      48
Met Lys Ile Ile Phe Phe Leu Cys Ser Phe Leu Phe Phe Ile Ile Asn
 1               5                  10                  15

ACA CAA TGT                                                          57
Thr Gln Cys
        19
```

(2) INFORMATION FOR SEQ ID NO: 4:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Ile Ile Phe Phe Leu Cys Ser Phe Leu Phe Phe Ile Ile Asn
 1               5                  10                  15

Thr Gln Cys
        19
```

(2) INFORMATION FOR SEQ ID NO: 5:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
        (A) ORGANISM: Plasmodium falciparum (vii) IMMEDIATE SOURCE:
        (A) LIBRARY: GCG database, Accession No. X02919
        (B) CLONE: MSA1

(ix) FEATURE:
        (A) NAME/KEY: sig_peptide
        (B) LOCATION: 1..165

(ix) FEATURE:
        (A) NAME/KEY: CDS
        (B) LOCATION: 1..165

(xi) SEQUENCE DESCRIPTION: SEQ ID NO: 5:

```
ATG AAG ATC ATA TTC TTT TTA TGT TCA TTT CTT TTT TTT ATT ATA AAT      48
Met Lys Ile Ile Phe Phe Leu Cys Ser Phe Leu Phe Phe Ile Ile Asn
 1               5                  10                  15

ACA CAA TGT GTA ACA CAT GAA AGT TAT CAA GAA CTT GTC AAA AAA CTA      96
Thr Gln Cys Val Thr His Glu Ser Tyr Gln Glu Leu Val Lys Lys Leu
```

```
                       20                  25                  30
GAA GCT TTA GAA GAT GCA GTA TTG ACA GGT TAT AGT TTA TTT CAA AAG      144
Glu Ala Leu Glu Asp Ala Val Leu Thr Gly Tyr Ser Leu Phe Gln Lys
            35                  40                  45

GAA AAA ATG GTA TTA AAT GAA                                          165
Glu Lys Met Val Leu Asn Glu
    50                  55
```

(2) INFORMATION FOR SEQ ID NO: 6:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Ile Ile Phe Phe Leu Cys Ser Phe Leu Phe Phe Ile Ile Asn
1               5                   10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
            35                  40                  45

Glu Lys Met Val Leu Asn Glu
    50                  55
```

(2) INFORMATION FOR SEQ ID NO: 7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (vi) ORIGINAL SOURCE:
        (A) ORGANISM: Plasmodium falciparum (vii) IMMEDIATE SOURCE:
        (A) LIBRARY: GCG database, Accession No. X02919
        (B) CLONE: MSA1

(ix) FEATURE:
        (A) NAME/KEY: misc_feature
        (B) LOCATION: 1..57
        (D) OTHER INFORMATION: /product= "anchor peptide"
           /label= anchor_peptide (ix) FEATURE:
        (A) NAME/KEY: CDS
        (B) LOCATION: 1..57

(xi) SEQUENCE DESCRIPTION: SEQ ID NO: 7:

```
TTC TTA GGA ATA TCA TTC TTA TTA ATA CTC ATG TTA ATA TTA TAC AGT       48
Phe Leu Gly Ile Ser Phe Leu Leu Ile Leu Met Leu Ile Leu Tyr Ser
1               5                   10                  15

TTC ATT TAA                                                           57
Phe Ile *
```

(2) INFORMATION FOR SEQ ID NO: 8:

(i) SEQUENCE CHARACTERISTICS:
            (A) LENGTH: 18 amino acids
            (B) TYPE: amino acid
            (D) TOPOLOGY: linear (ii) MOLECULE TYPE: protein (xi) SEQUENCE DESCRIPTION: SEQ ID NO: 8:

Phe Leu Gly Ile Ser Phe Leu Leu Ile Leu Met Leu Ile Leu Tyr Ser
 1               5                  10                  15

Phe Ile
    18

(2) INFORMATION FOR SEQ ID NO: 9:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer 1"

(iii) HYPOTHETICAL: YES (iv) ANTI-SENSE: NO (vi) ORIGINAL SOURCE:
            (A) ORGANISM: Plasmodium falciparum (vii) IMMEDIATE SOURCE:
            (A) LIBRARY: GCG database, Accession No. X02919
            (B) CLONE: MSA1

(xi) SEQUENCE DESCRIPTION: SEQ ID NO: 9:

GCGTCGACAT GAAGATCATA TTCTTTTTA                                                29

(2) INFORMATION FOR SEQ ID NO: 10:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer 2"

(iii) HYPOTHETICAL: YES (iv) ANTI-SENSE: NO (vi) ORIGINAL SOURCE:
            (A) ORGANISM: Plasmodium falciparum (vii) IMMEDIATE SOURCE:
            (A) LIBRARY: GCG database, Accession No. X02919
            (B) CLONE: MSA1

(xi) SEQUENCE DESCRIPTION: SEQ ID NO: 10:

GCGAATTCAA TTCATTTAAT ACCATTTTTT C                                             31

(2) INFORMATION FOR SEQ ID NO: 11:

(i) SEQUENCE CHARACTERISTICS:
            (A) LENGTH: 29 base pairs
            (B) TYPE: nucleic acid
            (C) STRANDEDNESS: single
            (D) TOPOLOGY: linear

```
        (ii) MOLECULE TYPE: other nucleic acid
             (A) DESCRIPTION: /desc = "PCR primer 3"

(iii) HYPOTHETICAL: YES (iv) ANTI-SENSE: NO (vi) ORIGINAL SOURCE:
             (A) ORGANISM: Plasmodium falciparum (vii) IMMEDIATE SOURCE:
             (A) LIBRARY: GCG database, Accession No. X02919
             (B) CLONE: MSA1

(xi) SEQUENCE DESCRIPTION: SEQ ID NO: 11:

GCGAATTCAC TTAATAACCC AAAGCATGT                                              29

(2) INFORMATION FOR SEQ ID NO: 12:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PCR primer 4"

(iii) HYPOTHETICAL: YES (iv) ANTI-SENSE: NO (vi) ORIGINAL SOURCE:
             (A) ORGANISM: Plasmodium falciparum (vii) IMMEDIATE SOURCE:
             (A) LIBRARY: GCG database, Accession No. X02919
             (B) CLONE: MSA1

(xi) SEQUENCE DESCRIPTION: SEQ ID NO: 12:

GCGGTACCTT AAATGAAACT GTATAATAT                                              29

(2) INFORMATION FOR SEQ ID NO: 13:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PCR primer 5"

(iii) HYPOTHETICAL: YES (iv) ANTI-SENSE: NO (vi) ORIGINAL SOURCE:
             (A) ORGANISM: Plasmodium falciparum (vii) IMMEDIATE SOURCE:
             (A) LIBRARY: GCG database, Accession No. X02919
             (B) CLONE: MSA1

(xi) SEQUENCE DESCRIPTION: SEQ ID NO: 13:

GCGGTACCTT AGTTAGAGGA ACTGCAGAAA AT                                          32

(2) INFORMATION FOR SEQ ID NO: 14:

(i) SEQUENCE CHARACTERISTICS:
             (A) LENGTH: 32 base pairs
             (B) TYPE: nucleic acid
             (C) STRANDEDNESS: single
```

(D) TOPOLOGY: linear (ii) MOLECULE TYPE: other nucleic acid
        (A) DESCRIPTION: /desc = "PCR primer 6"

(iii) HYPOTHETICAL: YES (iv) ANTI-SENSE: NO (vi) ORIGINAL SOURCE:
        (A) ORGANISM: Plasmodium falciparum (vii) IMMEDIATE SOURCE:
        (A) LIBRARY: GCG database, Accession No. X02919
        (B) CLONE: MSA1

(xi) SEQUENCE DESCRIPTION: SEQ ID NO: 14:

```
GCGTCGACAT GGTAACACAT GAAAGTTATC AA                                    32
```

(2) INFORMATION FOR SEQ ID NO: 15:

(i) SEQUENCE CHARACTERISTICS:
        (A) LENGTH: 1950 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Plasmodium falciparum (vii) IMMEDIATE SOURCE:
        (B) CLONE: MSA1C-(Si,A)

(ix) FEATURE:
        (A) NAME/KEY: CDS
        (B) LOCATION: 1..1950

(ix) FEATURE:
        (A) NAME/KEY: sig_peptide
        (B) LOCATION: 1..165

(ix) FEATURE:
        (A) NAME/KEY: misc_feature
        (B) LOCATION: 1894..1950
        (D) OTHER INFORMATION: /product= "anchor peptide"
            /label= anchor_peptide (xi) SEQUENCE DESCRIPTION: SEQ ID NO: 15:

```
ATG AAG ATC ATA TTC TTT TTA TGT TCA TTT CTT TTT TTT ATT ATA AAT        48
Met Lys Ile Ile Phe Phe Leu Cys Ser Phe Leu Phe Phe Ile Ile Asn
 1               5                  10                  15

ACA CAA TGT GTA ACA CAT GAA AGT TAT CAA GAA CTT GTC AAA AAA CTA        96
Thr Gln Cys Val Thr His Glu Ser Tyr Gln Glu Leu Val Lys Lys Leu
                20                  25                  30

GAA GCT TTA GAA GAT GCA GTA TTG ACA GGT TAT AGT TTA TTT CAA AAG       144
Glu Ala Leu Glu Asp Ala Val Leu Thr Gly Tyr Ser Leu Phe Gln Lys
            35                  40                  45

GAA AAA ATG GTA TTA AAT GAA TTG AAT TCA CTT AAT AAC CCA AAG CAT       192
Glu Lys Met Val Leu Asn Glu Leu Asn Ser Leu Asn Asn Pro Lys His
    50                  55                  60

GTA TTA CAA AAC TTT TCT GTT TTC TTT AAC AAA AAA AAA GAA GCT GAA       240
Val Leu Gln Asn Phe Ser Val Phe Phe Asn Lys Lys Lys Glu Ala Glu
65                  70                  75                  80

ATA GCA GAA ACT GAA AAC ACA TTA GAA AAC ACA AAA ATA TTA TTG AAA       288
Ile Ala Glu Thr Glu Asn Thr Leu Glu Asn Thr Lys Ile Leu Leu Lys
```

```
                            85                  90                      95
CAT TAT AAA GGA CTT GTT AAA TAT TAT AAT GGT GAA TCA TCT CCA TTA           336
His Tyr Lys Gly Leu Val Lys Tyr Tyr Asn Gly Glu Ser Ser Pro Leu
                100                 105                 110

AAA ACT TTA AGT GAA GAA TCA ATT CAA ACA GAA GAT AAT TAT GCC AGT           384
Lys Thr Leu Ser Glu Glu Ser Ile Gln Thr Glu Asp Asn Tyr Ala Ser
            115                 120                 125

TTA GAA AAC TTT AAA GTA TTA AGT AAA TTA GAA GGA AAA TTA AAG GAT           432
Leu Glu Asn Phe Lys Val Leu Ser Lys Leu Glu Gly Lys Leu Lys Asp
        130                 135                 140

AAT TTA AAT TTA GAA AAG AAA AAA TTA TCA TAC TTA TCA AGT GGA TTA           480
Asn Leu Asn Leu Glu Lys Lys Lys Leu Ser Tyr Leu Ser Ser Gly Leu
145                 150                 155                 160

CAT CAT TTA ATT GCT GAA TTA AAA GAA GTA ATA AAA AAT AAA AAT TAT           528
His His Leu Ile Ala Glu Leu Lys Glu Val Ile Lys Asn Lys Asn Tyr
                165                 170                 175

ACA GGT AAT TCT CCA AGT GAA AAT AAT ACG GAT GTT AAC AAT GCA TTA           576
Thr Gly Asn Ser Pro Ser Glu Asn Asn Thr Asp Val Asn Asn Ala Leu
            180                 185                 190

GAA TCT TAC AAA AAA TTT CTC CCA GAA GGA ACA GAT GTT GCA ACA GTT           624
Glu Ser Tyr Lys Lys Phe Leu Pro Glu Gly Thr Asp Val Ala Thr Val
        195                 200                 205

GTA AGT GAA AGT GGA TCC GAC ACA TTA GAA CAA AGT CAA CCA AAG AAA           672
Val Ser Glu Ser Gly Ser Asp Thr Leu Glu Gln Ser Gln Pro Lys Lys
    210                 215                 220

CCA GCA TCA ACT CAT GTA GGA GCA GAG TCT AAC ACA ATA ACA ACA TCA           720
Pro Ala Ser Thr His Val Gly Ala Glu Ser Asn Thr Ile Thr Thr Ser
225                 230                 235                 240

CAA AAT GTC GAT GAT GAA GTA GAT GAC GTA ATC ATA GTA CCT ATA TTT           768
Gln Asn Val Asp Asp Glu Val Asp Asp Val Ile Ile Val Pro Ile Phe
                245                 250                 255

GGA GAA TCC GAA GAA GAT TAT GAT GAT TTA GGA CAA GTA GTA ACA GGA           816
Gly Glu Ser Glu Glu Asp Tyr Asp Asp Leu Gly Gln Val Val Thr Gly
            260                 265                 270

GAA GCA GTA ACT CCT TCC GTA ATT GAT AAC ATA CTT TCT AAA ATT GAA           864
Glu Ala Val Thr Pro Ser Val Ile Asp Asn Ile Leu Ser Lys Ile Glu
        275                 280                 285

AAT GAA TAT GAG GTT TTA TAT TTA AAA CCT TTA GCA GGT GTT TAT AGA           912
Asn Glu Tyr Glu Val Leu Tyr Leu Lys Pro Leu Ala Gly Val Tyr Arg
    290                 295                 300

AGT TTA AAA AAA CAA TTA GAA AAT AAC GTT ATG ACA TTT AAT GTT AAT           960
Ser Leu Lys Lys Gln Leu Glu Asn Asn Val Met Thr Phe Asn Val Asn
305                 310                 315                 320

GTT AAG GAT ATT TTA AAT TCA CGA TTT AAT AAA CGT GAA AAT TTC AAA          1008
Val Lys Asp Ile Leu Asn Ser Arg Phe Asn Lys Arg Glu Asn Phe Lys
                325                 330                 335

AAT GTT TTA GAA TCA GAT TTA ATT CCA TAT AAA GAT TTA ACA TCA AGT          1056
Asn Val Leu Glu Ser Asp Leu Ile Pro Tyr Lys Asp Leu Thr Ser Ser
            340                 345                 350

AAT TAT GTT GTC AAA GAT CCA TAT AAA TTT CTT AAT AAA GAA AAA AGA          1104
Asn Tyr Val Val Lys Asp Pro Tyr Lys Phe Leu Asn Lys Glu Lys Arg
        355                 360                 365

GAT AAA TTC TTA AGC AGT TAT AAT TAT ATT AAG GAT TCA ATA GAT ACG          1152
Asp Lys Phe Leu Ser Ser Tyr Asn Tyr Ile Lys Asp Ser Ile Asp Thr
    370                 375                 380

GAT ATA AAT TTT GCA AAT GAT GTT CTT GGA TAT TAT AAA ATA TTA TCC          1200
Asp Ile Asn Phe Ala Asn Asp Val Leu Gly Tyr Tyr Lys Ile Leu Ser
385                 390                 395                 400

GAA AAA TAT AAA TCA GAT TTA GAT TCA ATT AAA AAA TAT ATC AAC GAC          1248
```

```
Glu Lys Tyr Lys Ser Asp Leu Asp Ser Ile Lys Lys Tyr Ile Asn Asp
                405                 410                 415

AAA CAA GGT GAA AAT GAG AAA TAC CTT CCC TTT TTA AAC AAT ATT GAG      1296
Lys Gln Gly Glu Asn Glu Lys Tyr Leu Pro Phe Leu Asn Asn Ile Glu
            420                 425                 430

ACC TTA TAT AAA ACA GTT AAT GAT AAA ATT GAT TTA TTT GTA ATT CAT      1344
Thr Leu Tyr Lys Thr Val Asn Asp Lys Ile Asp Leu Phe Val Ile His
            435                 440                 445

TTA GAA GCA AAA GTT CTA AAT TAT ACA TAT GAG AAA TCA AAC GTA GAA      1392
Leu Glu Ala Lys Val Leu Asn Tyr Thr Tyr Glu Lys Ser Asn Val Glu
450                 455                 460

GTT AAA ATA AAA GAA CTT AAT TAC TTA AAA ACA ATT CAA GAC AAA TTG      1440
Val Lys Ile Lys Glu Leu Asn Tyr Leu Lys Thr Ile Gln Asp Lys Leu
465                 470                 475                 480

GCA GAT TTT AAA AAA AAT AAC AAT TTC GTT GGA ATT GCT GAT TTA TCA      1488
Ala Asp Phe Lys Lys Asn Asn Asn Phe Val Gly Ile Ala Asp Leu Ser
                485                 490                 495

ACA GAT TAT AAC CAT AAT AAC TTA TTG ACA AAG TTC CTT AGT ACA GGT      1536
Thr Asp Tyr Asn His Asn Asn Leu Leu Thr Lys Phe Leu Ser Thr Gly
            500                 505                 510

ATG GTT TTT GAA AAT CTT GCT AAA ACC GTT TTA TCT AAT TTA CTT GAT      1584
Met Val Phe Glu Asn Leu Ala Lys Thr Val Leu Ser Asn Leu Leu Asp
            515                 520                 525

GGA AAC TTG CAA GGT ATG TTA AAC ATT TCA CAA CAC CAA TGC GTA AAA      1632
Gly Asn Leu Gln Gly Met Leu Asn Ile Ser Gln His Gln Cys Val Lys
530                 535                 540

AAA CAA TGT CCA CAA AAT TCT GGA TGT TTC AGA CAT TTA GAT GAA AGA      1680
Lys Gln Cys Pro Gln Asn Ser Gly Cys Phe Arg His Leu Asp Glu Arg
545                 550                 555                 560

GAA GAA TGT AAA TGT TTA TTA AAT TAC AAA CAA GAA GGT GAT AAA TGT      1728
Glu Glu Cys Lys Cys Leu Leu Asn Tyr Lys Gln Glu Gly Asp Lys Cys
                565                 570                 575

GTT GAA AAT CCA AAT CCT ACT TGT AAC GAA AAT AAT GGT GGA TGT GAT      1776
Val Glu Asn Pro Asn Pro Thr Cys Asn Glu Asn Asn Gly Gly Cys Asp
            580                 585                 590

GCA GAT GCC AAA TGT ACC GAA GAA GAT TCA GGT AGC AAC GGA AAG AAA      1824
Ala Asp Ala Lys Cys Thr Glu Glu Asp Ser Gly Ser Asn Gly Lys Lys
            595                 600                 605

ATC ACA TGT GAA TGT ACT AAA CCT GAT TCT TAT CCA CTT TTC GAT GGT      1872
Ile Thr Cys Glu Cys Thr Lys Pro Asp Ser Tyr Pro Leu Phe Asp Gly
610                 615                 620

ATT TTC TGC AGT TCC TCT AAC TTC TTA GGA ATA TCA TTC TTA TTA ATA      1920
Ile Phe Cys Ser Ser Ser Asn Phe Leu Gly Ile Ser Phe Leu Leu Ile
625                 630                 635                 640

CTC ATG TTA ATA TTA TAC AGT TTC ATT TAA                              1950
Leu Met Leu Ile Leu Tyr Ser Phe Ile *
                645                 650

(2) INFORMATION FOR SEQ ID NO: 16:

(i) SEQUENCE CHARACTERISTICS:
        (A) LENGTH: 649 amino acids
        (B) TYPE: amino acid
        (D) TOPOLOGY: linear (ii) MOLECULE TYPE: protein (xi) SEQUENCE DESCRIPTION: SEQ ID NO: 16:

Met Lys Ile Ile Phe Phe Leu Cys Ser Phe Leu Phe Phe Ile Ile Asn
  1               5                  10                  15

Thr Gln Cys Val Thr His Glu Ser Tyr Gln Glu Leu Val Lys Lys Leu
```

-continued

```
                20                  25                  30
Glu Ala Leu Glu Asp Ala Val Leu Thr Gly Tyr Ser Leu Phe Gln Lys
             35                  40                  45
Glu Lys Met Val Leu Asn Glu Leu Asn Ser Leu Asn Asn Pro Lys His
         50                  55                  60
Val Leu Gln Asn Phe Ser Val Phe Phe Asn Lys Lys Glu Ala Glu
 65                  70                  75                  80
Ile Ala Glu Thr Glu Asn Thr Leu Glu Asn Thr Lys Ile Leu Leu Lys
                 85                  90                  95
His Tyr Lys Gly Leu Val Lys Tyr Tyr Asn Gly Glu Ser Ser Pro Leu
            100                 105                 110
Lys Thr Leu Ser Glu Glu Ser Ile Gln Thr Glu Asp Asn Tyr Ala Ser
            115                 120                 125
Leu Glu Asn Phe Lys Val Leu Ser Lys Leu Glu Gly Lys Leu Lys Asp
        130                 135                 140
Asn Leu Asn Leu Glu Lys Lys Leu Ser Tyr Leu Ser Ser Gly Leu
145                 150                 155                 160
His His Leu Ile Ala Glu Leu Lys Glu Val Ile Lys Asn Lys Asn Tyr
            165                 170                 175
Thr Gly Asn Ser Pro Ser Glu Asn Asn Thr Asp Val Asn Asn Ala Leu
            180                 185                 190
Glu Ser Tyr Lys Lys Phe Leu Pro Glu Gly Thr Asp Val Ala Thr Val
        195                 200                 205
Val Ser Glu Ser Gly Ser Asp Thr Leu Glu Gln Ser Gln Pro Lys Lys
        210                 215                 220
Pro Ala Ser Thr His Val Gly Ala Glu Ser Asn Thr Ile Thr Thr Ser
225                 230                 235                 240
Gln Asn Val Asp Asp Glu Val Asp Val Ile Ile Val Pro Ile Phe
            245                 250                 255
Gly Glu Ser Glu Glu Asp Tyr Asp Asp Leu Gly Gln Val Val Thr Gly
            260                 265                 270
Glu Ala Val Thr Pro Ser Val Ile Asp Asn Ile Leu Ser Lys Ile Glu
        275                 280                 285
Asn Glu Tyr Glu Val Leu Tyr Leu Lys Pro Leu Ala Gly Val Tyr Arg
        290                 295                 300
Ser Leu Lys Lys Gln Leu Glu Asn Asn Val Met Thr Phe Asn Val Asn
305                 310                 315                 320
Val Lys Asp Ile Leu Asn Ser Arg Phe Asn Lys Arg Glu Asn Phe Lys
            325                 330                 335
Asn Val Leu Glu Ser Asp Leu Ile Pro Tyr Lys Asp Leu Thr Ser Ser
        340                 345                 350
Asn Tyr Val Val Lys Asp Pro Tyr Lys Phe Leu Asn Lys Glu Lys Arg
        355                 360                 365
Asp Lys Phe Leu Ser Ser Tyr Asn Tyr Ile Lys Asp Ser Ile Asp Thr
    370                 375                 380
Asp Ile Asn Phe Ala Asn Asp Val Leu Gly Tyr Tyr Lys Ile Leu Ser
385                 390                 395                 400
Glu Lys Tyr Lys Ser Asp Leu Asp Ser Ile Lys Lys Tyr Ile Asn Asp
            405                 410                 415
Lys Gln Gly Glu Asn Glu Lys Tyr Leu Pro Phe Leu Asn Asn Ile Glu
        420                 425                 430
Thr Leu Tyr Lys Thr Val Asn Asp Lys Ile Asp Leu Phe Val Ile His
        435                 440                 445
```

-continued

```
Leu Glu Ala Lys Val Leu Asn Tyr Thr Tyr Glu Lys Ser Asn Val Glu
    450                 455                 460

Val Lys Ile Lys Glu Leu Asn Tyr Leu Lys Thr Ile Gln Asp Lys Leu
465                 470                 475                 480

Ala Asp Phe Lys Lys Asn Asn Asn Phe Val Gly Ile Ala Asp Leu Ser
                485                 490                 495

Thr Asp Tyr Asn His Asn Asn Leu Leu Thr Lys Phe Leu Ser Thr Gly
            500                 505                 510

Met Val Phe Glu Asn Leu Ala Lys Thr Val Leu Ser Asn Leu Leu Asp
        515                 520                 525

Gly Asn Leu Gln Gly Met Leu Asn Ile Ser Gln His Gln Cys Val Lys
    530                 535                 540

Lys Gln Cys Pro Gln Asn Ser Gly Cys Phe Arg His Leu Asp Glu Arg
545                 550                 555                 560

Glu Glu Cys Lys Cys Leu Leu Asn Tyr Lys Gln Glu Gly Asp Lys Cys
                565                 570                 575

Val Glu Asn Pro Asn Pro Thr Cys Asn Glu Asn Asn Gly Gly Cys Asp
            580                 585                 590

Ala Asp Ala Lys Cys Thr Glu Glu Asp Ser Gly Ser Asn Gly Lys Lys
        595                 600                 605

Ile Thr Cys Glu Cys Thr Lys Pro Asp Ser Tyr Pro Leu Phe Asp Gly
    610                 615                 620

Ile Phe Cys Ser Ser Ser Asn Phe Leu Gly Ile Ser Phe Leu Leu Ile
625                 630                 635                 640

Leu Met Leu Ile Leu Tyr Ser Phe Ile
                645                 649
```

(2) INFORMATION FOR SEQ ID NO: 17:

(i) SEQUENCE CHARACTERISTICS:
        (A) LENGTH: 1896 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Plasmodium falciparum (vii) IMMEDIATE SOURCE:
        (B) CLONE: MSA1C-(Si,nA)

(ix) FEATURE:
        (A) NAME/KEY: CDS
        (B) LOCATION: 1..1896

(ix) FEATURE:
        (A) NAME/KEY: sig_peptide
        (B) LOCATION: 1..165

(xi) SEQUENCE DESCRIPTION: SEQ ID NO: 17:

```
ATG AAG ATC ATA TTC TTT TTA TGT TCA TTT CTT TTT TTT ATT ATA AAT    48
Met Lys Ile Ile Phe Phe Leu Cys Ser Phe Leu Phe Phe Ile Ile Asn
 1               5                  10                  15

ACA CAA TGT GTA ACA CAT GAA AGT TAT CAA GAA CTT GTC AAA AAA CTA    96
Thr Gln Cys Val Thr His Glu Ser Tyr Gln Glu Leu Val Lys Lys Leu
                20                  25                  30
```

| | | |
|---|---|---|
| GAA GCT TTA GAA GAT GCA GTA TTG ACA GGT TAT AGT TTA TTT CAA AAG<br>Glu Ala Leu Glu Asp Ala Val Leu Thr Gly Tyr Ser Leu Phe Gln Lys<br>         35                      40                       45 | 144 |
| GAA AAA ATG GTA TTA AAT GAA TTG AAT TCA CTT AAT AAC CCA AAG CAT<br>Glu Lys Met Val Leu Asn Glu Leu Asn Ser Leu Asn Asn Pro Lys His<br> 50                      55                       60 | 192 |
| GTA TTA CAA AAC TTT TCT GTT TTC TTT AAC AAA AAA AAA GAA GCT GAA<br>Val Leu Gln Asn Phe Ser Val Phe Phe Asn Lys Lys Lys Glu Ala Glu<br>65                  70                     75                    80 | 240 |
| ATA GCA GAA ACT GAA AAC ACA TTA GAA AAC ACA AAA ATA TTA TTG AAA<br>Ile Ala Glu Thr Glu Asn Thr Leu Glu Asn Thr Lys Ile Leu Leu Lys<br>               85                       90                      95 | 288 |
| CAT TAT AAA GGA CTT GTT AAA TAT TAT AAT GGT GAA TCA TCT CCA TTA<br>His Tyr Lys Gly Leu Val Lys Tyr Tyr Asn Gly Glu Ser Ser Pro Leu<br>          100                    105                 110 | 336 |
| AAA ACT TTA AGT GAA GAA TCA ATT CAA ACA GAA GAT AAT TAT GCC AGT<br>Lys Thr Leu Ser Glu Glu Ser Ile Gln Thr Glu Asp Asn Tyr Ala Ser<br>          115                    120                 125 | 384 |
| TTA GAA AAC TTT AAA GTA TTA AGT AAA TTA GAA GGA AAA TTA AAG GAT<br>Leu Glu Asn Phe Lys Val Leu Ser Lys Leu Glu Gly Lys Leu Lys Asp<br>    130                    135                    140 | 432 |
| AAT TTA AAT TTA GAA AAG AAA AAA TTA TCA TAC TTA TCA AGT GGA TTA<br>Asn Leu Asn Leu Glu Lys Lys Lys Leu Ser Tyr Leu Ser Ser Gly Leu<br>145                  150                    155                160 | 480 |
| CAT CAT TTA ATT GCT GAA TTA AAA GAA GTA ATA AAA AAT AAA AAT TAT<br>His His Leu Ile Ala Glu Leu Lys Glu Val Ile Lys Asn Lys Asn Tyr<br>          165                    170                 175 | 528 |
| ACA GGT AAT TCT CCA AGT GAA AAT AAT ACG GAT GTT AAC AAT GCA TTA<br>Thr Gly Asn Ser Pro Ser Glu Asn Asn Thr Asp Val Asn Asn Ala Leu<br>    180                    185                    190 | 576 |
| GAA TCT TAC AAA AAA TTT CTC CCA GAA GGA ACA GAT GTT GCA ACA GTT<br>Glu Ser Tyr Lys Lys Phe Leu Pro Glu Gly Thr Asp Val Ala Thr Val<br>          195                    200                 205 | 624 |
| GTA AGT GAA AGT GGA TCC GAC ACA TTA GAA CAA AGT CAA CCA AAG AAA<br>Val Ser Glu Ser Gly Ser Asp Thr Leu Glu Gln Ser Gln Pro Lys Lys<br>    210                    215                    220 | 672 |
| CCA GCA TCA ACT CAT GTA GGA GCA GAG TCT AAC ACA ATA ACA ACA TCA<br>Pro Ala Ser Thr His Val Gly Ala Glu Ser Asn Thr Ile Thr Thr Ser<br>225                  230                    235                240 | 720 |
| CAA AAT GTC GAT GAT GAA GTA GAT GAC GTA ATC ATA GTA CCT ATA TTT<br>Gln Asn Val Asp Asp Glu Val Asp Asp Val Ile Ile Val Pro Ile Phe<br>          245                    250                 255 | 768 |
| GGA GAA TCC GAA GAA GAT TAT GAT GAT TTA GGA CAA GTA GTA ACA GGA<br>Gly Glu Ser Glu Glu Asp Tyr Asp Asp Leu Gly Gln Val Val Thr Gly<br>    260                    265                    270 | 816 |
| GAA GCA GTA ACT CCT TCC GTA ATT GAT AAC ATA CTT TCT AAA ATT GAA<br>Glu Ala Val Thr Pro Ser Val Ile Asp Asn Ile Leu Ser Lys Ile Glu<br>          275                    280                 285 | 864 |
| AAT GAA TAT GAG GTT TTA TAT TTA AAA CCT TTA GCA GGT GTT TAT AGA<br>Asn Glu Tyr Glu Val Leu Tyr Leu Lys Pro Leu Ala Gly Val Tyr Arg<br>    290                    295                    300 | 912 |
| AGT TTA AAA AAA CAA TTA GAA AAT AAC GTT ATG ACA TTT AAT GTT AAT<br>Ser Leu Lys Lys Gln Leu Glu Asn Asn Val Met Thr Phe Asn Val Asn<br>305                  310                    315                320 | 960 |
| GTT AAG GAT ATT TTA AAT TCA CGA TTT AAT AAA CGT GAA AAT TTC AAA<br>Val Lys Asp Ile Leu Asn Ser Arg Phe Asn Lys Arg Glu Asn Phe Lys<br>          325                    330                 335 | 1008 |
| AAT GTT TTA GAA TCA GAT TTA ATT CCA TAT AAA GAT TTA ACA TCA AGT<br>Asn Val Leu Glu Ser Asp Leu Ile Pro Tyr Lys Asp Leu Thr Ser Ser<br>    340                    345                    350 | 1056 |

```
AAT TAT GTT GTC AAA GAT CCA TAT AAA TTT CTT AAT AAA GAA AAA AGA        1104
Asn Tyr Val Val Lys Asp Pro Tyr Lys Phe Leu Asn Lys Glu Lys Arg
        355                 360                 365

GAT AAA TTC TTA AGC AGT TAT AAT TAT ATT AAG GAT TCA ATA GAT ACG        1152
Asp Lys Phe Leu Ser Ser Tyr Asn Tyr Ile Lys Asp Ser Ile Asp Thr
370                 375                 380

GAT ATA AAT TTT GCA AAT GAT GTT CTT GGA TAT TAT AAA ATA TTA TCC        1200
Asp Ile Asn Phe Ala Asn Asp Val Leu Gly Tyr Tyr Lys Ile Leu Ser
385                 390                 395                 400

GAA AAA TAT AAA TCA GAT TTA GAT TCA ATT AAA AAA TAT ATC AAC GAC        1248
Glu Lys Tyr Lys Ser Asp Leu Asp Ser Ile Lys Lys Tyr Ile Asn Asp
            405                 410                 415

AAA CAA GGT GAA AAT GAG AAA TAC CTT CCC TTT TTA AAC AAT ATT GAG        1296
Lys Gln Gly Glu Asn Glu Lys Tyr Leu Pro Phe Leu Asn Asn Ile Glu
                420                 425                 430

ACC TTA TAT AAA ACA GTT AAT GAT AAA ATT GAT TTA TTT GTA ATT CAT        1344
Thr Leu Tyr Lys Thr Val Asn Asp Lys Ile Asp Leu Phe Val Ile His
                    435                 440                 445

TTA GAA GCA AAA GTT CTA AAT TAT ACA TAT GAG AAA TCA AAC GTA GAA        1392
Leu Glu Ala Lys Val Leu Asn Tyr Thr Tyr Glu Lys Ser Asn Val Glu
        450                 455                 460

GTT AAA ATA AAA GAA CTT AAT TAC TTA AAA ACA ATT CAA GAC AAA TTG        1440
Val Lys Ile Lys Glu Leu Asn Tyr Leu Lys Thr Ile Gln Asp Lys Leu
465                 470                 475                 480

GCA GAT TTT AAA AAA AAT AAC AAT TTC GTT GGA ATT GCT GAT TTA TCA        1488
Ala Asp Phe Lys Lys Asn Asn Asn Phe Val Gly Ile Ala Asp Leu Ser
                485                 490                 495

ACA GAT TAT AAC CAT AAT AAC TTA TTG ACA AAG TTC CTT AGT ACA GGT        1536
Thr Asp Tyr Asn His Asn Asn Leu Leu Thr Lys Phe Leu Ser Thr Gly
                    500                 505                 510

ATG GTT TTT GAA AAT CTT GCT AAA ACC GTT TTA TCT AAT TTA CTT GAT        1584
Met Val Phe Glu Asn Leu Ala Lys Thr Val Leu Ser Asn Leu Leu Asp
        515                 520                 525

GGA AAC TTG CAA GGT ATG TTA AAC ATT TCA CAA CAC CAA TGC GTA AAA        1632
Gly Asn Leu Gln Gly Met Leu Asn Ile Ser Gln His Gln Cys Val Lys
530                 535                 540

AAA CAA TGT CCA CAA AAT TCT GGA TGT TTC AGA CAT TTA GAT GAA AGA        1680
Lys Gln Cys Pro Gln Asn Ser Gly Cys Phe Arg His Leu Asp Glu Arg
545                 550                 555                 560

GAA GAA TGT AAA TGT TTA TTA AAT TAC AAA CAA GAA GGT GAT AAA TGT        1728
Glu Glu Cys Lys Cys Leu Leu Asn Tyr Lys Gln Glu Gly Asp Lys Cys
                565                 570                 575

GTT GAA AAT CCA AAT CCT ACT TGT AAC GAA AAT AAT GGT GGA TGT GAT        1776
Val Glu Asn Pro Asn Pro Thr Cys Asn Glu Asn Asn Gly Gly Cys Asp
                    580                 585                 590

GCA GAT GCC AAA TGT ACC GAA GAA GAT TCA GGT AGC AAC GGA AAG AAA        1824
Ala Asp Ala Lys Cys Thr Glu Glu Asp Ser Gly Ser Asn Gly Lys Lys
        595                 600                 605

ATC ACA TGT GAA TGT ACT AAA CCT GAT TCT TAT CCA CTT TTC GAT GGT        1872
Ile Thr Cys Glu Cys Thr Lys Pro Asp Ser Tyr Pro Leu Phe Asp Gly
610                 615                 620

ATT TTC TGC AGT TCC TCT AAC TAA                                        1896
Ile Phe Cys Ser Ser Ser Asn *
625                 630
```

(2) INFORMATION FOR SEQ ID NO: 18:

(i) SEQUENCE CHARACTERISTICS:
        (A) LENGTH: 631 amino acids
        (B) TYPE: amino acid (D) TOPOLOGY: linear (ii) MOLECULE TYPE: protein (xi) SEQUENCE DESCRIPTION: SEQ ID NO: 18:

```
Met Lys Ile Ile Phe Phe Leu Cys Ser Phe Leu Phe Ile Ile Asn
  1               5                  10                  15

Thr Gln Cys Val Thr His Glu Ser Tyr Gln Glu Leu Val Lys Lys Leu
             20                  25                  30

Glu Ala Leu Glu Asp Ala Val Leu Thr Gly Tyr Ser Leu Phe Gln Lys
         35                  40                  45

Glu Lys Met Val Leu Asn Glu Leu Asn Ser Leu Asn Asn Pro Lys His
     50                  55                  60

Val Leu Gln Asn Phe Ser Val Phe Phe Asn Lys Lys Glu Ala Glu
 65                  70                  75                  80

Ile Ala Glu Thr Glu Asn Thr Leu Glu Asn Thr Lys Ile Leu Leu Lys
             85                  90                  95

His Tyr Lys Gly Leu Val Lys Tyr Tyr Asn Gly Glu Ser Ser Pro Leu
            100                 105                 110

Lys Thr Leu Ser Glu Glu Ser Ile Gln Thr Glu Asp Asn Tyr Ala Ser
        115                 120                 125

Leu Glu Asn Phe Lys Val Leu Ser Lys Leu Glu Gly Lys Leu Lys Asp
    130                 135                 140

Asn Leu Asn Leu Glu Lys Lys Leu Ser Tyr Leu Ser Ser Gly Leu
145                 150                 155                 160

His His Leu Ile Ala Glu Leu Lys Glu Val Ile Lys Asn Lys Asn Tyr
                165                 170                 175

Thr Gly Asn Ser Pro Ser Glu Asn Asn Thr Asp Val Asn Asn Ala Leu
            180                 185                 190

Glu Ser Tyr Lys Lys Phe Leu Pro Glu Gly Thr Asp Val Ala Thr Val
        195                 200                 205

Val Ser Glu Ser Gly Ser Asp Thr Leu Glu Gln Ser Gln Pro Lys Lys
    210                 215                 220

Pro Ala Ser Thr His Val Gly Ala Glu Ser Asn Thr Ile Thr Thr Ser
225                 230                 235                 240

Gln Asn Val Asp Asp Glu Val Asp Asp Val Ile Ile Val Pro Ile Phe
                245                 250                 255

Gly Glu Ser Glu Glu Asp Tyr Asp Asp Leu Gly Gln Val Val Thr Gly
            260                 265                 270

Glu Ala Val Thr Pro Ser Val Ile Asp Asn Ile Leu Ser Lys Ile Glu
        275                 280                 285

Asn Glu Tyr Glu Val Leu Tyr Leu Lys Pro Leu Ala Gly Val Tyr Arg
    290                 295                 300

Ser Leu Lys Lys Gln Leu Glu Asn Asn Val Met Thr Phe Asn Val Asn
305                 310                 315                 320

Val Lys Asp Ile Leu Asn Ser Arg Phe Asn Lys Arg Glu Asn Phe Lys
                325                 330                 335

Asn Val Leu Glu Ser Asp Leu Ile Pro Tyr Lys Asp Leu Thr Ser Ser
            340                 345                 350

Asn Tyr Val Val Lys Asp Pro Tyr Lys Phe Leu Asn Lys Glu Lys Arg
        355                 360                 365

Asp Lys Phe Leu Ser Ser Tyr Asn Tyr Ile Lys Asp Ser Ile Asp Thr
    370                 375                 380

Asp Ile Asn Phe Ala Asn Asp Val Leu Gly Tyr Tyr Lys Ile Leu Ser
```

```
385                 390                 395                 400

Glu Lys Tyr Lys Ser Asp Leu Asp Ser Ile Lys Lys Tyr Ile Asn Asp
                405                 410                 415

Lys Gln Gly Glu Asn Glu Lys Tyr Leu Pro Phe Leu Asn Asn Ile Glu
                420                 425                 430

Thr Leu Tyr Lys Thr Val Asn Asp Lys Ile Asp Leu Phe Val Ile His
                435                 440                 445

Leu Glu Ala Lys Val Leu Asn Tyr Thr Tyr Glu Lys Ser Asn Val Glu
                450                 455                 460

Val Lys Ile Lys Glu Leu Asn Tyr Leu Lys Thr Ile Gln Asp Lys Leu
465                 470                 475                 480

Ala Asp Phe Lys Lys Asn Asn Phe Val Gly Ile Ala Asp Leu Ser
                485                 490                 495

Thr Asp Tyr Asn His Asn Asn Leu Leu Thr Lys Phe Leu Ser Thr Gly
                500                 505                 510

Met Val Phe Glu Asn Leu Ala Lys Thr Val Leu Ser Asn Leu Leu Asp
                515                 520                 525

Gly Asn Leu Gln Gly Met Leu Asn Ile Ser Gln His Gln Cys Val Lys
                530                 535                 540

Lys Gln Cys Pro Gln Asn Ser Gly Cys Phe Arg His Leu Asp Glu Arg
545                 550                 555                 560

Glu Glu Cys Lys Cys Leu Leu Asn Tyr Lys Gln Glu Gly Asp Lys Cys
                565                 570                 575

Val Glu Asn Pro Asn Pro Thr Cys Asn Glu Asn Asn Gly Gly Cys Asp
                580                 585                 590

Ala Asp Ala Lys Cys Thr Glu Glu Asp Ser Gly Ser Asn Gly Lys Lys
                595                 600                 605

Ile Thr Cys Glu Cys Thr Lys Pro Asp Ser Tyr Pro Leu Phe Asp Gly
                610                 615                 620

Ile Phe Cys Ser Ser Ser Asn
625                 630
```

(2) INFORMATION FOR SEQ ID NO: 19:

(i) SEQUENCE CHARACTERISTICS:
        (A) LENGTH: 1896 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Plasmodium falciparum (vii) IMMEDIATE SOURCE:
        (B) CLONE: MSA1C-(nSi,A)

(ix) FEATURE:
        (A) NAME/KEY: CDS
        (B) LOCATION: 1..1896

(ix) FEATURE:
        (A) NAME/KEY: misc_feature
        (B) LOCATION: 1840..1896
        (D) OTHER INFORMATION: /product= "anchor peptide"
           /label= anchor_peptide (xi) SEQUENCE DESCRIPTION: SEQ ID NO: 19:

-continued

| | |
|---|---|
| ATG GTA ACA CAT GAA AGT TAT CAA GAA CTT GTC AAA AAA CTA GAA GCT<br>Met Val Thr His Glu Ser Tyr Gln Glu Leu Val Lys Lys Leu Glu Ala<br>1                    5                      10                   15 | 48 |
| TTA GAA GAT GCA GTA TTG ACA GGT TAT AGT TTA TTT CAA AAG GAA AAA<br>Leu Glu Asp Ala Val Leu Thr Gly Tyr Ser Leu Phe Gln Lys Glu Lys<br>                   20                      25                   30 | 96 |
| ATG GTA TTA AAT GAA TTG AAT TCA CTT AAT AAC CCA AAG CAT GTA TTA<br>Met Val Leu Asn Glu Leu Asn Ser Leu Asn Asn Pro Lys His Val Leu<br>        35                      40                   45 | 144 |
| CAA AAC TTT TCT GTT TTC TTT AAC AAA AAA AAA GAA GCT GAA ATA GCA<br>Gln Asn Phe Ser Val Phe Phe Asn Lys Lys Lys Glu Ala Glu Ile Ala<br>   50                      55                   60 | 192 |
| GAA ACT GAA AAC ACA TTA GAA AAC ACA AAA ATA TTA TTG AAA CAT TAT<br>Glu Thr Glu Asn Thr Leu Glu Asn Thr Lys Ile Leu Leu Lys His Tyr<br>65                    70                      75                   80 | 240 |
| AAA GGA CTT GTT AAA TAT TAT AAT GGT GAA TCA TCT CCA TTA AAA ACT<br>Lys Gly Leu Val Lys Tyr Tyr Asn Gly Glu Ser Ser Pro Leu Lys Thr<br>                   85                      90                   95 | 288 |
| TTA AGT GAA GAA TCA ATT CAA ACA GAA GAT AAT TAT GCC AGT TTA GAA<br>Leu Ser Glu Glu Ser Ile Gln Thr Glu Asp Asn Tyr Ala Ser Leu Glu<br>        100                     105                 110 | 336 |
| AAC TTT AAA GTA TTA AGT AAA TTA GAA GGA AAA TTA AAG GAT AAT TTA<br>Asn Phe Lys Val Leu Ser Lys Leu Glu Gly Lys Leu Lys Asp Asn Leu<br>   115                     120                 125 | 384 |
| AAT TTA GAA AAG AAA AAA TTA TCA TAC TTA TCA AGT GGA TTA CAT CAT<br>Asn Leu Glu Lys Lys Lys Leu Ser Tyr Leu Ser Ser Gly Leu His His<br>        130                     135                 140 | 432 |
| TTA ATT GCT GAA TTA AAA GAA GTA ATA AAA AAT AAA AAT TAT ACA GGT<br>Leu Ile Ala Glu Leu Lys Glu Val Ile Lys Asn Lys Asn Tyr Thr Gly<br>145                    150                     155               160 | 480 |
| AAT TCT CCA AGT GAA AAT AAT ACG GAT GTT AAC AAT GCA TTA GAA TCT<br>Asn Ser Pro Ser Glu Asn Asn Thr Asp Val Asn Asn Ala Leu Glu Ser<br>                   165                     170                 175 | 528 |
| TAC AAA AAA TTT CTC CCA GAA GGA ACA GAT GTT GCA ACA GTT GTA AGT<br>Tyr Lys Lys Phe Leu Pro Glu Gly Thr Asp Val Ala Thr Val Val Ser<br>        180                     185                 190 | 576 |
| GAA AGT GGA TCC GAC ACA TTA GAA CAA AGT CAA CCA AAG AAA CCA GCA<br>Glu Ser Gly Ser Asp Thr Leu Glu Gln Ser Gln Pro Lys Lys Pro Ala<br>   195                     200                 205 | 624 |
| TCA ACT CAT GTA GGA GCA GAG TCT AAC ACA ATA ACA ACA TCA CAA AAT<br>Ser Thr His Val Gly Ala Glu Ser Asn Thr Ile Thr Thr Ser Gln Asn<br>210                    215                     220 | 672 |
| GTC GAT GAT GAA GTA GAT GAC GTA ATC ATA GTA CCT ATA TTT GGA GAA<br>Val Asp Asp Glu Val Asp Asp Val Ile Ile Val Pro Ile Phe Gly Glu<br>225                    230                     235               240 | 720 |
| TCC GAA GAA GAT TAT GAT GAT TTA GGA CAA GTA GTA ACA GGA GAA GCA<br>Ser Glu Glu Asp Tyr Asp Asp Leu Gly Gln Val Val Thr Gly Glu Ala<br>                   245                     250                 255 | 768 |
| GTA ACT CCT TCC GTA ATT GAT AAC ATA CTT TCT AAA ATT GAA AAT GAA<br>Val Thr Pro Ser Val Ile Asp Asn Ile Leu Ser Lys Ile Glu Asn Glu<br>        260                     265                 270 | 816 |
| TAT GAG GTT TTA TAT TTA AAA CCT TTA GCA GGT GTT TAT AGA AGT TTA<br>Tyr Glu Val Leu Tyr Leu Lys Pro Leu Ala Gly Val Tyr Arg Ser Leu<br>   275                     280                 285 | 864 |
| AAA AAA CAA TTA GAA AAT AAC GTT ATG ACA TTT AAT GTT AAT GTT AAG<br>Lys Lys Gln Leu Glu Asn Asn Val Met Thr Phe Asn Val Asn Val Lys<br>        290                     295                 300 | 912 |
| GAT ATT TTA AAT TCA CGA TTT AAT AAA CGT GAA AAT TTC AAA AAT GTT<br>Asp Ile Leu Asn Ser Arg Phe Asn Lys Arg Glu Asn Phe Lys Asn Val | 960 |

-continued

| | | | | | | | | | | | | | | | | |
|---|---|---|---|---|---|---|---|---|---|---|---|---|---|---|---|---|
| | | | 305 | | | | 310 | | | | 315 | | | | 320 | |
| TTA | GAA | TCA | GAT | TTA | ATT | CCA | TAT | AAA | GAT | TTA | ACA | TCA | AGT | AAT | TAT | 1008 |
| Leu | Glu | Ser | Asp | Leu | Ile | Pro | Tyr | Lys | Asp | Leu | Thr | Ser | Ser | Asn | Tyr | |
| | | | | 325 | | | | | 330 | | | | | 335 | | |
| GTT | GTC | AAA | GAT | CCA | TAT | AAA | TTT | CTT | AAT | AAA | GAA | AAA | AGA | GAT | AAA | 1056 |
| Val | Val | Lys | Asp | Pro | Tyr | Lys | Phe | Leu | Asn | Lys | Glu | Lys | Arg | Asp | Lys | |
| | | | 340 | | | | | 345 | | | | | 350 | | | |
| TTC | TTA | AGC | AGT | TAT | AAT | TAT | ATT | AAG | GAT | TCA | ATA | GAT | ACG | GAT | ATA | 1104 |
| Phe | Leu | Ser | Ser | Tyr | Asn | Tyr | Ile | Lys | Asp | Ser | Ile | Asp | Thr | Asp | Ile | |
| | | | | 355 | | | | | 360 | | | | | 365 | | |
| AAT | TTT | GCA | AAT | GAT | GTT | CTT | GGA | TAT | TAT | AAA | ATA | TTA | TCC | GAA | AAA | 1152 |
| Asn | Phe | Ala | Asn | Asp | Val | Leu | Gly | Tyr | Tyr | Lys | Ile | Leu | Ser | Glu | Lys | |
| | | 370 | | | | | 375 | | | | | 380 | | | | |
| TAT | AAA | TCA | GAT | TTA | GAT | TCA | ATT | AAA | AAA | TAT | ATC | AAC | GAC | AAA | CAA | 1200 |
| Tyr | Lys | Ser | Asp | Leu | Asp | Ser | Ile | Lys | Lys | Tyr | Ile | Asn | Asp | Lys | Gln | |
| 385 | | | | | 390 | | | | | 395 | | | | | 400 | |
| GGT | GAA | AAT | GAG | AAA | TAC | CTT | CCC | TTT | TTA | AAC | AAT | ATT | GAG | ACC | TTA | 1248 |
| Gly | Glu | Asn | Glu | Lys | Tyr | Leu | Pro | Phe | Leu | Asn | Asn | Ile | Glu | Thr | Leu | |
| | | | | 405 | | | | | 410 | | | | | 415 | | |
| TAT | AAA | ACA | GTT | AAT | GAT | AAA | ATT | GAT | TTA | TTT | GTA | ATT | CAT | TTA | GAA | 1296 |
| Tyr | Lys | Thr | Val | Asn | Asp | Lys | Ile | Asp | Leu | Phe | Val | Ile | His | Leu | Glu | |
| | | | 420 | | | | | 425 | | | | | 430 | | | |
| GCA | AAA | GTT | CTA | AAT | TAT | ACA | TAT | GAG | AAA | TCA | AAC | GTA | GAA | GTT | AAA | 1344 |
| Ala | Lys | Val | Leu | Asn | Tyr | Thr | Tyr | Glu | Lys | Ser | Asn | Val | Glu | Val | Lys | |
| | | | | 435 | | | | | 440 | | | | | 445 | | |
| ATA | AAA | GAA | CTT | AAT | TAC | TTA | AAA | ACA | ATT | CAA | GAC | AAA | TTG | GCA | GAT | 1392 |
| Ile | Lys | Glu | Leu | Asn | Tyr | Leu | Lys | Thr | Ile | Gln | Asp | Lys | Leu | Ala | Asp | |
| | | 450 | | | | | 455 | | | | | 460 | | | | |
| TTT | AAA | AAA | AAT | AAC | AAT | TTC | GTT | GGA | ATT | GCT | GAT | TTA | TCA | ACA | GAT | 1440 |
| Phe | Lys | Lys | Asn | Asn | Asn | Phe | Val | Gly | Ile | Ala | Asp | Leu | Ser | Thr | Asp | |
| 465 | | | | | 470 | | | | | 475 | | | | | 480 | |
| TAT | AAC | CAT | AAT | AAC | TTA | TTG | ACA | AAG | TTC | CTT | AGT | ACA | GGT | ATG | GTT | 1488 |
| Tyr | Asn | His | Asn | Asn | Leu | Leu | Thr | Lys | Phe | Leu | Ser | Thr | Gly | Met | Val | |
| | | | | 485 | | | | | 490 | | | | | 495 | | |
| TTT | GAA | AAT | CTT | GCT | AAA | ACC | GTT | TTA | TCT | AAT | TTA | CTT | GAT | GGA | AAC | 1536 |
| Phe | Glu | Asn | Leu | Ala | Lys | Thr | Val | Leu | Ser | Asn | Leu | Leu | Asp | Gly | Asn | |
| | | | 500 | | | | | 505 | | | | | 510 | | | |
| TTG | CAA | GGT | ATG | TTA | AAC | ATT | TCA | CAA | CAC | CAA | TGC | GTA | AAA | AAA | CAA | 1584 |
| Leu | Gln | Gly | Met | Leu | Asn | Ile | Ser | Gln | His | Gln | Cys | Val | Lys | Lys | Gln | |
| | | | | 515 | | | | | 520 | | | | | 525 | | |
| TGT | CCA | CAA | AAT | TCT | GGA | TGT | TTC | AGA | CAT | TTA | GAT | GAA | AGA | GAA | GAA | 1632 |
| Cys | Pro | Gln | Asn | Ser | Gly | Cys | Phe | Arg | His | Leu | Asp | Glu | Arg | Glu | Glu | |
| | | 530 | | | | | 535 | | | | | 540 | | | | |
| TGT | AAA | TGT | TTA | TTA | AAT | TAC | AAA | CAA | GAA | GGT | GAT | AAA | TGT | GTT | GAA | 1680 |
| Cys | Lys | Cys | Leu | Leu | Asn | Tyr | Lys | Gln | Glu | Gly | Asp | Lys | Cys | Val | Glu | |
| 545 | | | | | 550 | | | | | 555 | | | | | 560 | |
| AAT | CCA | AAT | CCT | ACT | TGT | AAC | GAA | AAT | AAT | GGT | GGA | TGT | GAT | GCA | GAT | 1728 |
| Asn | Pro | Asn | Pro | Thr | Cys | Asn | Glu | Asn | Asn | Gly | Gly | Cys | Asp | Ala | Asp | |
| | | | | 565 | | | | | 570 | | | | | 575 | | |
| GCC | AAA | TGT | ACC | GAA | GAA | GAT | TCA | GGT | AGC | AAC | GGA | AAG | AAA | ATC | ACA | 1776 |
| Ala | Lys | Cys | Thr | Glu | Glu | Asp | Ser | Gly | Ser | Asn | Gly | Lys | Lys | Ile | Thr | |
| | | | 580 | | | | | 585 | | | | | 590 | | | |
| TGT | GAA | TGT | ACT | AAA | CCT | GAT | TCT | TAT | CCA | CTT | TTC | GAT | GGT | ATT | TTC | 1824 |
| Cys | Glu | Cys | Thr | Lys | Pro | Asp | Ser | Tyr | Pro | Leu | Phe | Asp | Gly | Ile | Phe | |
| | | 595 | | | | | 600 | | | | | 605 | | | | |
| TGC | AGT | TCC | TCT | AAC | TTC | TTA | GGA | ATA | TCA | TTC | TTA | TTA | ATA | CTC | ATG | 1872 |
| Cys | Ser | Ser | Ser | Asn | Phe | Leu | Gly | Ile | Ser | Phe | Leu | Leu | Ile | Leu | Met | |
| | | 610 | | | | | 615 | | | | | 620 | | | | |
| TTA | ATA | TTA | TAC | AGT | TTC | ATT | TAA | | | | | | | | | 1896 |

```
Leu Ile Leu Tyr Ser Phe Ile  *
625                 630
```

(2) INFORMATION FOR SEQ ID NO: 20:

(i) SEQUENCE CHARACTERISTICS:
        (A) LENGTH: 631 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Val Thr His Glu Ser Tyr Gln Glu Leu Val Lys Lys Leu Glu Ala
  1               5                  10                  15

Leu Glu Asp Ala Val Leu Thr Gly Tyr Ser Leu Phe Gln Lys Glu Lys
             20                  25                  30

Met Val Leu Asn Glu Leu Asn Ser Leu Asn Asn Pro Lys His Val Leu
         35                  40                  45

Gln Asn Phe Ser Val Phe Phe Asn Lys Lys Glu Ala Glu Ile Ala
     50                  55                  60

Glu Thr Glu Asn Thr Leu Glu Asn Thr Lys Ile Leu Leu Lys His Tyr
 65                  70                  75                  80

Lys Gly Leu Val Lys Tyr Tyr Asn Gly Glu Ser Ser Pro Leu Lys Thr
                 85                  90                  95

Leu Ser Glu Glu Ser Ile Gln Thr Glu Asp Asn Tyr Ala Ser Leu Glu
                100                 105                 110

Asn Phe Lys Val Leu Ser Lys Leu Glu Gly Lys Leu Lys Asp Asn Leu
            115                 120                 125

Asn Leu Glu Lys Lys Lys Leu Ser Tyr Leu Ser Ser Gly Leu His His
        130                 135                 140

Leu Ile Ala Glu Leu Lys Glu Val Ile Lys Asn Lys Asn Tyr Thr Gly
145                 150                 155                 160

Asn Ser Pro Ser Glu Asn Asn Thr Asp Val Asn Asn Ala Leu Glu Ser
                165                 170                 175

Tyr Lys Lys Phe Leu Pro Glu Gly Thr Asp Val Ala Thr Val Val Ser
            180                 185                 190

Glu Ser Gly Ser Asp Thr Leu Glu Gln Ser Gln Pro Lys Lys Pro Ala
        195                 200                 205

Ser Thr His Val Gly Ala Glu Ser Asn Thr Ile Thr Thr Ser Gln Asn
    210                 215                 220

Val Asp Asp Glu Val Asp Val Ile Ile Val Pro Ile Phe Gly Glu
225                 230                 235                 240

Ser Glu Glu Asp Tyr Asp Asp Leu Gly Gln Val Val Thr Gly Glu Ala
                245                 250                 255

Val Thr Pro Ser Val Ile Asp Asn Ile Leu Ser Lys Ile Glu Asn Glu
            260                 265                 270

Tyr Glu Val Leu Tyr Leu Lys Pro Leu Ala Gly Val Tyr Arg Ser Leu
        275                 280                 285

Lys Lys Gln Leu Glu Asn Asn Val Met Thr Phe Asn Val Asn Val Lys
    290                 295                 300

Asp Ile Leu Asn Ser Arg Phe Asn Lys Arg Glu Asn Phe Lys Asn Val
305                 310                 315                 320

Leu Glu Ser Asp Leu Ile Pro Tyr Lys Asp Leu Thr Ser Ser Asn Tyr
                325                 330                 335

Val Val Lys Asp Pro Tyr Lys Phe Leu Asn Lys Glu Lys Arg Asp Lys
```

```
                340                 345                 350
Phe Leu Ser Ser Tyr Asn Tyr Ile Lys Asp Ser Ile Asp Thr Asp Ile
            355                 360                 365

Asn Phe Ala Asn Asp Val Leu Gly Tyr Tyr Lys Ile Leu Ser Glu Lys
    370                 375                 380

Tyr Lys Ser Asp Leu Asp Ser Ile Lys Lys Tyr Ile Asn Asp Lys Gln
385                 390                 395                 400

Gly Glu Asn Glu Lys Tyr Leu Pro Phe Leu Asn Asn Ile Glu Thr Leu
                405                 410                 415

Tyr Lys Thr Val Asn Asp Lys Ile Asp Leu Phe Val Ile His Leu Glu
                420                 425                 430

Ala Lys Val Leu Asn Tyr Thr Tyr Glu Lys Ser Asn Val Glu Val Lys
            435                 440                 445

Ile Lys Glu Leu Asn Tyr Leu Lys Thr Ile Gln Asp Lys Leu Ala Asp
    450                 455                 460

Phe Lys Lys Asn Asn Asn Phe Val Gly Ile Ala Asp Leu Ser Thr Asp
465                 470                 475                 480

Tyr Asn His Asn Asn Leu Leu Thr Lys Phe Leu Ser Thr Gly Met Val
                485                 490                 495

Phe Glu Asn Leu Ala Lys Thr Val Leu Ser Asn Leu Leu Asp Gly Asn
                500                 505                 510

Leu Gln Gly Met Leu Asn Ile Ser Gln His Gln Cys Val Lys Lys Gln
            515                 520                 525

Cys Pro Gln Asn Ser Gly Cys Phe Arg His Leu Asp Glu Arg Glu Glu
    530                 535                 540

Cys Lys Cys Leu Leu Asn Tyr Lys Gln Glu Gly Asp Lys Cys Val Glu
545                 550                 555                 560

Asn Pro Asn Pro Thr Cys Asn Glu Asn Asn Gly Gly Cys Asp Ala Asp
                565                 570                 575

Ala Lys Cys Thr Glu Glu Asp Ser Gly Ser Asn Gly Lys Lys Ile Thr
            580                 585                 590

Cys Glu Cys Thr Lys Pro Asp Ser Tyr Pro Leu Phe Asp Gly Ile Phe
    595                 600                 605

Cys Ser Ser Ser Asn Phe Leu Gly Ile Ser Phe Leu Leu Ile Leu Met
610                 615                 620

Leu Ile Leu Tyr Ser Phe Ile
625                 630

(2) INFORMATION FOR SEQ ID NO: 21:

(i) SEQUENCE CHARACTERISTICS:
        (A) LENGTH: 1842 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Plasmodium falciparum (vii) IMMEDIATE SOURCE:
        (B) CLONE: MSA1C-(nSi,nA)

(ix) FEATURE:
        (A) NAME/KEY: CDS
```

(B) LOCATION: 1..1842

(xi) SEQUENCE DESCRIPTION: SEQ ID NO: 21:

```
ATG GTA ACA CAT GAA AGT TAT CAA GAA CTT GTC AAA AAA CTA GAA GCT         48
Met Val Thr His Glu Ser Tyr Gln Glu Leu Val Lys Lys Leu Glu Ala
 1               5                  10                  15

TTA GAA GAT GCA GTA TTG ACA GGT TAT AGT TTA TTT CAA AAG GAA AAA         96
Leu Glu Asp Ala Val Leu Thr Gly Tyr Ser Leu Phe Gln Lys Glu Lys
             20                  25                  30

ATG GTA TTA AAT GAA TTG AAT TCA CTT AAT AAC CCA AAG CAT GTA TTA        144
Met Val Leu Asn Glu Leu Asn Ser Leu Asn Asn Pro Lys His Val Leu
         35                  40                  45

CAA AAC TTT TCT GTT TTC TTT AAC AAA AAA AAA GAA GCT GAA ATA GCA        192
Gln Asn Phe Ser Val Phe Phe Asn Lys Lys Lys Glu Ala Glu Ile Ala
     50                  55                  60

GAA ACT GAA AAC ACA TTA GAA AAC ACA AAA ATA TTA TTG AAA CAT TAT        240
Glu Thr Glu Asn Thr Leu Glu Asn Thr Lys Ile Leu Leu Lys His Tyr
 65                  70                  75                  80

AAA GGA CTT GTT AAA TAT TAT AAT GGT GAA TCA TCT CCA TTA AAA ACT        288
Lys Gly Leu Val Lys Tyr Tyr Asn Gly Glu Ser Ser Pro Leu Lys Thr
                 85                  90                  95

TTA AGT GAA GAA TCA ATT CAA ACA GAA GAT AAT TAT GCC AGT TTA GAA        336
Leu Ser Glu Glu Ser Ile Gln Thr Glu Asp Asn Tyr Ala Ser Leu Glu
             100                 105                 110

AAC TTT AAA GTA TTA AGT AAA TTA GAA GGA AAA TTA AAG GAT AAT TTA        384
Asn Phe Lys Val Leu Ser Lys Leu Glu Gly Lys Leu Lys Asp Asn Leu
         115                 120                 125

AAT TTA GAA AAG AAA AAA TTA TCA TAC TTA TCA AGT GGA TTA CAT CAT        432
Asn Leu Glu Lys Lys Lys Leu Ser Tyr Leu Ser Ser Gly Leu His His
     130                 135                 140

TTA ATT GCT GAA TTA AAA GAA GTA ATA AAA AAT AAA AAT TAT ACA GGT        480
Leu Ile Ala Glu Leu Lys Glu Val Ile Lys Asn Lys Asn Tyr Thr Gly
145                 150                 155                 160

AAT TCT CCA AGT GAA AAT AAT ACG GAT GTT AAC AAT GCA TTA GAA TCT        528
Asn Ser Pro Ser Glu Asn Asn Thr Asp Val Asn Asn Ala Leu Glu Ser
                 165                 170                 175

TAC AAA AAA TTT CTC CCA GAA GGA ACA GAT GTT GCA ACA GTT GTA AGT        576
Tyr Lys Lys Phe Leu Pro Glu Gly Thr Asp Val Ala Thr Val Val Ser
             180                 185                 190

GAA AGT GGA TCC GAC ACA TTA GAA CAA AGT CAA CCA AAG AAA CCA GCA        624
Glu Ser Gly Ser Asp Thr Leu Glu Gln Ser Gln Pro Lys Lys Pro Ala
         195                 200                 205

TCA ACT CAT GTA GGA GCA GAG TCT AAC ACA ATA ACA ACA TCA CAA AAT        672
Ser Thr His Val Gly Ala Glu Ser Asn Thr Ile Thr Thr Ser Gln Asn
     210                 215                 220

GTC GAT GAT GAA GTA GAT GAC GTA ATC ATA GTA CCT ATA TTT GGA GAA        720
Val Asp Asp Glu Val Asp Asp Val Ile Ile Val Pro Ile Phe Gly Glu
225                 230                 235                 240

TCC GAA GAA GAT TAT GAT GAT TTA GGA CAA GTA GTA ACA GGA GAA GCA        768
Ser Glu Glu Asp Tyr Asp Asp Leu Gly Gln Val Val Thr Gly Glu Ala
                 245                 250                 255

GTA ACT CCT TCC GTA ATT GAT AAC ATA CTT TCT AAA ATT GAA AAT GAA        816
Val Thr Pro Ser Val Ile Asp Asn Ile Leu Ser Lys Ile Glu Asn Glu
             260                 265                 270

TAT GAG GTT TTA TAT TTA AAA CCT TTA GCA GGT GTT TAT AGA AGT TTA        864
Tyr Glu Val Leu Tyr Leu Lys Pro Leu Ala Gly Val Tyr Arg Ser Leu
         275                 280                 285

AAA AAA CAA TTA GAA AAT AAC GTT ATG ACA TTT AAT GTT AAT GTT AAG        912
Lys Lys Gln Leu Glu Asn Asn Val Met Thr Phe Asn Val Asn Val Lys
     290                 295                 300
```

```
GAT ATT TTA AAT TCA CGA TTT AAT AAA CGT GAA AAT TTC AAA AAT GTT      960
Asp Ile Leu Asn Ser Arg Phe Asn Lys Arg Glu Asn Phe Lys Asn Val
305             310                 315                 320

TTA GAA TCA GAT TTA ATT CCA TAT AAA GAT TTA ACA TCA AGT AAT TAT     1008
Leu Glu Ser Asp Leu Ile Pro Tyr Lys Asp Leu Thr Ser Ser Asn Tyr
                325                 330                 335

GTT GTC AAA GAT CCA TAT AAA TTT CTT AAT AAA GAA AAA AGA GAT AAA     1056
Val Val Lys Asp Pro Tyr Lys Phe Leu Asn Lys Glu Lys Arg Asp Lys
            340                 345                 350

TTC TTA AGC AGT TAT AAT TAT ATT AAG GAT TCA ATA GAT ACG GAT ATA     1104
Phe Leu Ser Ser Tyr Asn Tyr Ile Lys Asp Ser Ile Asp Thr Asp Ile
            355                 360                 365

AAT TTT GCA AAT GAT GTT CTT GGA TAT TAT AAA ATA TTA TCC GAA AAA     1152
Asn Phe Ala Asn Asp Val Leu Gly Tyr Tyr Lys Ile Leu Ser Glu Lys
370                 375                 380

TAT AAA TCA GAT TTA GAT TCA ATT AAA AAA TAT ATC AAC GAC AAA CAA     1200
Tyr Lys Ser Asp Leu Asp Ser Ile Lys Lys Tyr Ile Asn Asp Lys Gln
385                 390                 395                 400

GGT GAA AAT GAG AAA TAC CTT CCC TTT TTA AAC AAT ATT GAG ACC TTA     1248
Gly Glu Asn Glu Lys Tyr Leu Pro Phe Leu Asn Asn Ile Glu Thr Leu
                405                 410                 415

TAT AAA ACA GTT AAT GAT AAA ATT GAT TTA TTT GTA ATT CAT TTA GAA     1296
Tyr Lys Thr Val Asn Asp Lys Ile Asp Leu Phe Val Ile His Leu Glu
            420                 425                 430

GCA AAA GTT CTA AAT TAT ACA TAT GAG AAA TCA AAC GTA GAA GTT AAA     1344
Ala Lys Val Leu Asn Tyr Thr Tyr Glu Lys Ser Asn Val Glu Val Lys
            435                 440                 445

ATA AAA GAA CTT AAT TAC TTA AAA ACA ATT CAA GAC AAA TTG GCA GAT     1392
Ile Lys Glu Leu Asn Tyr Leu Lys Thr Ile Gln Asp Lys Leu Ala Asp
450                 455                 460

TTT AAA AAA AAT AAC AAT TTC GTT GGA ATT GCT GAT TTA TCA ACA GAT     1440
Phe Lys Lys Asn Asn Asn Phe Val Gly Ile Ala Asp Leu Ser Thr Asp
465                 470                 475                 480

TAT AAC CAT AAT AAC TTA TTG ACA AAG TTC CTT AGT ACA GGT ATG GTT     1488
Tyr Asn His Asn Asn Leu Leu Thr Lys Phe Leu Ser Thr Gly Met Val
                485                 490                 495

TTT GAA AAT CTT GCT AAA ACC GTT TTA TCT AAT TTA CTT GAT GGA AAC     1536
Phe Glu Asn Leu Ala Lys Thr Val Leu Ser Asn Leu Leu Asp Gly Asn
                500                 505                 510

TTG CAA GGT ATG TTA AAC ATT TCA CAA CAC CAA TGC GTA AAA AAA CAA     1584
Leu Gln Gly Met Leu Asn Ile Ser Gln His Gln Cys Val Lys Lys Gln
            515                 520                 525

TGT CCA CAA AAT TCT GGA TGT TTC AGA CAT TTA GAT GAA AGA GAA GAA     1632
Cys Pro Gln Asn Ser Gly Cys Phe Arg His Leu Asp Glu Arg Glu Glu
530                 535                 540

TGT AAA TGT TTA TTA AAT TAC AAA CAA GAA GGT GAT AAA TGT GTT GAA     1680
Cys Lys Cys Leu Leu Asn Tyr Lys Gln Glu Gly Asp Lys Cys Val Glu
545                 550                 555                 560

AAT CCA AAT CCT ACT TGT AAC GAA AAT AAT GGT GGA TGT GAT GCA GAT     1728
Asn Pro Asn Pro Thr Cys Asn Glu Asn Asn Gly Gly Cys Asp Ala Asp
                565                 570                 575

GCC AAA TGT ACC GAA GAA GAT TCA GGT AGC AAC GGA AAG AAA ATC ACA     1776
Ala Lys Cys Thr Glu Glu Asp Ser Gly Ser Asn Gly Lys Lys Ile Thr
                580                 585                 590

TGT GAA TGT ACT AAA CCT GAT TCT TAT CCA CTT TTC GAT GGT ATT TTC     1824
Cys Glu Cys Thr Lys Pro Asp Ser Tyr Pro Leu Phe Asp Gly Ile Phe
            595                 600                 605

TGC AGT TCC TCT AAC TAA                                              1842
Cys Ser Ser Ser Asn *
```

-continued

```
        610

(2) INFORMATION FOR SEQ ID NO: 22:

(i) SEQUENCE CHARACTERISTICS:
        (A) LENGTH: 613 amino acids
        (B) TYPE: amino acid
        (D) TOPOLOGY: linear (ii) MOLECULE TYPE: protein (xi) SEQUENCE DESCRIPTION: SEQ ID NO: 22:

Met Val Thr His Glu Ser Tyr Gln Glu Leu Val Lys Lys Leu Glu Ala
1               5                   10                  15

Leu Glu Asp Ala Val Leu Thr Gly Tyr Ser Leu Phe Gln Lys Glu Lys
                20                  25                  30

Met Val Leu Asn Glu Leu Asn Ser Leu Asn Asn Pro Lys His Val Leu
            35                  40                  45

Gln Asn Phe Ser Val Phe Phe Asn Lys Lys Lys Glu Ala Glu Ile Ala
    50                  55                  60

Glu Thr Glu Asn Thr Leu Glu Asn Thr Lys Ile Leu Leu Lys His Tyr
65                  70                  75                  80

Lys Gly Leu Val Lys Tyr Tyr Asn Gly Glu Ser Ser Pro Leu Lys Thr
                85                  90                  95

Leu Ser Glu Glu Ser Ile Gln Thr Glu Asp Asn Tyr Ala Ser Leu Glu
                100                 105                 110

Asn Phe Lys Val Leu Ser Lys Leu Glu Gly Lys Leu Lys Asp Asn Leu
            115                 120                 125

Asn Leu Glu Lys Lys Lys Leu Ser Tyr Leu Ser Ser Gly Leu His His
130                 135                 140

Leu Ile Ala Glu Leu Lys Glu Val Ile Lys Asn Lys Asn Tyr Thr Gly
145                 150                 155                 160

Asn Ser Pro Ser Glu Asn Asn Thr Asp Val Asn Asn Ala Leu Glu Ser
                165                 170                 175

Tyr Lys Lys Phe Leu Pro Glu Gly Thr Asp Val Ala Thr Val Val Ser
                180                 185                 190

Glu Ser Gly Ser Asp Thr Leu Glu Gln Ser Gln Pro Lys Lys Pro Ala
            195                 200                 205

Ser Thr His Val Gly Ala Glu Ser Asn Thr Ile Thr Thr Ser Gln Asn
210                 215                 220

Val Asp Asp Glu Val Asp Asp Val Ile Ile Val Pro Ile Phe Gly Glu
225                 230                 235                 240

Ser Glu Glu Asp Tyr Asp Asp Leu Gly Gln Val Thr Gly Glu Ala
                245                 250                 255

Val Thr Pro Ser Val Ile Asp Asn Ile Leu Ser Lys Ile Glu Asn Glu
            260                 265                 270

Tyr Glu Val Leu Tyr Leu Lys Pro Leu Ala Gly Val Tyr Arg Ser Leu
                275                 280                 285

Lys Lys Gln Leu Glu Asn Asn Val Met Thr Phe Asn Val Asn Val Lys
            290                 295                 300

Asp Ile Leu Asn Ser Arg Phe Asn Lys Arg Glu Asn Phe Lys Asn Val
305                 310                 315                 320

Leu Glu Ser Asp Leu Ile Pro Tyr Lys Asp Leu Thr Ser Ser Asn Tyr
                325                 330                 335

Val Val Lys Asp Pro Tyr Lys Phe Leu Asn Lys Glu Lys Arg Asp Lys
            340                 345                 350
```

```
Phe Leu Ser Ser Tyr Asn Tyr Ile Lys Asp Ser Ile Asp Thr Asp Ile
            355                 360                 365

Asn Phe Ala Asn Asp Val Leu Gly Tyr Lys Ile Leu Ser Glu Lys
        370                 375                 380

Tyr Lys Ser Asp Leu Asp Ser Ile Lys Lys Tyr Ile Asn Asp Lys Gln
385                 390                 395                 400

Gly Glu Asn Glu Lys Tyr Leu Pro Phe Leu Asn Asn Ile Glu Thr Leu
                405                 410                 415

Tyr Lys Thr Val Asn Asp Lys Ile Asp Leu Phe Val Ile His Leu Glu
            420                 425                 430

Ala Lys Val Leu Asn Tyr Thr Tyr Glu Lys Ser Asn Val Glu Val Lys
            435                 440                 445

Ile Lys Glu Leu Asn Tyr Leu Lys Thr Ile Gln Asp Lys Leu Ala Asp
            450                 455                 460

Phe Lys Lys Asn Asn Asn Phe Val Gly Ile Ala Asp Leu Ser Thr Asp
465                 470                 475                 480

Tyr Asn His Asn Asn Leu Leu Thr Lys Phe Leu Ser Thr Gly Met Val
                485                 490                 495

Phe Glu Asn Leu Ala Lys Thr Val Leu Ser Asn Leu Leu Asp Gly Asn
                500                 505                 510

Leu Gln Gly Met Leu Asn Ile Ser Gln His Gln Cys Val Lys Lys Gln
            515                 520                 525

Cys Pro Gln Asn Ser Gly Cys Phe Arg His Leu Asp Glu Arg Glu Glu
            530                 535                 540

Cys Lys Cys Leu Leu Asn Tyr Lys Gln Glu Gly Asp Lys Cys Val Glu
545                 550                 555                 560

Asn Pro Asn Pro Thr Cys Asn Glu Asn Asn Gly Gly Cys Asp Ala Asp
                565                 570                 575

Ala Lys Cys Thr Glu Glu Asp Ser Gly Ser Asn Gly Lys Lys Ile Thr
            580                 585                 590

Cys Glu Cys Thr Lys Pro Asp Ser Tyr Pro Leu Phe Asp Gly Ile Phe
            595                 600                 605

Cys Ser Ser Ser Asn
    610

(2) INFORMATION FOR SEQ ID NO: 23:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 23:

Thr Ala Cys Asp Leu Ala Pro Pro Ala Gly Thr Thr Asp
                5                   10

(2) INFORMATION FOR SEQ ID NO: 24:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein
```

```
(xi) SEQUENCE DESCRIPTION: SEQ ID NO: 24:

Ala Ala His Pro Gly Arg Ser Val Val Pro Ala Leu Leu Pro Leu Leu Ala
                5                   10                  15

Gly Thr Leu Leu Leu Glu Thr Ala Thr Pro
        20                  25
```